US007601713B2

(12) United States Patent
Ding et al.

(10) Patent No.: US 7,601,713 B2
(45) Date of Patent: Oct. 13, 2009

(54) KINASE INHIBITORS AND THEIR USES

(75) Inventors: Pingyu Ding, Foster City, CA (US);
Ankush Argade, Foster City, CA (US);
Dane Goff, Redwood City, CA (US);
Rajinder Singh, Belmont, CA (US);
Esteban Masuda, Menlo Park, CA
(US); Vanessa Taylor, San Francisco,
CA (US); Sacha Holland, San
Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 123 days.

(21) Appl. No.: 11/611,568

(22) Filed: Dec. 15, 2006

(65) Prior Publication Data

US 2007/0142402 A1 Jun. 21, 2007

Related U.S. Application Data

(60) Provisional application No. 60/751,393, filed on Dec. 15, 2005.

(51) Int. Cl.
| | |
|---|---|
| A61K 31/519 | (2006.01) |
| A61K 31/52 | (2006.01) |
| A61K 31/517 | (2006.01) |
| C07D 498/04 | (2006.01) |
| C07D 487/04 | (2006.01) |
| C07D 473/16 | (2006.01) |
| A61K 31/5355 | (2006.01) |
| A61K 31/497 | (2006.01) |
| A61K 31/551 | (2006.01) |
| C07D 265/36 | (2006.01) |
| C07D 413/12 | (2006.01) |
| C07D 403/12 | (2006.01) |
| C07D 243/08 | (2006.01) |
| A61P 19/02 | (2006.01) |
| C07D 239/84 | (2006.01) |
| C07D 471/04 | (2006.01) |
| C07D 401/12 | (2006.01) |

(52) U.S. Cl. .............. 514/230.5; 514/266.4; 514/234.2;
514/218; 514/252.16; 514/252.17; 514/252.11;
514/260.1; 514/265.1; 514/258.1; 514/264.11;
514/263.2; 514/263.4; 514/263.22; 514/263.24;
514/262.1; 544/291; 544/277; 544/105; 544/280;
544/118; 544/117; 544/253; 544/279; 544/262;
544/285; 544/278; 540/575

(58) Field of Classification Search .................. 544/277,
544/105, 118, 262, 117; 514/263.2, 263.21,
514/263.22, 263.37, 234.2, 230.5, 252.16,
514/252.17, 263.4, 263.24, 262.1
See application file for complete search history.

(56) References Cited

U.S. PATENT DOCUMENTS

| 7,041,824 B2 * | 5/2006 | Bordon-Pallier et al. ..... 544/277 |
| 2005/0176707 A1 | 8/2005 | Chen et al. |
| 2006/0035891 A1 | 2/2006 | Li et al. |
| 2007/0135457 A1 * | 6/2007 | Beyer et al. ............. 514/264.11 |

FOREIGN PATENT DOCUMENTS

| WO | WO9716452 A | 5/1997 |
| WO | WO0049018 | 8/2000 |

(Continued)

(Continued)

OTHER PUBLICATIONS

Goldman, et al., N. England J. Med., 344, 14, Apr. 5, 2001.*

(Continued)

*Primary Examiner*—Mark L Berch
*Assistant Examiner*—Cecilia M Jaisle
(74) *Attorney, Agent, or Firm*—McDonnell Boehnen Hulbert & Berghoff LLP

(57) ABSTRACT

The present disclosure provides compounds that inhibit protein kinases, such as JAK, Axl, or Syk kinases, compositions comprising the compounds and methods of using the compounds to inhibit protein kinase and treat and/or prevent diseases associated with inappropriate kinase activity. The compounds of the present invention are according to structural formula (I):

$$R^4\underset{H}{N}{-}B{-}\underset{H}{N}R^2$$

or a salt or N-oxide thereof, wherein
B is selected from (B.1b)

and (B.1h)

42 Claims, No Drawings

FOREIGN PATENT DOCUMENTS

| WO | WO 0109134 A1 | 2/2001 |
| WO | WO 0132632 A2 | 5/2001 |
| WO | WO 02102314 * | 12/2002 |
| WO | WO 2004037823 A1 | 5/2004 |
| WO | WO 2005016528 * | 2/2005 |
| WO | WO 2005047524 A2 | 5/2005 |
| WO | WO 2005049616 A1 | 6/2005 |
| WO | WO 2005097135 A2 | 10/2005 |
| WO | WO2005118544 | 12/2005 |
| WO | WO2006055528 | 5/2006 |
| WO | WO2006055561 | 5/2006 |

OTHER PUBLICATIONS

Ekman, et al., Oncogene (2000) 19, 4151-58.*
Xu, et al., J. Biol. Chem., 273, 50, Dec. 11, 1998. 33230-38.*
Zhang, et al., J. Biol. Chem., vol. 279, No. 53, Dec. 31, 2004, pp. 55348-55354.*
Lopes de Menezes, et al., Clin. Cancer Res. 2005:11 (14), Jul. 15, 2005, 5281-91.*
Kawahara, et al., J. Clin. Onc., 2006 ASCO Annual Meeting Proceedings, Part I, vol. 24, No. 18S, Jun. 20, 2006, 13163.*
Yoshida, et al., J. Neurochem., 2004, 90, 352-58.*
Griesser, Chapter 8, The Importance of Solvates (pp. 211-230), in the text, Polymorphism: In the Pharmaceutical Industry, Hilfiker, 2006.*
Brandlin, et al., J. Biol. Chem., vol. 277, No. 8, 2002, 6490-6496.*
Wu, et al., Am. J. Pathol., 156, Jun. 6, 2000.*
Rane, et al., Oncogene (2000) 19, 5662-5679.*
Oshiro, et al., Clinical Cancer Research, vol. 7, 4262-4271, Dec. 2001.*
Nakano, et al., FEBS Letters, 387 (1996) 75-77.*
Kyttaris, et al., Clin Immunol. Sep. 2007; 124(3): 235-237.*
Khan, et al., Journal of Allergy and Clinical Immunology, vol. 119, Issue 5, Mar. 6, 2007, p. 1277.*
Brittain, Chapter V of Polymorphism in Pharmaceutical Solids, 1999, pp. 126-127.*
Perreira, et al., "Reversine" and its 2-Substituted Adenine Derivatives as Potent and Selective A3 Adenosine Receptor Antagonists, J Med Chem, 2005, 48 (15), pp. 4910-4918.

* cited by examiner

KINASE INHIBITORS AND THEIR USES

CROSS-REFERENCE TO RELATED APPLICATIONS

This application claims the benefit under 35 U.S.C. § 119(e) of U.S. Provisional Patent Application Ser. No. 60/751,393, filed on Dec. 15, 2005.

1. FIELD

The present disclosure provides compounds that inhibit protein kinases, prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of various diseases that are responsive to protein kinase inhibition and/or that are mediated, at least in part, by inappropriate protein kinase activity.

2. BACKGROUND

Protein kinases participate in the signaling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues (Hanks & Hunter T, 1995, FASEB. J. 9:576-596). The serine/threonine kinases include, for example, protein kinase C isoforms (Newton, 1995, J. Biol. Chem. 270: 28495-28498) and a group of cyclin-dependent kinases such as cdc2 (Pines, 1995, Trends in Biochemical Sciences 18:195-197). The tyrosine kinases include membrane-spanning growth factor receptors such as the epidermal growth factor receptor (Iwashita & Kobayashi, 1992, Cellular Signaling 4:123-132), and cytosolic non-receptor kinases such as ZAP-70 and csk kinases (Chan et al., 1994, Ann. Rev. Immunol. 12:555-592).

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

2.1 Axl Kinase

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTKs, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (ECs) and vascular smooth muscle cells (VSMCs) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl−/− mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis is also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemias. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

2.2 JAK Kinase

JAK kinases (JAnus Kinases) are a family of cytoplasmic protein tyrosine kinases including JAK1, JAK2, JAK3 and TYK2. Each of the JAK kinases is selective for the receptors of certain cytokines, though multiple JAK kinases may be affected by particular cytokine or signaling pathways. Studies suggest that JAK3 associates with the common gamma (γc) chain of the various cytokine receptors. JAK3 in particular selectively binds to receptors and is part of the cytokine signaling pathway for IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-α. Upon binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Phosphorylated JAK kinases bind various STAT (Signal Transducer and Activator of Transcription) proteins. STAT proteins, which are DNA binding proteins activated by phosphorylation of tyrosine residues, function both as signaling molecules and transcription factors and ultimately bind to specific DNA sequences present in the promoters of cytokine-responsive genes (Leonard et al., (2000), *J. Allergy Clin. Immunol.* 105:877-888). JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas. For a review of the pharmaceutical intervention of the JAK/STAT pathway see Frank, (1999), *Mol. Med.* 5:432:456 and Seidel et al., (2000), *Oncogene* 19:2645-2656.

JAK3 in particular has been implicated in a variety of biological processes. For example, the proliferation and survival of murine mast cells induced by IL-4 and IL-9 have been shown to be dependent on JAK3- and gamma chain-signaling (Suzuki et al., (2000), *Blood* 96:2172-2180). JAK3 also plays a crucial role in IgE receptor-mediated mast cell degranulation responses (Malaviya et al., (1999), *Biochem. Biophys. Res. Commun.* 257:807-813), and inhibition of JAK3 kinase has been shown to prevent type I hypersensitivity reactions, including anaphylaxis (Malaviya et al., (1999), *J. Biol. Chem.* 274:27028-27038). JAK3 inhibition has also been shown to result in immune suppression for allograft rejection (Kirken, (2001), *Transpl. Proc.* 33:3268-3270). JAK3 kinases have also been implicated in the mechanism involved in early and late stages of rheumatoid arthritis (Muller-Ladner et al., (2000), *J. Immunal.* 164:3894-3901); familial amyotrophic lateral sclerosis (Trieu et al., (2000), *Biochem Biophys. Res. Commun.* 267:22-25); leukemia (Sudbeck et al., (1999), *Clin. Cancer Res.* 5:1569-1582); mycosis fungoides, a form of T-cell lymphoma (Nielsen et al., (1997), *Prac. Natl. Acad. Sci. USA* 94:6764-6769); and abnormal cell growth (Yu et al., (1997), *J. Immunol.* 159:5206-5210; Catlett-Falcone et al., (1999), *Immunity* 10:105-115).

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), *Mol. Cell. Biol.* 16:4710-6; Jurlander et al., (1997), *Blood.* 89:4146-52; Kaneko et al., (1997), *Clin. Exp. Immun.* 109:185-193; and Nakamura et al., (1996), *J. Biol. Chem.* 271:19483-8). They are also known to be important to lymphocyte differentiation, function and survival. JAK-3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) *Am. J. Transplant* 4:51-57; Changelian (2003) *Science* 302:875-878). Conditions in which targeting of the JAK pathway or modulation of the JAK kinases, particularly JAK3, may be therapeutically useful include, leukemia, lymphoma, transplant rejection (e.g. pancreas islet transplant rejection, bone marrow transplant applications (e.g. graft-versus-host disease), autoimmune diseases (e.g. diabetes), and inflammation (e.g. asthma, allergic reactions). Conditions which may benefit for inhibition of JAK3 are discussed in greater detail below.

In view of the numerous conditions that may benefit by treatment involving modulation of the JAK pathway it is immediately apparent that new compounds that modulate JAK pathways and methods of using these compounds should provide substantial therapeutic benefit to a wide variety of patients.

2.3 Syk Kinase

Crosslinking of Fc receptors, such as the high affinity receptor for IgE (FcεRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcεRI and/or FcγRI comprises an array of cellular proteins. Among the most important intracellular signal propagators are the tyrosine kinases. And, an important tyrosine kinase involved in the signal transduction pathways associated with crosslinking the FcεRI and/or FcγRI receptors, as well as other signal transduction cascades, is Syk kinase (see Valent et al., 2002, Intl. J. Hematol. 75(4):257-362 for review). The mediators released as a result of FcεRI and FcγRI receptor cross-linking are responsible for, or play important roles in, the manifestation of numerous adverse events. Therefore, there exists a need for compounds which are able to effectly inhibit Syk kinase.

3. SUMMARY

In one aspect, the present invention provides compounds that exhibit biological activities, such as the ability to inhibit protein kinases. The compounds generally comprise three main structural features: (i) a saturated or unsaturated, bridged or unbridged cycloalkyl "A" ring that optionally includes an amide or ester substituent; (ii) an optionally substituted bicyclic heteroaryl "B" ring; and (iii) an optionally substituted aryl or heteroaryl "C" ring. The "A" and "C" rings, which are described in more detail in connection with substituent $R^4$ and $R^2$, respectively, below, are linked to the "B" ring via a linker. Typical linkers include, but are not limited to, —NH—, —S—, —C(O)—, —S(O)$_2$—, —NR—

—C(O)—, —NR—C(O)—NR—, —O—C(O)—NR, —NR—C(S)—, —NR—C(S)—NR—, —CH₂—, —CH₂—CH₂—, —CH=CH—, —C≡C—, where R is hydrogen, $C_1$-$C_8$ alkyl, ($C_6$-$C_{10}$) aryl or ($C_7$-$C_{16}$) arylalkyl. The center "B" ring can be any ring now known or later found to be useful as a scaffold in molecules that inhibit protein kinases.

In some embodiments, the compounds are described by structural formula (I): below:

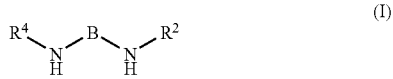

(I)

including the salts, hydrates, solvates and N-oxides thereof, wherein B is a ring according to structural formula (B.1),

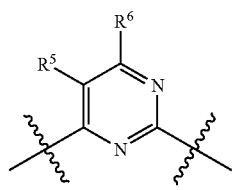

B.1 wherein $R^5$ and $R^6$ substituents are taken together to form a saturated or unsaturated alkylene or saturated or unsaturated heteroalkylene bridge which may be optionally substituted at one or more carbon or heteroatoms, as will be described in more detail, below.

In some embodiments, the alkylene bridge formed by $R^5$ and $R^6$ is selected from the group consisting of —CH=CH—CH=CH—, —N=CH—CH—, —N=CH—Y—, —CH=N—Y—, Y—N=CH—, —CH=CH—Y—, —Y—CH=CH—, and a $C_3$-$C_4$ alkylene group wherein one CH₂ group is optionally replaced by Y, wherein Y is selected from the group consisting of O, S and NH. In the compounds of structural formula (I), $R^4$ represents the saturated or unsaturated, optionally bridged cycloalkyl "A" ring that includes an amide or ester $R^7$ substituent, although in instances in which the cycloalkyl ring includes two or more bridgehead carbon atoms, or in instances in which the cycloalkyl ring is unsaturated, this $R^7$ substituent is optional. The $R^7$ substituent can be positioned at any carbon atom on the cycloalkyl ring, including on a bridgehead or bridging carbon atom. In some embodiments, the $R^7$ substituent is positioned on the carbon atom attaching the cycloalkyl ring to the remainder of the molecule. In some embodiments, the substituent is positioned on the carbon atom adjacent to the carbon atom attaching the cycloalkyl ring to the remainder of the molecule, or on its next-nearest neighbor.

$R^2$ represents the "C" ring. The nature of the $R^2$ group can vary widely. For example, the $R^2$ group can be an optionally substituted aryl, heteroaryl, arylalkyl or heteroarylalkyl group. In some embodiments, $R^2$ is a phenyl group that includes from one to three of the same or different substituents. The substituents can be selected from the group consisting of virtually any substituent group, including, but not limited to, branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities may be protected or unprotected, as is well-known in the art. In some embodiments, at least one of the substituents is a water-solubilizing group.

As will be appreciated by skilled artisans, the $R^4$ ring can contain chiral centers. For example, the carbon atom connecting the $R^4$ ring to the remainder of the molecule, and the carbon atom including the $R^7$ substituent can be chiral centers. If the $R^4$ ring includes, for example, non-equivalent bridges, the bridgehead carbon atoms can also be chiral centers. As a consequence of these (and other) chiral centers, the compounds described herein can include various enantiomers and/or diastereomers in racemic or enriched forms. For example, when the $R^4$ ring is an unbridged, saturated or unsaturated cycloalkyl ring that includes an $R^7$ substituent on the carbon atom adjacent to the carbon atom attaching the cycloalkyl ring to the remainder of the molecule, the compounds of formula (I) include two racemates, a cis racemate and a trans racemate, that together comprise four diastereomers. These four diastereomers are illustrated below (absolute configuration assignments determined assuming $R^7$ is an ester or amide group, and $R^7$ resides on carbon two of the cycloalkyl ring, the pyrimidine 4-nitrogen resides on carbon one of the cycloalkyl ring):

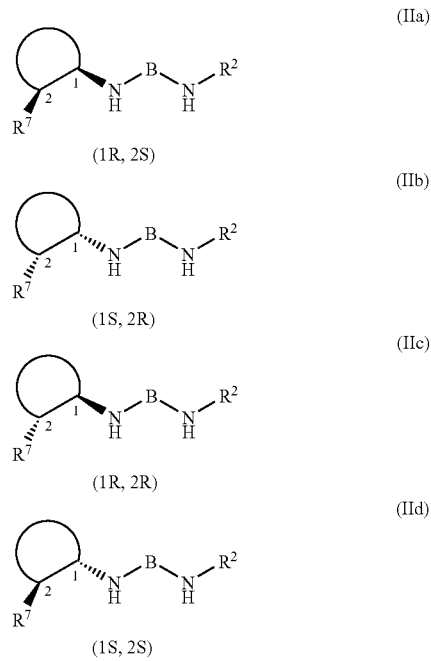

In the above structures, "B", $R^2$ and $R^7$ are as previously defined for structural formula (I). The illustrated ring including the $R^7$ substituent could be any lower unbridged, saturated or unsaturated cycloalkyl ring. Moreover, while the $R^7$ substituent is illustrated at a specific location, it could be at other locations.

When $R^4$ is a saturated or unsaturated bridged cycloalkyl having bridges that allow for exo-endo geometries and an $R^7$ substituent on a carbon atom adjacent to the carbon atom attaching the cycloalkyl ring to the remainder of the molecule, the compounds of formula (I) include two cis racemates, an exo-exo and an endo-endo, and two trans racemates, an exo-endo and an endo-exo. For example, when $R^4$ comprises a norbornyl or norbornenyl bonded to the remainder at the molecule at its 2-position, these racemates are represented below:

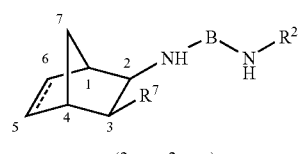

(III.r1)

(2-exo-3-exo)

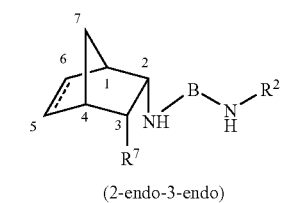

(III.r2)

(2-endo-3-endo)

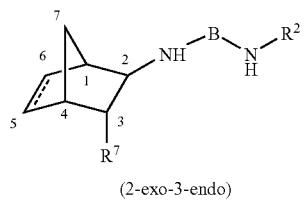

(III.r3)

(2-exo-3-endo)

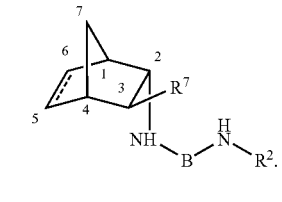

(III.r4)

(2-endo-3-exo)

Together these four racemates comprise eight diastereomers, which are illustrated below (absolute configuration assignments determined assuming $R^7$ is an ester or amide group):

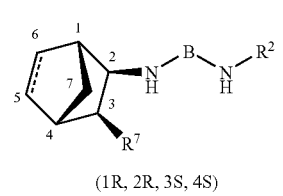

(IVa)

(1R, 2R, 3S, 4S)

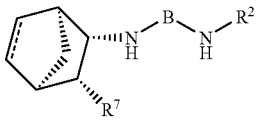

(IVb)

(1S, 2S, 3R, 4R)

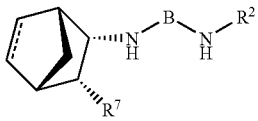

(IVc)

(1R, 2S, 3R, 4S)

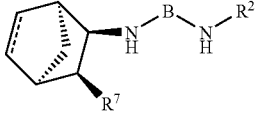

(IVd)

(1S, 2R, 3S, 4R)

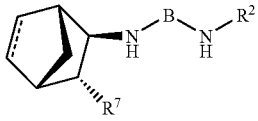

(IVe)

(1R, 2R, 3R, 4S)

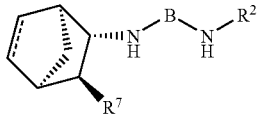

(IVf)

(1S, 2S, 3S, 4R)

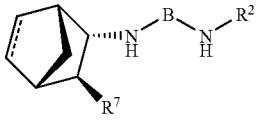

(IVg)

(1R, 2S, 3S, 4S)

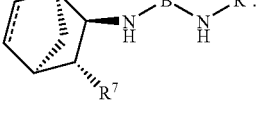

(IVh)

(1S, 2R, 3R, 4R)

In the above-illustrated diastereomers, the bond including the dotted line can be a single bond or a double bond.

Although the racemates and diastereomers illustrated above are exemplified with a specific bridged cycloalkyl $R^4$ ring, it should be appreciated that the $R^4$ ring could be virtually any saturated or unsaturated bridged cycloalkyl in which, for example, the carbon atoms corresponding to the illustrated 1-, 2-, 3- and 4-carbon atoms are chiral centers. Moreover, although the illustrated ring includes a specified bridge position and a single bridging carbon atom, the ring could include more bridging atoms, and the bridgehead carbon atoms could be positioned at different locations within the cycloalkyl ring. In addition, the ring could include additional bridgehead and bridging carbon atoms such that it contains more than one bridge. Depending on its structure, additional chiral centers can be in the saturated or unsaturated bridged cycloalkyl can include additional chiral center.

Recently, it has been discovered that for a specific 2,4 pyrimidinediamine compound, N4-2(-aminocarbonylcyclopent-1-yl)-5-fluoro-N2-[4-(4-methylpiperazin-1-yl)3-methylphenyl]-2,4 pyrimidinediamine, the two cis(1S,2R) and (1R,2S) diastereomers and the trans(1R,2R) diastereomer inhibited Aurora kinases and exhibited antiproliferative activity against a variety of different tumor cell types in vitro assays, whereas the trans(1S,2S) diastereomer is relatively inactive against these same tumor cells (see, e.g., application Ser. No. 11/133,419 filed May 18, 2005, and international application No. PCT/US05/17470 filed May 18, 2005). Based on this observation, it is expected that the cis racemates, the two cis diastereomers, and the trans diastereomer of the compounds described herein that correspond in absolute stereochemical configuration to the cis and trans diastereomers of structural formulae (Ia), (IIb) and (IIc), respectively, will similarly exhibit biological activity.

Biological activity was also observed with the cis racemate of certain N4-(3-aminocarbonylbicycle[2.2.1]hept-5-ene-2-yl)-N2-substituted phenyl-2,4-pyrimidinediamine compounds. While both cis racemates exhibited significant antiproliferative activity against tumor cells in in vitro assays, the exo-exo racemate was approximately twenty-fold more potent than the endo-endo racemate. Moreover, for the exo-exo racemates, the enantiomers corresponding to structural formula (IVa), i.e., the (1R,2R,3S,4S) diastereomers, were found to be largely responsible for the potency of the racemate, being approximately 1000-fold more potent than their corresponding enantiomers, i.e., the (1S,2S,3R,4R) diastereomer (IVb). This (1R,2R,3S,4S) diastereomer was also approximately 20-50 times more potent than the endo-endo racemate (see, e.g., copending application Ser. Nos. 11/133,419 filed May 18, 2005, Ser. No. 11/280,066 filed Nov. 15, 2005 and Ser. No. 11/281,186 filed Nov. 15, 2005 and international application Nos. PCT/US05/017470 filed May 18, 2005, PCT/US05/041276 filed Nov. 15, 2005 and PCT/US05/041359 filed Nov. 15, 2005).

Based on this observation, it is expected that the racemates and diastereomers of the compounds described herein that correspond in absolute stereochemical configuration to the exo-exo and endo-endo cis racemates of structural formulae (III.r1) and (III.r2), and to the (1R,2R,3S,4S) diastereomer of structural formula (IVa), will exhibit biological activities. Moreover, it is expected that any diastereomer corresponding in absolute stereochemical configuration to the diastereomer of structural formula (IVa) will exhibit similarly superior potency as compared to the other diastereomers.

When the $R^4$ cycloalkyl ring is a norbornyl or norbornenyl, synthesizing the trans racemates and diastereomers may be difficult owing to steric constraints. However, where trans diastereomers of bridged cycloalkyl groups are possible, the diastereomers corresponding to structural formulae (IVf) and (IVg), supra, are expected to exhibit biological activity.

Thus, in another aspect, the present disclosure provides compounds that are enriched in one or more of the racemates, enantiomers and/or diastereomers corresponding to those described above. In some embodiments, the stereoisomerically enriched compounds are cis racemates. In a specific embodiment, the stereoisomerically enriched compounds are exo-exo or endo-endo cis racemates corresponding to structural formulae (III.r1) and (III.r2). In some embodiments, the stereoisomerically enriched compounds are enriched in one or more cis diastereomers. In some embodiments, the stereoisomerically enriched compounds are enriched in one or more diastereomers corresponding to structural formula (IIa), (IIb) and (IIc). In a specific embodiment, the stereoisomerically enriched compound is a diastereomer according to structural formula (IIa), (IIb) or (IIc) that is substantially free of all other diastereomers. In some embodiments, the stereoisomerically enriched compounds are enriched in the diastereomer corresponding to structural formula (IVa). In a specific embodiment, the stereoisomerically enriched compound is a diastereomer corresponding to structural formula (IVa) that is substantially free of all other diastereomers.

In still another aspect, prodrugs of the compounds and/or stereoisomerically enriched compounds (referred to collectively herein as "compounds") are provided. Such prodrugs may be active in their prodrug form, or may be inactive until converted under physiological or other conditions of use to an active drug form. In the prodrugs, one or more functional groups of the compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs include special types of protecting groups, termed "progroups," masking one or more functional groups of the compounds that cleave under the conditions of use to yield an active drug compound. Functional groups within the compounds that may be masked with progroups for inclusion in a promoiety include, but are not limited to, amines (primary and secondary), hydroxyls, sulfanyls (thiols), carboxyls, carbonyls, etc. Myriad progroups suitable for masking such functional groups to yield promoieties that are cleavable under the desired conditions of use are known in the art. All of these progroups, alone or in combination, may be included in the prodrugs. Specific examples of promoieties that yield primary or secondary amine groups that can be included in the prodrugs include, but are not limited to amides, carbamates, imines, ureas, phosphenyls, phosphoryls and sulfenyls. Specific examples of promoieties that yield sulfanyl groups that can be included in the prodrugs include, but are not limited to, thioethers, for example S-methyl derivatives (monothio, dithio, oxythio, aminothio acetyls), silyl thioethers, thioesters, thiocarbonates, thiocarbamates, asymmetrical disulfides, etc. Specific examples of promoieties that cleave to yield hydroxyl groups that can be included in the prodrugs include, but are not limited to, sulfonates, esters, carbonates, phosphates (phosphonoxy) and their salts with organic bases and metals. Specific examples of promoieties that cleave to yield carboxyl groups that can be included in the prodrugs include, but are not limited to, esters (including silyl esters, oxamic acid esters and thioesters), amides and hydrazides.

In another aspect, the present disclosure provides intermediates useful for synthesizing the compounds and/or prodrugs described herein. In an illustrative embodiment, the intermediates are compounds according to structural formula (V):

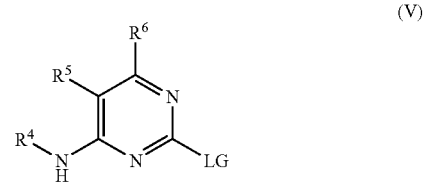

(V)

wherein $R^4$, $R^5$ and $R^6$ are as previously defined and LG represents a leaving group. Suitable leaving groups include, but are not limited to, quaternary ammonium salts, —S(O)$_2$Me, —SMe and halo (e.g., F, Cl, Br, I). In a specific embodiment, the leaving group LG is chloro.

The intermediates of structural formula (V) may be stereoisomerically enriched in one or more diastereomers such that they can be used to synthesize compounds enriched in one or more of the various diastereomers discussed above.

In still another aspect, compositions comprising one or more of the compounds described herein are provided. The compositions generally comprise the compound(s), and/or prodrugs, salts, hydrates, solvates and/or N-oxides thereof, and an appropriate carrier, excipient and/or diluent. The exact nature of the carrier, excipient and/or diluent will depend upon the desired use for the composition, and may range from being suitable or acceptable for in vitro uses, to being suitable or acceptable for veterinary uses, to being suitable or acceptable for use in humans.

The compounds described herein inhibit protein kinases in in vitro assays. Thus, in still another aspect, methods of inhibiting protein kinases are provided. The methods generally involve contacting a protein kinase with an amount of one or more compounds described herein, and/or prodrugs, salts, hydrates, solvates and/or N-oxides thereof, effective to inhibit its activity. The methods may be practiced in in vitro contexts, or in in vivo contexts as a therapeutic approach towards the treatment or prevention of disorders responsive to protein kinase inhibition. Protein kinases that can be inhibited with the compounds desired herein include, but are not limited JAK1, JAK3, Axl, Syk, Lck and Lyn Kinases.

In still another aspect, methods of treating, inhibiting, and/or preventing diseases that are responsive to protein kinase inhibition, or in which inappropriate protein kinase activity plays a role, are provided. The methods may be practiced in animals in veterinary contexts or in humans. The methods generally involve administering to an animal or human subject an amount of one or more compounds described herein, and/or prodrugs, salts, hydrates, solvates and/or N-oxides thereof, effective to treat and/or prevent the particular disease. The compound(s) per se can be administered to the subject, or the compound(s) can be administered in the form of a composition. Diseases that are responsive to protein kinase inhibition, and/or that are believed to be effected, at least in part, by inappropriate protein kinase activity, that can be treated inhibited, and/or prevented according to the methods include, but are not limited to, autoimmune diseases such as rheumatoid arthritis, multiple sclerosis, and systemic lupus erythematosus, in transplant rejection, in graft v host disease, in hyperproliferative disorders such as tumors, psoriasis, in pannus formation in rheumatoid arthritis, restenosis following angioplasty and atherosclerosis, in osteoporosis and in diseases in which cells receive pro-inflammatory signals such as asthma, inflammatory bowel disease and pancreatitis.

In particular, inhibition of Syk and/or Lyn kinase would be expected to be useful in treating, inhibiting, and/or preventing diseases that are characterized by caused by and/or associated with the IgE receptor signaling cascade which leads to degranulation of immune cells such as mast cells, and the consequent release of mediators of inflammation. Such diseases include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

In another embodiment, inhibition of Syk kinase would be expected to be useful in treating, inhibiting, and/or preventing diseases that are characterized by caused by and/or associated with autoimmune diseases and/or symptoms of such diseases. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia (including immune thrombocytopenia purpura), sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include autoimmune alopecia, Type I or juvenile onset diabetes, and thyroiditis.

Inhibition of JAK kinase would be expected to be useful in treating, inhibiting, and/or preventing diseases that are characterized by caused by and/or associated with signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. Such diseases include, by way of example and not limitation, allergies, asthma, autoimmune diseases such as transplant rejection (e.g., kidney, heart, lung, liver, pancreas, skin; host versus graft reaction (HVGR), etc.), rheumatoid arthritis, and amyotrophic lateral sclerosis, T-cell mediated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

Inhibition of Axl kinase would be expected to be useful in treating, inhibiting, and/or preventing diseases that are characterized by caused by and/or associated with apoptosis induced by serum starvation, TNF-α or the viral protein E1A, as well as migration and cell differentiation. Such diseases include, by way of example and not limitation, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

Other aspects include, but are not limited to, intermediates and methods useful for synthesizing the stereoisomerically enriched compounds and prodrugs, as will be described in more detail herein below.

4. DETAILED DESCRIPTION

4.1 Definitions

Herein the term and/or is used and means that either one of or both or two options is an available option. For example, "optionally substituted with one or more $R^a$ and/or $R^b$" means that if only one substituent is present, then it is either $R^a$ or $R^b$; if more than one substituent is present, the each substituent, independently, is $R^a$ or $R^b$.

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., $C_1$-$C_6$ means one to six carbon atoms) that is derived by the removal of one hydrogen atom from a single carbon atom of a parent alkane, alkene or alkyne. Cyclic alkyls can include zero bridgehead carbon atoms or two or more bridgehead carbon atoms. Thus, cyclic alkyls can be monocyclic, bicyclic or polycyclic in structure. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., $C_1$-$C_6$ means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group containing 1 to 8 carbon atoms. In some embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycloalkylalkyl" as used herein, means a heterocycle, as defined herein, appended to the parent molecular moiety through an alkyl group, as defined herein.

"Cycloalkyl" by itself or as part of another substituent refers to a cyclic version of an "alkyl" group. A cycloalkyl group may include zero bridgehead carbon atoms or two or more bridgehead carbon atoms. Thus, a cycloalkyl may be monocyclic, bicyclic or polycyclic, depending upon the number of bridgehead and bridging carbon atoms. Cycloalkyl groups that include zero bridgehead carbon atoms are referred to herein as "monocyclic cycloalkyls" or "unbridged cycloalkyls." Cycloalkyls that include at least two bridgehead carbon atoms and at least one bridging carbon atom are referred to herein as "bridged cycloalkyls." Bridged cycloalkyls that include two bridgehead carbon atoms are referred to herein as "bicyclic bridged cycloalkyls." Bridged cycloalkyls that include more than two bridgehead carbon atoms are referred to herein as "polycyclic bridged cycloalkyls." Typical unbridged cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical bridged cycloalkyls include, but are not limited to, adamantyl, noradamantyl, bicyclo[1.1.0]butanyl, norboranyl (bicyclo[2.2.1]heptanyl), norbornenyl (bicyclo[2.2.1]heptanyl), norbornadienyl (bicyclo[2.2.1]heptadienyl), tricyclo[2.2.1.0]heptanyl, bicyclo[3.2.1]octanyl, bicyclo[3.2.1]octanyl, bicyclo[3.2.1]octadienyl, bicyclo[2.2.2]octanyl, bicyclo[2.2.2]octenyl, bicyclo[2.2.2]octadienyl, bicyclo[5,2,0] nonanyl, bicyclo[4.3.2]undecanyl, tricyclo[5.3.1.1]dodecanyl, and the like. Where specific levels of saturation are intended, the nomenclature cycloalkanyl and cycloalkenyl is used. A "lower" unbridged cycloalkyl contains from 3 to 8 carbon atoms. A "lower" bridged cycloalkyl contains from 5 to 16 carbon atoms.

"Heteroalkyl," "heteroalkanyl," "heteroalkenyl," "heteroalkynyl," "heteroalkylene," and "heterocycloalkyl" refer to an alkyl, alkanyl, alkenyl, alkynyl, alkylene or cycloalkyl group, respectively, containing 3 to 12 carbon atoms in which one to four of the carbon atoms is replaced with one or more heteroatoms or heteroatomic groups selected from the group consisting of O, S and NH. Examples of heterocycloalkyl groups include, but are not limited to, morpholinyl, pyrrolinyl, pyrazolinyl, tetrahydrofuranyl, tetrahydrothienyl, tetrahydropyranyl, dioxanyl, dioxolanyl, piperidinyl, and piperazinyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, a monocyclic heteroaryl fused to a cycloalkenyl, a monocyclic heteroaryl fused to a monocyclic heteroaryl, or a monocyclic aryl group fused to a heterocycloalkyl group. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroindolyl, dihydrobenzofuranyl, dihydroquinolinyl, dihydroisoquinolinyl, furopyridinyl, benzodioxolyl, benzodioxepinyl, dihydrobenzooxazinyl, indazolyl, indolyl, isoquinolinyl, naphthyridinyl, quinolinyl, tetrahydroquinolinyl, and thienopyridinyl.

"Parent Aromatic Ring System" refers to an unsaturated cyclic or polycyclic ring system having a conjugated T electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., $C_6$-$C_{15}$ means from 6 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is ($C_6$-$C_{15}$) aryl, with ($C_6$-$C_{10}$) being more typical. Specific examples are phenyl and naphthyl.

The above-defined groups may include prefixes and/or suffixes that are commonly used in the art to create additional well-recognized substituent groups. As examples, "alkyloxy" or "alkoxy" refers to a group of the formula —OR, "alkylamine" refers to a group of the formula —NHR and "dialkylamine" refers to a group of the formula —NRR, where each R is independently an alkyl.

"Prodrug" refers to a derivative of an active compound (drug) that may require a transformation under the conditions of use, such as within the body, to release the active drug.

Prodrugs are frequently, but not necessarily, pharmacologically inactive until converted into the active drug. Prodrugs are typically obtained by masking a functional group in the drug compound believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active stereoisomerically enriched compounds described herein to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active stereoisomerically enriched drug compound to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Kinase-mediated process" or "Kinase-mediated disease or disorder" refers to a cellular process, disease or disorder in which a kinase plays a role. In some embodiments, the kinase is a JAK kinase. The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., 1996, *Mol. Cell. Biol.* 16:4710-6; Jurlander et al., 1997, *Blood.* 89:4146-52; Kaneko et al., 1997, *Clin. Exp. Immun.* 109:185-193; and Nakamura et al., 1996, *J. Biol. Chem.* 271:19483-8). They are also known to be important to lymphocyte differentiation, function and survival. JAK-3 in particular plays an essential role in the function of lymphocytes, macrophages, and mast cells. Non-limiting examples of JAK kinase mediated diseases that may be treated or prevented with the compounds, include, but are not limited to allergies, asthma, autoimmune diseases such as transplant rejection (e.g., kidney, heart, lung, liver, pancreas, skin; host versus graft reaction (HVGR), etc), rheumatoid arthritis, and amyotrophic lateral sclerosis, T-cell medicated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

"Therapeutically effective amount" refers to an amount of a compound sufficient to treat a specified disorder or disease, or one or more of its symptoms.

"Prophylactically effective amount" refers to an amount of a compound sufficient to prevent a subject from developing a specified disorder or disease. Typically, subjects in which prophylaxis is practiced are not suffering from the specified disorder or disease, but are recognized as being at an elevated risk for developing this disease or disorder based factors such as, but not limited to, diagnostic markers and family history.

"Syk Kinase" refers to the well-known 72kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, *J. Biochem.* (Tokyo) 130:177-186); see also Turner et al., 2000, *Immunology Today* 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as $Ca^{2+}$ mobilization and mitogen-activated protein kinase (MAPK) cascades and degranulation. Syk kinase also plays a critical role in integrin signaling in neutrophils (see, e.g., Mocsai et al. 2002, *Immunity* 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.2|, gi|496899|emb|Z29630.1|HSSYKPTK[496899] and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role, and biological responses effected by such Syk mimics and Syk mimic-dependent signaling cascades may be regulated, and in particular inhibited, with many of the prodrugs described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

4.2 The Compounds

As discussed in the Summary section, the present disclosure provides compounds that have useful biological activities, including the ability to inhibit a variety of protein kinases in in vitro assays. In an illustrative embodiment, the compounds are defined by structural formula (I) below:

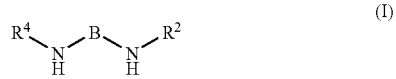

(I)

or a salt, hydrate, solvate or N-oxide thereof, wherein: B is

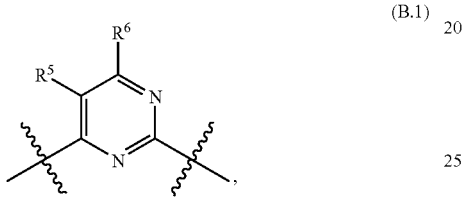

(B.1)

wherein $R^5$ and $R^6$ are taken together to form a saturated or unsaturated alkylene or saturated or unsaturated heteroalkylene bridge that contains from 3 to 4 chain atoms, optionally substituted with one or more groups which are each independently $R^a$ and/or $R^b$;

$R^2$ is selected from the group consisting of a ($C_6$-$C_{20}$) aryl optionally substituted with one or more of the same or different $R^8$ groups, a 5-20 membered heteroaryl optionally substituted with one or more of the same or different $R^8$ groups, a ($C_7$-$C_{28}$) arylalkyl optionally substituted with one or more of the same or different $R^8$ groups, and a 6-28 membered heteroarylalkyl optionally substituted with one or more of the same or different $R^8$ groups;

$R^4$ is a saturated or unsaturated, bridged or unbridged cycloalkyl containing a total of from 3 to 16 carbon atoms that is substituted with an $R^7$ group, with the proviso that when $R^4$ is an unsaturated unbridged cycloalkyl, or a saturated bridged cycloalkyl, this $R^7$ substituent is optional, wherein $R^4$ is optionally substituted with one or more groups which are independently $R^f$;

$R^7$ is selected from the group consisting of —C(O)OR$^d$, —C(O)NR$^d$R$^d$, —C(O)NR$^d$OR$^d$, or —C(O)NR$^d$NR$^d$R$^d$;

each $R^8$ group is, independently of the others, selected from the group consisting of a water-solubilizing group, $R^a$, $R^b$, $C_1$-$C_8$ alkyl optionally substituted with one or more of the same or different $R^a$ or $R^b$ groups, $C_3$-$C_8$ cycloalkyl optionally substituted with one or more of the same or different $R^a$ or $R^b$ groups, heterocycloalkyl containing 3 to 12 annular atoms, optionally substituted with one or more of the same or different $R^a$ or $R^b$ groups, $C_1$-$C_8$ alkoxy optionally substituted with one or more of the same or different $R^a$ or $R^b$ groups and —O—(CH$_2$)$_x$—$R^b$, where x is an integer ranging from 1 to 6;

each $R^a$ is, independently of the others, selected from the group consisting of hydrogen, $C_1$-$C_8$ alkyl, bridged or unbridged $C_3$-$C_{10}$ cycloalkyl, bridged or unbridged heterocycloalkyl containing 3 to 12 annular atoms, heteroaryl, ($C_6$-$C_{14}$) aryl, phenyl, naphthyl, ($C_7$-$C_{20}$) arylalkyl and benzyl wherein $R^a$ is optionally substituted with one or more groups which are each independently $R^f$;

each $R^b$ is, independently of the others, a suitable group selected from the group consisting of =O, —OR$^a$, ($C_1$-$C_3$) haloalkyloxy, —OCF$_3$, =S, —SR$^a$, =NR$^a$, =NOR$^a$, —NR$^c$R$^c$, halogen, —CF$_3$, —$C_1$-$C_3$haloalkyl, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^c$R$^c$, —S(O)$_2$NR$^c$R$^c$, —OS(O)R$^a$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(O)NR$^a$OR$^a$, —C(NH)NR$^c$R$^c$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NH)NR$^c$R$^c$ and —OC(NR$^a$)NR$^c$R$^c$;

each $R^c$ is, independently of the others, selected from the group consisting of $R^a$ or two $R^c$ that are bonded to the same nitrogen atom taken together with this nitrogen atom to which they are both attached form a heterocycloalkyl group containing 5 to 8 annular atoms, which optionally includes from 1 to 3 additional heteroatomic groups selected from the group consisting of O, S, N—(CH$_2$)$_y$—R$^a$, N—(CH$_2$)$_y$—C(O)R$^a$, N—(CH$_2$)$_y$—C(O)OR$^a$, N—(CH$_2$)$_y$—S(O)$_2$R$^a$, N—(CH$_2$)$_y$—S(O)$_2$OR$^a$ and N—(CH$_2$)$_y$—C(O)NR$^a$R$^a$, where y is an integer ranging from 0 to 6, wherein the heterocycloalkyl is optionally substituted with one or more groups which are each $R^f$;

each $R^d$ is, independently of the others, selected from the group consisting of $R^a$, $R^c$ and a chiral auxiliary group; and each $R^f$ is —$C_1$-$C_8$ alkoxy, —$C_1$-$C_8$ alkyl, —$C_1$-$C_6$ haloalkyl, cyano, nitro, amino, ($C_1$-$C_8$ alkyl)amino, di($C_1$-$C_8$ alkyl)amino, phenyl, benzyl, oxo, or halogen, or any two $R^f$ bonded to adjacent atoms, taken together with the atoms to which they are each attached, form a fused saturated or unsaturated cycloalkyl or a fused saturated or unsaturated heterocycloalkyl group containing 5 to 8 annular atoms, wherein the formed cycloalkyl or heterocycloalkyl group is optionally substituted with one or more groups which are each independently halogen, $C_1$-$C_8$ alkyl, or phenyl.

As can be seen from structural formula (I) the compounds described herein comprise three "main" features or moieties: (i) an optionally substituted, saturated or unsaturated, bridged or unbridged cycloalkyl ring (substituent $R^4$); (ii) an optionally substituted bicyclic heteroaryl ring (substituent "B"); and (iii) an optionally substituted aryl, heteroaryl, arylalkyl or heteroarylalkyl ring (substituent $R^2$). In various embodiments of the invention, these three main features can be combined with one another in any combination, i.e. $R^2$ and $R^4$ may be bonded to either side of the B ring, and are described in more detail below. In some preferred embodiments, the compounds of the invention have the bonding arrangement according to the formula (Ia),

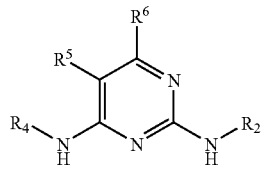

(Ia)

wherein $R^2$, $R^4$, $R^5$, and $R^6$ are as defined for formula (I).

In some embodiments, $R^5$ and $R^6$ are taken together to form an alkylene or heteroalkylene bridge selected from the group consisting of —CH=CH—CH=CH—, —N=CH—CH—, —N=CH—Y—, —CH=N—Y—, Y—N=CH—, —CH=CH—Y—, —Y—CH=CH—, and a $C_3$-$C_4$ alkylene group wherein one $CH_2$ group is optionally replaced by Y (for example, —CH$_2$CH$_2$CH$_2$—, —CH$_2$CH$_2$—Y—CH$_2$—, and —CH$_2$—Y—CH$_2$CH$_2$—) wherein Y is selected from the group consisting of O, S and NH, wherein each of the bridges is optionally substituted with 1 or 2 $R^g$, wherein each $R^g$ is independently =O, —OH, —$C_1$-$C_6$ alkoxy, ($C_1$-$C_3$) haloalkyloxy, —NR$^c$R$^c$, halogen, —$C_1$-$C_3$alkyl, —$C_1$-$C_3$haloalkyl, —CN, —NO$_2$, —S(O)$_2$R$^a$, —S(O)$_2$OR$^a$, —S(O)$_2$NR$^c$R$^c$, —OS(O)$_2$R$^a$, —OS(O)$_2$OR$^a$, —OS(O)$_2$NR$^c$ R$^c$, —C(O)R$^a$, —C(O)OR$^a$, —C(O)NR$^c$R$^c$, —C(O)NR$^a$OR$^a$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NR$^a$)NR$^c$R$^c$; aryl, or ($C_7$-$C_{20}$) arylalkyl. Preferably, each $R^g$ is independently =O, —OH, —$C_1$-$C_6$ alkoxy, ($C_1$-$C_3$) haloalkyloxy, —NR$^c$R$^c$, halogen, —$C_1$-$C_3$alkyl, —$C_1$-$C_3$haloalkyl, —CN, —NO$_2$, —S(O)$_2$R$^a$, —S(O)$_2$NR$^c$R$^c$, —C(O)R$^a$, —C(O)OR$^a$, —C(O)NR$^c$R$^c$, phenyl, or benzyl.

Specific exemplary embodiments of bicyclic heteroaryl groups according to structural formula (B.1) include groups selected from the group consisting of

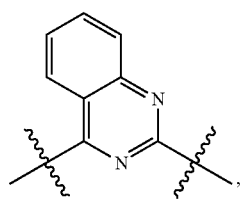

(B.1a)

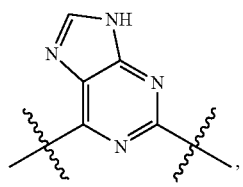

(B.1b)

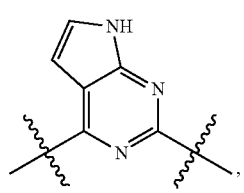

(B.1c)

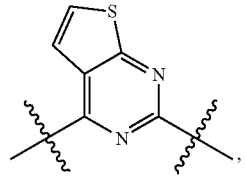

(B.1d)

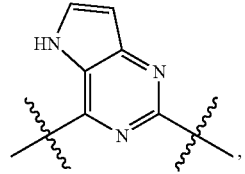

(B.1e)

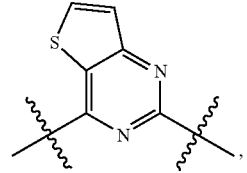

(B.1f)

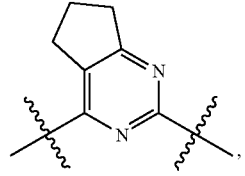

(B.1g)

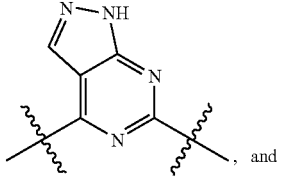

(B.1h)

, and

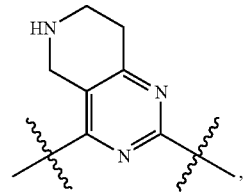

(B.1i)

wherein each of the preceding groups are optionally substituted with 1 or 2 $R^g$.

The $R^2$ substituent or moiety can comprise virtually any substituted or unsubstituted aryl, heteroaryl, arylalkyl or heteroarylalkyl group. Moreover, the nature of any present optional substituents can vary widely. Many 2,4-pyrimidinediamine compounds having optionally substituted aryl, heteroaryl, arylalkyl and heteroarylalkyl $R^2$ substituent groups that exhibit biological activity have been reported in the literature. All of these $R^2$ substituents are expected to be useful in the compounds described herein.

In some embodiments, the $R^2$ moiety is a substituted aryl, heteroaryl, arylalkyl or heteroaryl group in which at least one of the substituents is a water-solubilizing group. Such water-solubilizing groups are especially useful when the $R^2$ moiety has significant hydrophobic character, such as when $R^2$ is an aryl, for example phenyl or naphthyl, or an arylalkyl, for example benzyl.

As used herein, a "water-solubilizing" group is a group that has hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups (e.g., O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2OR^a$, N—$(CH_2)_y$—$C(O)NR^aR^a$, etc., where $R^a$ and y are as previously defined for structural formula (I)).

In some embodiments, the water-solubilizing group is a cycloheteroalkyl that optionally includes from 1 to 5 substituents, which may themselves be water-solubilizing groups.

In a specific embodiment, the water-solubilizing group is of the formula

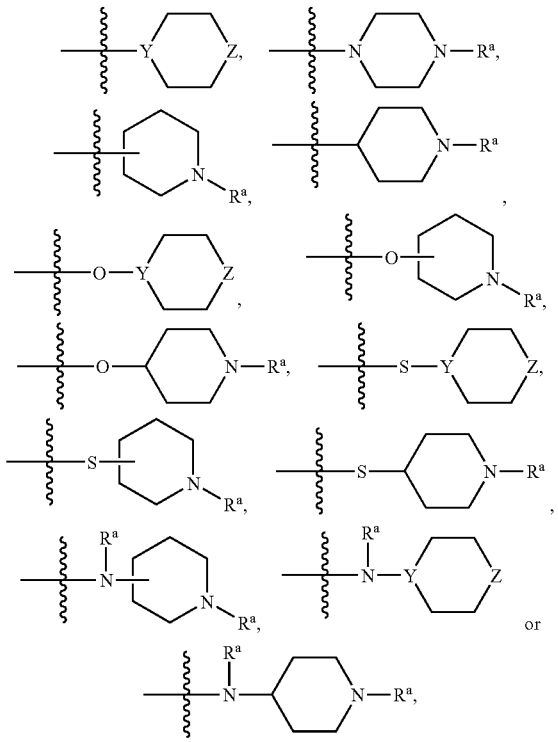

where Y is selected from the group consisting of CH and N, Z is selected from the group consisting of —$C(H(R^a))$—, —$CH_2$—, —O—, —S—, —N=, =N—, —NH—, —N(—$(CH_2)_y$—$R^a$)—, —N(—$(CH_2)_y$—$C(O)R^a$)—, —N(—$(CH_2)_y$—$C(O)OR^a$)—, —N(—$(CH_2)_y$—$S(O)_2R^a$)—, —N(—$(CH_2)_y$—$S(O)_2OR^a$)— and —N(—$(CH_2)_y$—$C(O)NR^cR^c$)—, where $R^a$, $R^c$ and y are as previously defined for structural formula (I), with the proviso that Y and Z are not both simultaneously CH and $CH_2$, respectively.

In another specific embodiment, the water-solubilizing group is selected from the group consisting of morpholino, piperidinyl, ($C_1$-$C_6$) N-alkyl piperidinyl, N-methyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, ($C_1$-$C_6$) N-alkylpiperazinyl, N-methylpiperazinyl, N-ethyl piperidinyl, N-ethyl piperazinyl, N-cycloalkyl piperazinyl, N-cyclohexyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, imidazolyl, and the like.

In a specific embodiment of the compounds described herein, $R^2$ is a substituted phenyl of the formula:

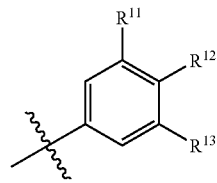

where one of $R^{11}$, $R^{12}$ or $R^{13}$ is a water-solubilizing group, and the other two of $R^{11}$, $R^{12}$ and $R^{13}$ are each, independently of one another, selected from the group consisting of hydrogen, $C_1$-$C_8$ alkyl, ($C_1$-$C_3$) alkyl, methyl, halo, chloro, fluoro, hydroxy, ($C_1$-$C_3$) hydroxyalkyl, —$O(CH_2)_x$—$R^b$, —$NR^cR^c$, —$C(O)NR^cR^c$, —$C(O)NHR^a$ and —$C(O)NHCH_3$, where $R^a$, $R^b$, $R^c$, and x are as previously defined for structural formula (I). In a specific exemplary embodiment, $R^{11}$ is hydrogen; $R^{12}$ is the water-solubilizing group, preferably selected from the group consisting of one of the specific embodiments of water-solubilizing groups described above; and $R^{12}$ is selected from the group consisting of methyl, halo, chloro, fluoro, ($C_1$-$C_3$) alkoxy, —$CH_2OR^e$ and —$C(O)NHR^e$, where $R^e$ is selected from the group consisting of hydrogen, methyl and ($C_1$-$C_3$) alkyl.

In another specific exemplary embodiment, $R^{11}$ is selected from the group consisting of hydrogen, $C_1$-$C_8$ alkyl, —$(CH_2)_n$—OH, —$OR^a$, —$O(CH_2)_n$—$R^a$, —$O(CH_2)_nR^b$, —$C(O)OR^a$, halo, —$CF_3$ and —$OCF_3$; and $R^{12}$ and $R^{13}$ are each, independently of one another, selected from the group consisting of hydrogen, $C_1$-$C_8$ alkyl, —$OR^a$, —$O(CH_2)_x$—$R^a$, —O—$(CH_2)_x$—$R^b$, —NH—$C(O)R^a$, halo, —$CF_3$,

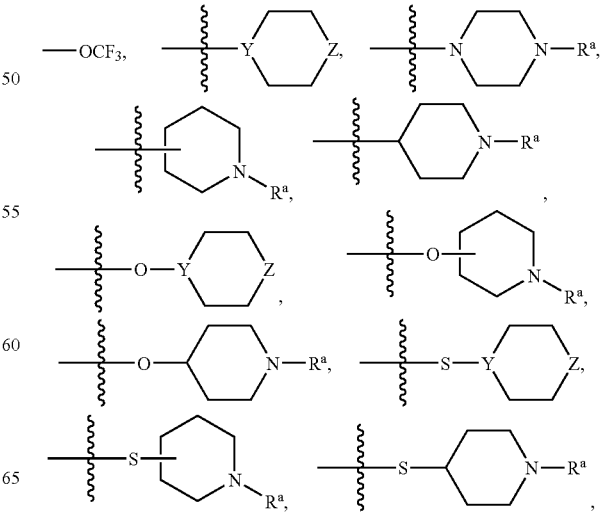

-continued

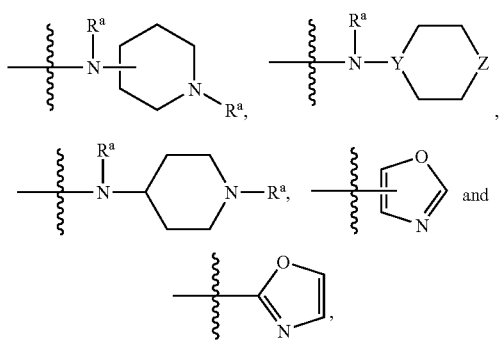

where $R^a$, $R^b$, $R^c$, and x are as previously defined for structural formula (I) and Y and Z are as defined supra.

In a specific embodiment, $R^{11}$ is hydrogen; $R^{12}$ is selected from the group consisting

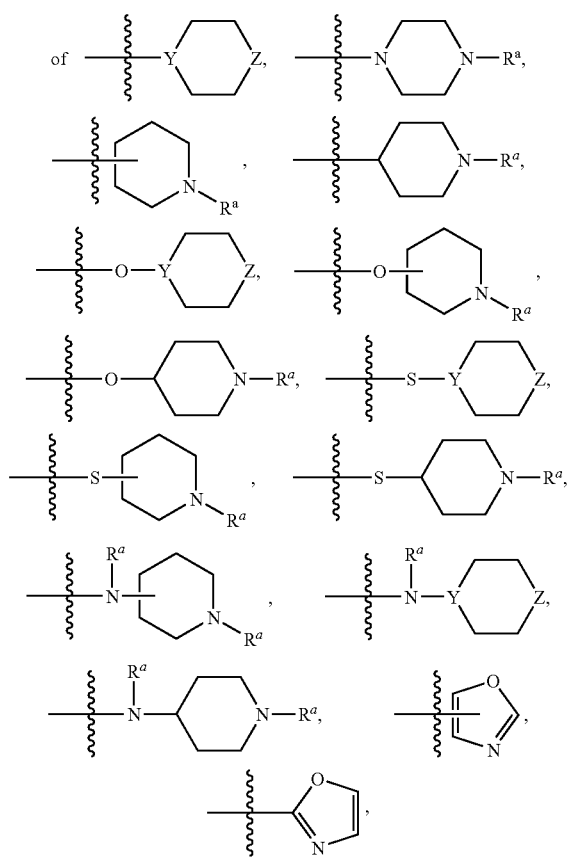

morpholino, piperidinyl, ($C_1$-$C_3$) N-alkyl piperidinyl, N-methyl piperidinyl, piperazinyl, ($C_1$-$C_3$) N-alkylpiperazinyl, N-methylpiperazinyl, N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazolyl; and $R^{13}$ is other than

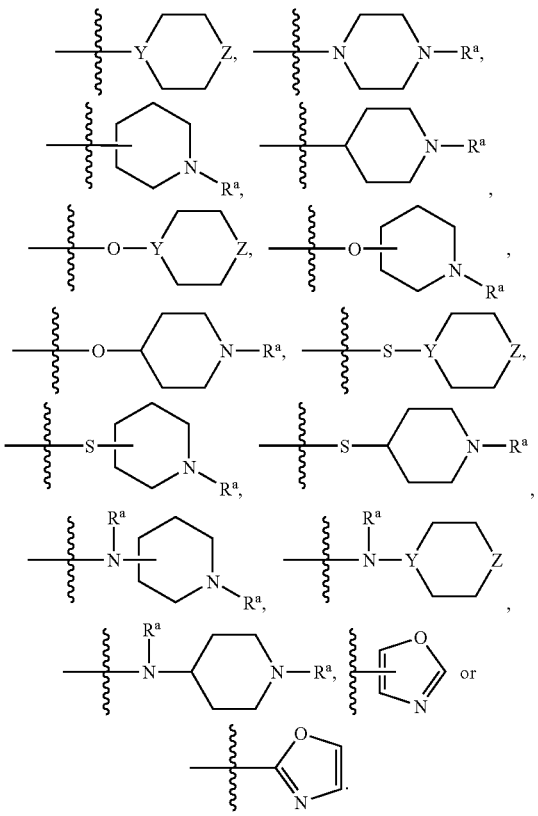

In another specific embodiment, $R^{11}$ is hydrogen; $R^{12}$ is selected from the group consisting of

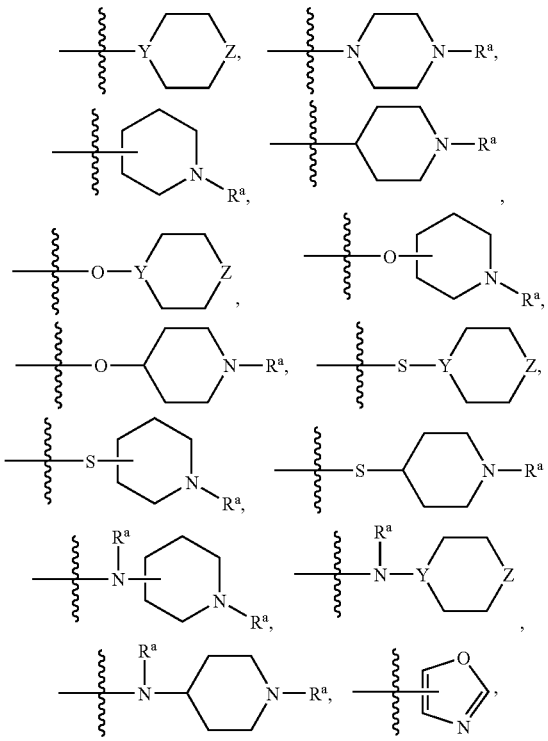

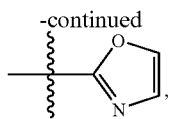

morpholino, piperidinyl, ($C_1$-$C_3$) N-alkyl piperidinyl, N-methyl piperidinyl, piperazinyl, ($C_1$-$C_3$) N-alkylpiperazinyl, N-methylpiperazinyl, N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazolyl; and $R^{13}$ is selected from the group consisting of hydrogen, methyl, methoxy, trifluoromethyl, and chloro.

In still another specific embodiment, $R^{11}$ is hydrogen; $R^{12}$ is other than,

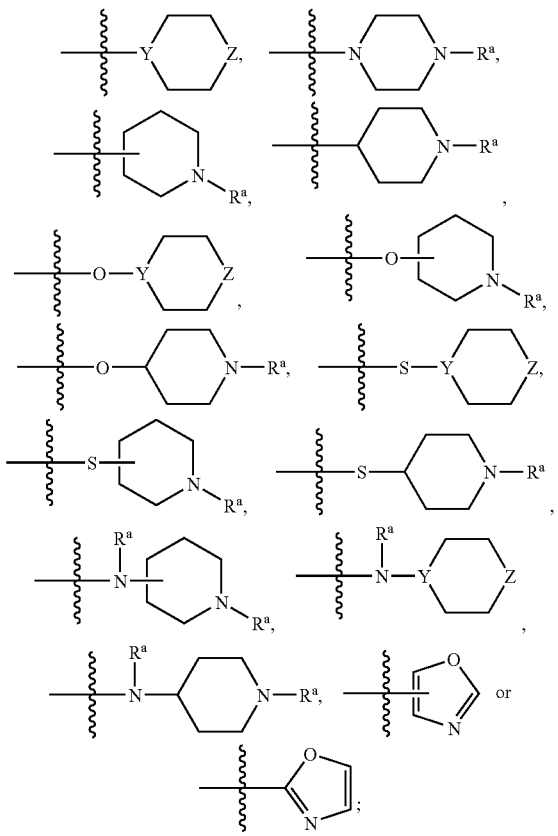

and $R^{13}$ selected from the group consisting of

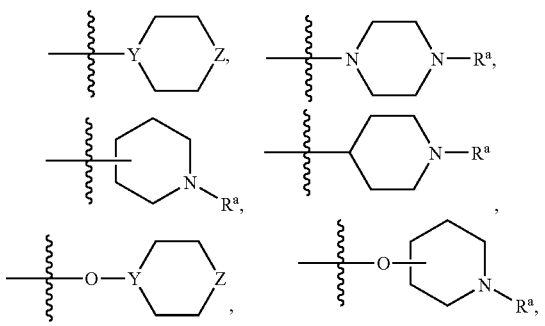

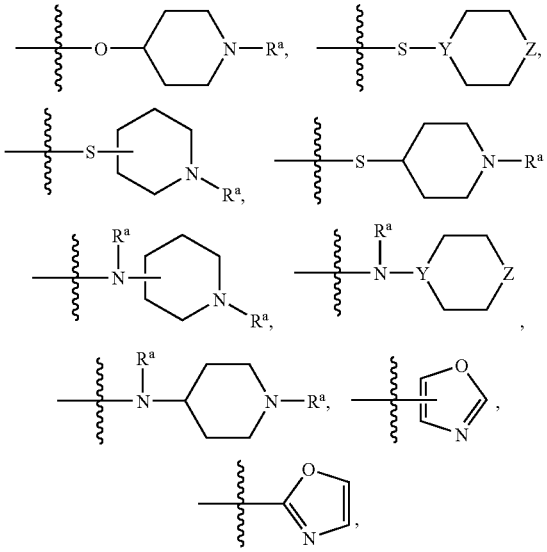

morpholino, piperidinyl, ($C_1$-$C_3$) N-alkyl piperidinyl, N-methyl piperidinyl, piperazinyl, ($C_1$-$C_3$) N-alkylpiperazinyl, N-methylpiperazinyl, N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazolyl.

In still another specific embodiment, $R^{11}$ is hydrogen; and $R^{12}$ and $R^{13}$ are each other than

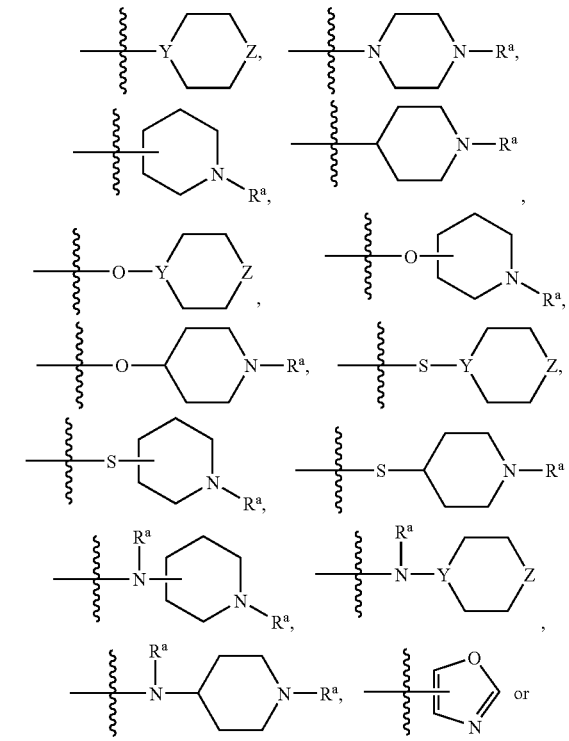

-continued

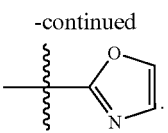

In still another specific embodiment, $R^{11}$ and $R^{12}$ are each hydrogen and $R^{13}$ is —OCH$_2$NHR$^a$.

In still other embodiments, $R^{11}$, $R^{12}$ and $R^{13}$ are each, independently of one another, selected from the group consisting of hydrogen, methyl, methoxy, trifluoromethyl and chloro, with the proviso that at least two of $R^{11}$, $R^{12}$ and $R^{13}$ are other than hydrogen. In a specific embodiment, $R^{11}$, $F^{12}$ and $R^{14}$ are each methoxy.

In still other embodiments, $R^{11}$ is hydrogen; $R^{12}$ is selected from the group consisting of hydrogen,

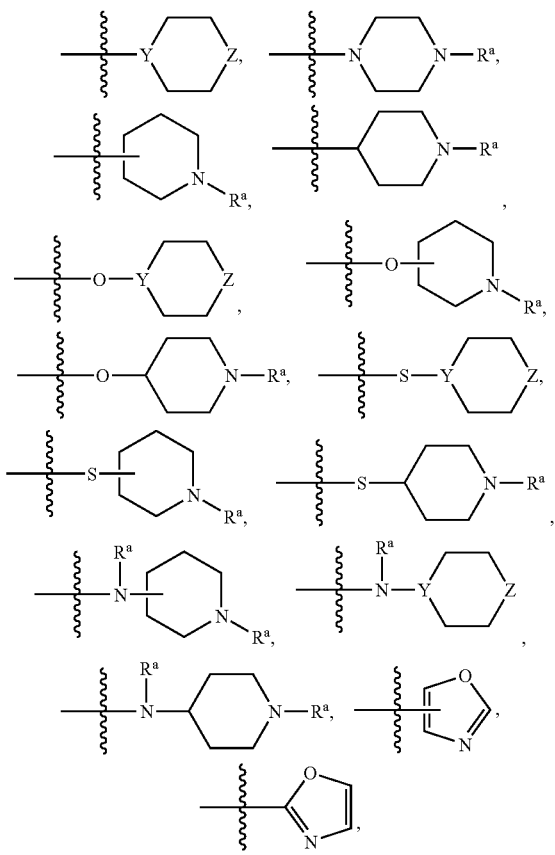

morpholino, piperidinyl, (C$_1$-C$_3$) N-alkyl piperidinyl, N-methyl piperidinyl, piperazinyl, (C$_1$-C$_3$) N-alkylpiperazinyl and N-methylpiperazinyl N-ethyl piperidinyl, N-ethyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl and imidazolyl; and $R^{13}$ is selected from the group consisting of hydrogen, C$_1$-C$_8$ alkyl, halo and —CF$_3$. In a specific embodiment, $R^{13}$ is selected from the group consisting of the hydrogen, methyl, chloro and —CF$_3$.

In yet another specific embodiment, $R^{11}$ is hydrogen; $R^{12}$ is hydrogen; and $R^{13}$ is selected from

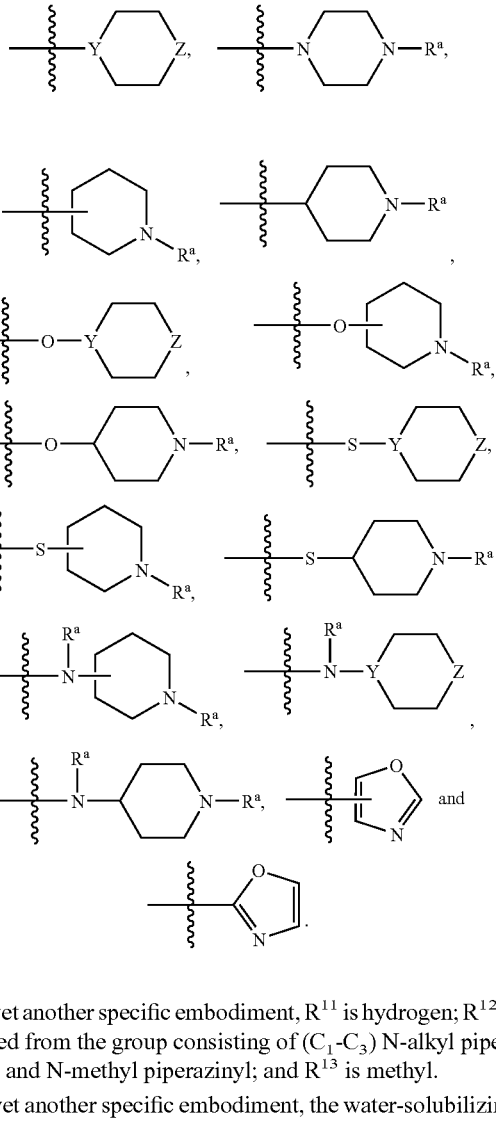

In yet another specific embodiment, $R^{11}$ is hydrogen; $R^{12}$ is selected from the group consisting of (C$_1$-C$_3$) N-alkyl piperazinyl and N-methyl piperazinyl; and $R^{13}$ is methyl.

In yet another specific embodiment, the water-solubilizing group is of the formula

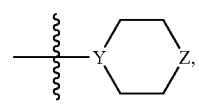

where Y is selected from the group consisting of CH and N, Z is selected from the group consisting of CH(R$^a$), CH$_2$, O, S, N, NH, N—(CH$_2$)$_y$—R$^a$, N—(CH$_2$)$_y$—C(O)R$^a$, N—(CH$_2$)$_y$—C(O)OR$^a$, N—(CH$_2$)$_y$—S(O)$_2$R$^a$, N—(CH$_2$)$_y$—S(O)$_2$OR$^a$ and N—(CH$_2$)$_y$—C(O)NR$^c$R$^c$, where R$^a$, R$^c$ and y are as previously defined for structural formula (I), with the proviso that Y and Z are not both simultaneously CH and CH$_2$, respectively. Preferably, Z is N or Y is CH(R$^a$). More preferably, Z is N and Y is CH(R$^a$). Even more preferably, Z is N and Y is CH(R$^{a1}$), wherein R$^{a1}$ is —NR$^c$R$^c$.

In yet another specific embodiment, one of $R^{11}$, $R^{12}$, and $R^{13}$ is the water-solubilizing group is of the formula

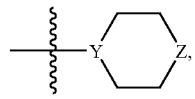

where Y is selected from the group consisting of CH and N, Z is selected from the group consisting of $CH(R^a)$, $CH_2$, O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y S(O)_2 OR^a$ and N—$(CH_2)_y$—$C(O)NR^cR^c$, where $R^a$, $R^c$ and y are as previously defined for structural formula (I), with the proviso that Y and Z are not both simultaneously CH and $CH_2$, respectively. Preferably, Z is N or Y is $CH(R^a)$. More preferably, Z is N and Y is $CH(R^a)$. Even more preferably, Z is N and Y is $CH(R^{a1})$, wherein $R^{a1}$ is —$NR^cR^c$.

In yet another specific embodiment, one of $R^{11}$, $R^{12}$, and $R^{13}$ is the water-solubilizing group is of the formula

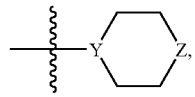

where Y is selected from the group consisting of CH and N, Z is selected from the group consisting of $CH(R^a)$, $CH_2$, O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2 OR^a$ and N—$(CH_2)_y$—$C(O)NR^cR^c$, where $R^a$, $R^c$ and y are as previously defined for structural formula (I), with the proviso that Y and Z are not both simultaneously CH and $CH_2$, respectively; and the other two are hydrogen and halogen respectively. Preferably, the other two are hydrogen and fluoro. More preferably, $R^{12}$ is the water-solubilizing group, $R^{11}$ is hydrogen, and $R^{13}$ is fluoro. Alternatively, $R^{11}$ is the water-solubilizing group, $R^{13}$ is hydrogen, and $R^{12}$ is fluoro.

In yet another specific embodiment, the water-solubilizing group is of the formula, —$O(CH_2)_x$—$NR^cR^c$, wherein x is 1 to 6. Preferably, x is 1 to 4 and $NR^cR^c$ is a nitrogen-containing heterocycloalkyl group containing 3 to 8 ring atoms, optionally containing a second heteroatomic group selected from the group consisting of $NR^a$, S, and O. More preferably, x is 1 to 3 and $NR^cR^c$ is a nitrogen-containing heterocycloalkyl group containing 3 to 8 ring atoms, optionally containing a second heteroatomic group selected from the group consisting of $NR^a$, S, and O. Even more preferably, x is 1 to 3 and $NR^cR^c$ is a nitrogen-containing heterocycloalkyl group containing 5 to 6 ring atoms, optionally containing a second heteroatomic group selected from the group consisting of $NR^a$, S, and O.

In yet another specific embodiment, one of $R^{11}$, $R^{12}$, and $R^{13}$ is the water-solubilizing group is of the formula, —$O(CH_2)_x$—$NR^cR^c$, wherein x is 1 to 6. Preferably, x is 1 to 4 and $NR^cR^c$ is a nitrogen-containing heterocycloalkyl group containing 3 to 8 ring atoms, optionally containing a second heteroatomic group selected from the group consisting of $NR^a$, S, and O; and the other two are hydrogen and halogen respectively. More preferably, x is 1 to 3 and $NR^cR^c$ is a nitrogen-containing heterocycloalkyl group containing 3 to 8 ring atoms, optionally containing a second heteroatomic group selected from the group consisting of $NR^a$, S, and O. Even more preferably, x is 1 to 3 and $NR^cR^c$ is a nitrogen-containing heterocycloalkyl group containing 5 to 6 ring atoms, optionally containing a second heteroatomic group selected from the group consisting of $NR^a$, S, and O.

In yet another specific embodiment, one of $R^{11}$, $R^{12}$, and $R^{13}$ is the water-solubilizing group is of the formula, —$O(CH_2)_x$—$NR^cR^c$, wherein x is 1 to 6. Preferably, x is 1 to 4 and $NR^cR^c$ is a nitrogen-containing heterocycloalkyl group containing 3 to 8 ring atoms, optionally containing a second heteroatomic group selected from the group consisting of $NR^a$, S, and O. More preferably, x is 1 to 3 and $NR^cR^c$ is a nitrogen-containing heterocycloalkyl group containing 3 to 8 ring atoms, optionally containing a second heteroatomic group selected from the group consisting of $NR^a$, S, and O. Even more preferably, x is 1 to 3 and $NR^cR^c$ is a nitrogen-containing heterocycloalkyl group containing 5 to 6 ring atoms, optionally containing a second heteroatomic group selected from the group consisting of $NR^a$, S, and O. Preferably, the other two are hydrogen and fluoro. More preferably, $R^{12}$ is the water-solubilizing group, $R^{11}$ is hydrogen, and $R^{13}$ is fluoro. Alternatively, $R^{11}$ is the water-solubilizing group, $R^{13}$ is hydrogen, and $R^{12}$ is fluoro.

In some other exemplary embodiments, $R^2$ is an optionally substituted heteroaryl group, optionally substituted with one or more group selected from the group consisting of $R^a$ and $R^b$. Preferably, $R^2$ is heteroaryl, optionally substituted with one or more $R^h$, wherein each $R^h$ is independently =O, —OH, —$C_1$-$C_6$ alkoxy, —$C_1$-$C_3$alkyl, ($C_1$-$C_3$) haloalkyloxy, —$NR^cR^c$, halogen, —$C_1$-$C_3$haloalkyl, —CN, —$NO_2$, —$S(O)_2R^a$, —$S(O)_2OR^a$, —$S(O)_2NR^cR^c$, —$C(O)R^a$, —$C(O)OR^a$, —$C(O)NR^cR^c$, aryl, or ($C_7$-$C_{20}$) arylalkyl.

In a specific exemplary embodiment, $R^2$ is selected from the group consisting of

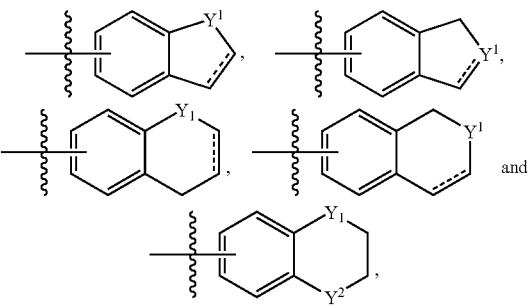

where $Y^1$ is selected from the group consisting of O, S, S(O), $S(O)_2$, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2OR^a$ and N—$(CH_2)_y$—$C(O)NR^cR^c$, where $R^a$, $R^c$ and y are as previously defined, $Y^2$ is selected from the group consisting of O, S and $S(O)_2$, and the bonds including the dotted line can be single bonds or double bonds, wherein each of the preceding groups is substituted with one or two $R^h$.

In another embodiment, $R^2$ is a phenyl mono-, di- or tri-substituted with the same or different $R^8$ groups, where $R^8$ is as previously defined for structural formula (I) and subject to the above provisos. When the phenyl is mono-substituted, the $R^8$ substituent may be positioned at either the ortho, meta or para position. When positioned at the ortho, meta or para position, $R^8$ is preferably selected from the group consisting of ($C_1$-$C_{10}$) alkyl, ($C_1$-$C_{10}$) branched alkyl, —$OR^a$ optionally substituted with one or more of the same or different $R^b$ groups, —O—$C(O)OR^a$, —$(CH_2)_m$—$C(O)OR^a$, —C(O)

$OR^a$, $-O-(CH_2)_m-NR^cR^c$, $-O-C(O)NR^cR^c$, $-O-(CH_2)_m-C(O)NR^cR^c$, $-O-C(NH)NR^cR^c$, $-O-(CH_2)_m-C(NH)NR^cR^c$ and $-NH-(CH_2)_m-NR^cR^c$, where m, $R^a$ and $R_c$, are as previously defined for structural formula (I).

In one embodiment of these compounds, each $R^a$ is independently a ($C_1$-$C_6$) alkyl and/or each $-NR^cR^c$ is $-NHR^a$, where $R^a$ is a ($C_1$-$C_6$) alkyl. In one specific embodiment, $R^8$ is $-O-CH_2-C(O)NHCH_3$. In another specific embodiment $R^8$ is $-OH$.

When the phenyl is di-substituted or tri-substituted, the $R^8$ substituents may be positioned at any combination of positions. For example, the $R^8$ substituents may be positioned at the 2,3-, 2,4-, 2,5-, 2,6-, 3,4-, 3,5-, 2,3,4-, 2,3,5-, 2,3,6-, 2,5,6- or 3,4,5-positions. In one embodiment of compounds including a disubstituted phenyl, the substituents are positioned other than 3,4-. In another embodiment they are positioned 3,4-. In one embodiment of compounds including the tri-substituted phenyl, the substituents are positioned other than 3,4,5- or, alternatively, no two of the substituents are positioned 3,4-. In another embodiments, the substituents are positioned 3,4,5-.

Specific examples of $R^8$ substituents in such di- and tri-substituted phenyls include the various $R^8$ substituents described above in connection with the ortho, meta and para substituted phenyls.

In another specific embodiment, $R^8$ substituents useful for substituting such di- and tri-substituted phenyls include ($C_1$-$C_6$) alkyl, ($C_1$-$C_6$) alkoxy, methoxy, halo, chloro, ($C_1$-$C_6$) perhaloalkyl, $-CF_3$, ($C_1$-$C_6$) perhaloalkoxy and $-OCF_3$. In a preferred embodiment, such $R^8$ substituents are positioned 3,4- or 3,5-.

While not intending to be bound by any theory of operation, it is believed that the biological activity of the compounds described herein, such as their ability to inhibit kinases, including JAK kinases, derives in large part from the $R^4$ moiety, although $R^2$ is also believed to be important for selectivity, but to a lesser extent. In many embodiments of the compounds described herein, the $R^4$ group is a saturated or unsaturated, bridged or unbridged cycloalkyl that includes an $R^7$ substituent at one of the carbon atoms. The R substituent can be attached to any carbon atom, but in specific embodiments is attached to the carbon atom connecting the $R^4$ group to the N4-nitrogen atom, the carbon atom adjacent to this carbon atom, or its next-nearest neighbor.

When the $R^4$ group in the compounds of structural formula (I) comprises an unbridged cycloalkyl, it will typically contain from 3 to 8 carbon atoms. When the unbridged cycloalkyl is unsaturated, the ring may include one, two or more double bonds, which may be positioned at any ring positions, but are most commonly positioned such that they do not include the carbon atom attaching the $R^4$ ring to the remainder of the molecule. In many embodiments, saturated rings and unsaturated rings including a single double bond are preferred. Specific examples of $R^4$ groups that comprise an unbridged saturated, or singly unsaturated, cycloalkyl ring include, but are not limited to,

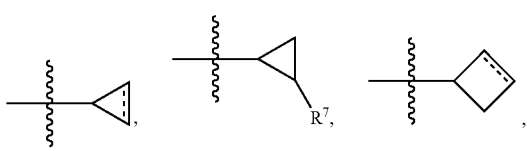

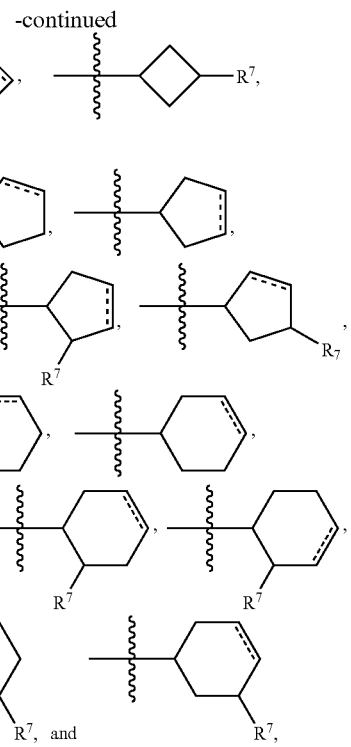

where $R^7$ is as previously defined for structural formula (I) and the dotted lines represent a single bond or a double bond.

When the $R^4$ group comprises a bridged cycloalkyl, it will typically contain from 5 to 16 carbon atoms. When the bridged cycloalkyl is unsaturated, it may include one, two or more double bonds, which may be positioned at any ring positions, but are most commonly positioned so that they do not include the carbon atom attaching the $R^4$ ring to the remainder of the molecule, or a bridgehead carbon atom. In many embodiments, of unsaturated bridged cycloalkyls, those including a single double bond are preferred. Specific examples of $R^4$ groups that comprise a bridged cycloalkyl ring include, but are not limited to,

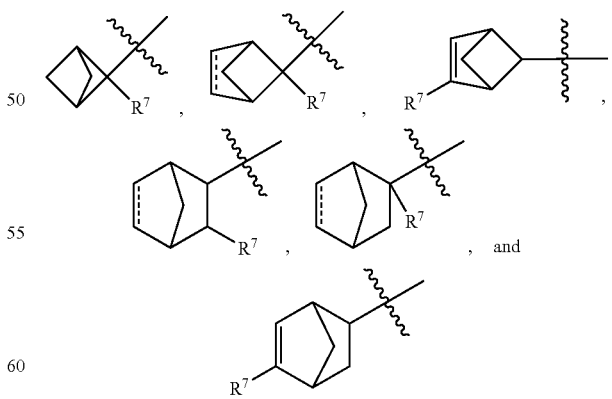

where $R^7$ is as previously defined for structural formula (I) and the dotted lines represent a single bond or a double bond.

In some embodiments, $R^7$ is an amide of the formula $-C(O)NHR^d$ or an ester of the formula $-C(O)OR^d$, where $R^d$ is as previously described for structural formula (I). In some embodiments, $R^d$ is hydrogen. In some embodiments, $R^d$ is $C_1$-$C_8$ alkyl. In some embodiments, $R^d$ is a chiral auxiliary group. Examples of suitable chiral auxiliary groups include, but are not limited to;

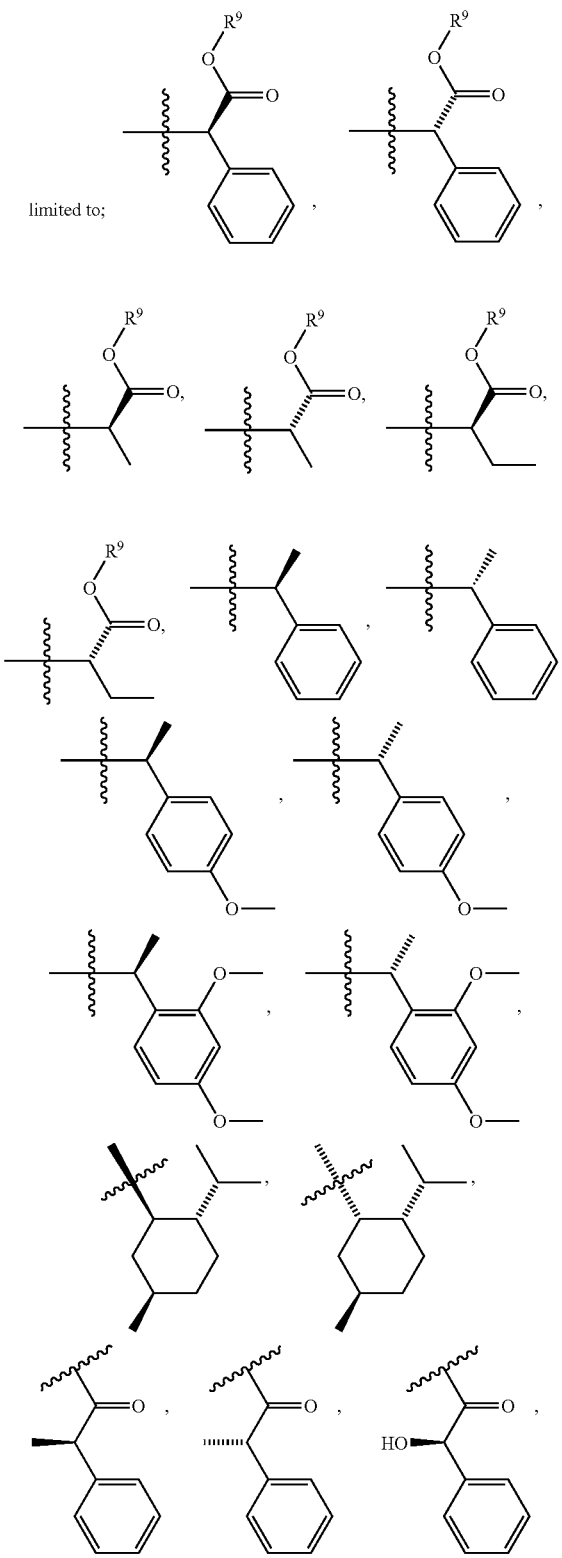

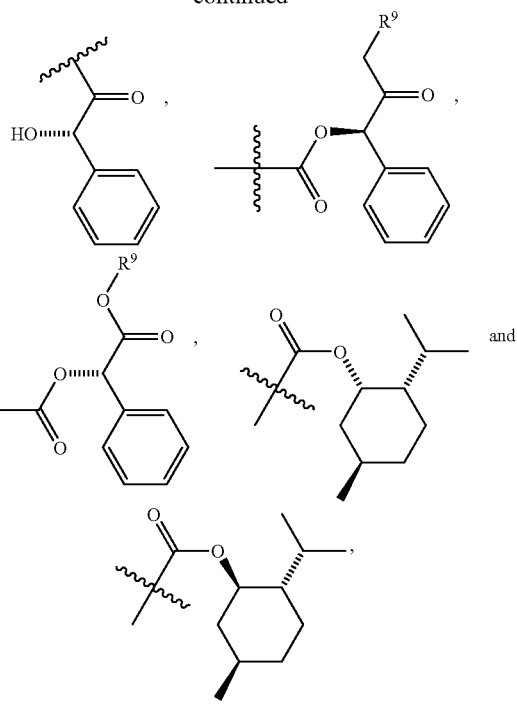

where $R^9$ is selected from the group consisting of hydrogen and $C_1$-$C_8$ alkyl (e.g. methyl, ethyl, isopropyl, cyclopropyl, $CH_2$-cyclopropyl, cyclobutyl, —$CH_2$-cyclobutyl, etc).

In still other embodiments, $R^7$ is an amide of the formula —C(O)NR$^c$R$^c$ where R$^c$ is as previously defined for structural formula (I). In yet other embodiments, $R^7$ is an amide of the formula —C(O)NHR$^a$, where R$^a$ is as previously defined for structural formula (I). In a specific embodiment, R$^a$ is hydrogen.

4.3 Stereoisomerically Enriched and Stereoisomerically Pure Compounds

As will be appreciated by skilled artisans, in many embodiments of the compounds described herein, the $R^4$ group includes chiral centers. For example, embodiments of compounds in which $R^4$ is an unbridged cycloalkyl substituted at the carbon atom adjacent to the carbon atom attaching the $R^4$ group to the remainder of the molecule includes two chiral carbon atoms: the carbon atom attaching the $R^4$ group to the remainder of the molecule, and the carbon atom including the $R^7$ substituent. Such compounds include two racemates, a cis racemate and a trans racemate, that together comprise four diastereomers, represented by structural formulae (IIa)-(IId), below (absolute configuration assignments determined assuming $R^7$ is an ester or amide group, and $R^7$ resides on carbon two of the cycloalkyl ring, the pyrimidine 4-nitrogen resides on carbon one of the cycloalkyl ring):

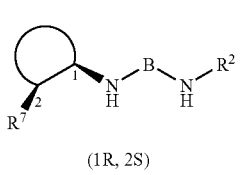

(IIa)

(1R, 2S)

-continued

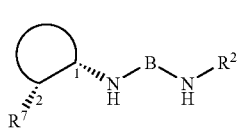

(IIb)

(1S, 2R)

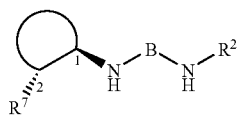

(IIc)

(1R, 2R)

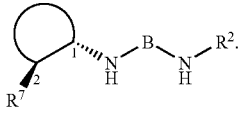

(IId)

(1S, 2S)

In structures (IIa)-(IId), the illustrated ring including the $R^7$ substituent could be any lower unbridged, saturated or unsaturated cycloalkyl ring, such as one of the exemplary rings illustrated previously. Moreover, while the $R^7$ substituent is illustrated at a specific location, it could be other locations.

For a specific 2,4 pyrimidinediamine compound, N4-(2-aminocarbonylcyclopent-1-yl)-5-fluoro-N2-[4-(4-methylpiperazin-1-yl)-3-methylphenyl]-2,4-pyrimidinediamine, it has been discovered that the trans (1R,2R) diastereomer and the two cis diastereomers, cis (1S,2R) and cis (1R,2S) inhibit the proliferation of a variety of tumor cell lines in in vitro assays, whereas the trans (1S,2S) diastereomer is relatively inactive in this same assay (see, e.g., application Ser. No. 11/133,419 filed May 18, 2005, and international application No. PCT/US05/17470 filed May 18, 2005). Based on the activity of this compound, it is expected that the various diastereomers of all of the compounds described herein that correspond in absolute configuration to the cis racemate, and the cis and trans diastereomers of structural formulae (IIa)-(IIc) will exhibit similar differences in biological activity.

Compounds in which $R^4$ is a substituted bridged cycloalkyl can include two cis racemates, exo-exo and endo-endo, represented by structural formulae (III.r1) and (III.r2), below, and two trans racemates, exo-endo and endo-exo, illustrated by structural formulae (III.r3) and (III.r4), below:

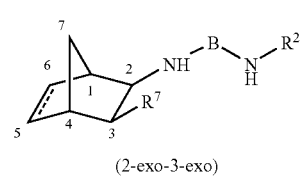

(III.r1)

(2-exo-3-exo)

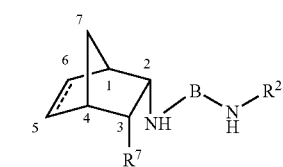

(III.r2)

(2-endo-3-endo)

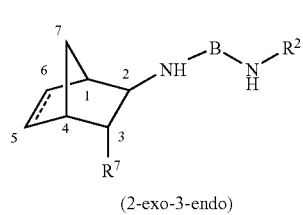

(III.r3)

(2-exo-3-endo)

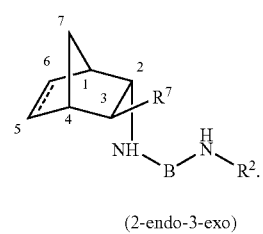

(III.r4)

(2-endo-3-exo)

Together, these four racemates comprise eight diastereomers, illustrated as structures (IVa)-(IVh), below:

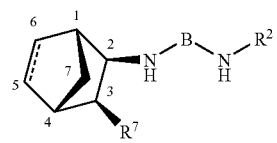

(IVa)

(1R, 2R, 3S, 4S)

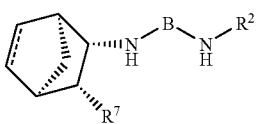

(IVb)

(1S, 2S, 3R, 4R)

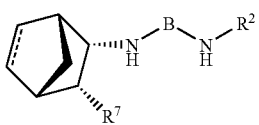

(IVc)

(1R, 2S, 3R, 4S)

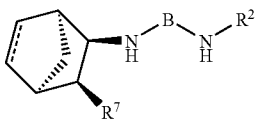

(IVd)

(1S, 2R, 3S, 4R)

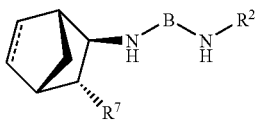

(IVe)

(1R, 2R, 3R, 4S)

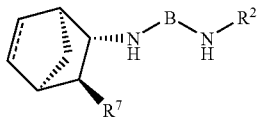

(IVf)

(1S, 2S, 3S, 4R)

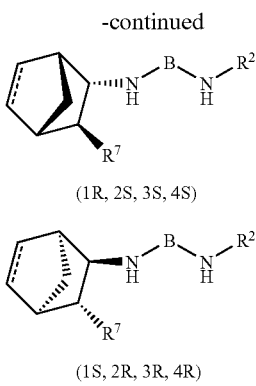

(IVg)

(1R, 2S, 3S, 4S)

(IVh)

(1S, 2R, 3R, 4R)

In structural formulae (III.r1)-(III.r4) and (IVa)-(IVh), the bond including the dotted line can be either a single bond or a double bond. It should be noted that while the racemates and diastereomers of structures (III.r1)-(III.r4) and (IVa)-(IVh) are illustrated with reference to a specific bridged $R^4$ ring, these structural diagrams are for illustrative purposes only to exemplify the absolute stereochemistry of the chiral centers with respect to one another, and are not intended to be limiting with respect to the identity of the bridged $R^4$ ring, the location of the bridge, the number of carbon atoms comprising bridge and/or the location of the $R^7$ substituent. Thus, these structures are intended to be illustrative of any bridged $R^4$ ring which includes racemates and diastereomers corresponding in stereospecific configuration to the structures of structural formulae (III.r1)-(III.r4) and (IVa)-(IVh).

In this application, the terms "exo" and "endo" are used as a matter of convenience to name compounds where $R^4$ comprises a bicyclo[2.2.1]heptane or heptene. The exo and endo nomenclature was initially developed to describe preferential attack by reagents on a double bond of bicyclo[2.2.1]heptene ring systems, which happen to have chemically distinct bridges (a —$CH_2$— bridge and a —CH=CH— bridge). For example, there are eight diastereomers represented by formulae (IVa)-(IVh), in part, because of the chirality imparted to the $R^4$ ring system by virtue of these chemically distinct bridges. When $R^4$ is a bi- or tricyclic system where the bridges are chemically distinct, then analogous racemates and diastereomers exist. Specific examples of $R^4$ rings that have such corresponding racemates and diastereomers include, but are not limited to bicyclo[2.2.1]heptane, bicyclo[2.2.1]heptene, bicyclo[2.2.2]octene, bicyclo[3.2.1]octane, bicyclo[3.2.1]octene, and the like.

For a specific 2,4-pyrimdinediamine molecule, N4-(3-aminocarbonylbicyclo [2.2.1]hept-5-en-2-yl)-5-fluoro-N2-[3-methyl-4-(4-methylpiperazin-1-yl)phenyl]-2,4-pyrimidinediamine, it has been discovered that the two cis racemates exhibit antiproliferative activity against a variety of tumor cell types in in vitro assays. However, the cis exo-exo racemate is approximately twenty-fold more potent than the cis endo-endo racemate in all cell lines tested. Moreover, it has been discovered that the enantiomer corresponding to the (1R,2R,3S,4S) diastereomer of structural formula (IVa) is largely responsible for the potency of the exo-exo cis racemate. When tested as isolated stereoisomers, the (1R,2R,3S,4S) diastereomer of this compound exhibited $IC_{50}$s in the nanomolar range, whereas the (1S,2S,3R,4R) diastereomer of this compound generally exhibited $IC_{50}$s in the micromolar range against the same cell lines. Thus, in general, the (1R,2R,3S,4S) diastereomer of this compound is approximately 1000-fold more potent than the (1S,2S,3R,4R) diastereomer.

The (1R,2R,3S,4S) diastereomer exhibited similarly superior results compared to the (1S,2S,3R,4R) diastereomers in cell-based inhibition assays against Aurora kinase B. See e.g., copending application Ser. No. 11/133,419 filed May 18, 2005, Ser. No. 11/280,066 filed Nov. 15, 2005 and Ser. No. 11/281,186 filed Nov. 15, 2005 and international application Nos. PCT/US05/017470 filed May 18, 2005, PCT/US05/041276 filed Nov. 15, 2005 and PCT/US05/041359 filed Nov. 15, 2005.

Based on the observed potency of this particular (1R,2R,3S,4S) diastereomer of this 2,4-pyrimidinediamine compound, it is expected that the diastereomers of the compounds described herein that correspond to the diastereomer of structural formula (IVa) will exhibit similarly superior potencies as compared to their enantiomers, the exo-exo and endo-endo cis racemates, and their other diastereomers.

Thus, additional specific embodiments of the compounds include compounds that are enriched in specified enantiomers and/or diastereomers.

In some embodiments, the stereoisomerically enriched compounds are compounds according to structural formula (I) in which $R^4$ comprises an unbridged saturated or unsaturated cycloalkyl that is enriched one or more of the diastereomers corresponding to structural formulae (IIa), (IIb) and/or (IIc). In a specific embodiment, the compound is substantially free of the diastereomer corresponding to structural formula (IId). In another specific embodiment, the compound is a mixture, including a racemic mixture, of the diastereomers corresponding to structural formulae (IIa) and (IIb). In still another specific embodiment, the compound is a substantially pure diastereomer corresponding to structure (IIa), (IIb) or (IIc).

In some embodiments, the stereoisomerically enriched compounds are compounds according to structural formula (I) in which $R^4$ comprises a bridged saturated or unsaturated cycloalkyl, or a saturated or unsaturated bicycloalkyl, that are enriched in a diastereomer corresponding to structural formula (IVa), (IVb), (IVc) and/or (IVd). In a specific embodiment, the compound is a racemic mixture of cis isomers corresponding to structural formulae (III.r1) or (III.r2). In another specific embodiment, the compound is substantially pure in the diastereomer corresponding to structural formula (IVa).

In one illustrative embodiment, the stereoisomerically enriched compounds are compounds according to structural formula (X):

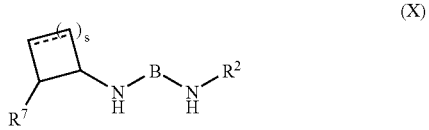

(X)

including the salts, solvates, hydrates and/or N-oxides thereof, that is enriched in one or more of the following corresponding diastereomers:

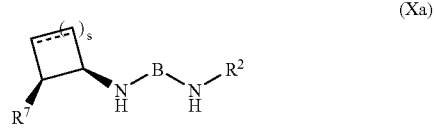

(Xa)

-continued

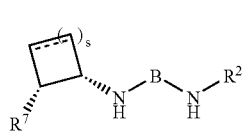
(Xb)

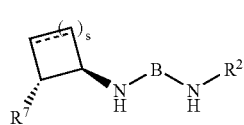
(Xc)

wherein s is an integer ranging from 0 to 5, $R^2$, B and $R^7$ are as previously defined for structural formula (I), and the dotted line represents one or more optional double bonds, the positions of which can vary, with the proviso that when S is O, the ring does not include a double bond. In a specific embodiment, S is 1, 2, 3 or 4 and the bond including the dotted line is a single bond.

In another illustrative embodiment, the stereoisomerically enriched compounds are compounds according to structural formula (XI):

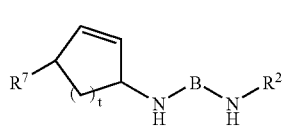
(XI)

including the salts hydrates, solvates and/or N-oxide thereof, that is enriched in one or more of the following corresponding diastereomers:

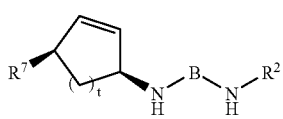
(XIa)

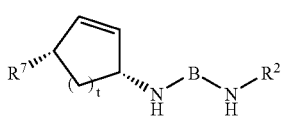
(XIb)

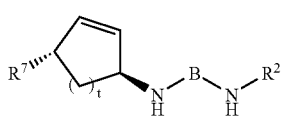
(XIc)

wherein t is an integer ranging from 1 to 3 and $R^2$, B and $R^7$ are as previously defined for structural formula (I). In a specific embodiment, t is 1 or 2.

In still another illustrative embodiment, the stereoisomerically enriched compounds are compounds according to structural formula (X) that are substantially free of the diastereomer of structural formula (Xd):

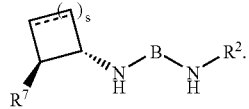
(Xd)

In still another illustrative embodiment, the stereoisomerically enriched compounds are compounds according to structural formula (XI) that are substantially free of the diastereomer of structural formula (XId):

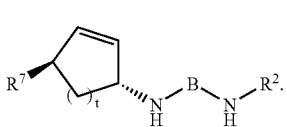
(XId)

In still another illustrative embodiment, the stereoisomerically enriched compounds are compounds according to structural formulae (Xa) and/or (XIa) that are substantially free of all other enantiomers and/or diastereomers.

In yet another illustrative embodiment, the stereoisomerically enriched compounds are compounds according to structural formula (XII):

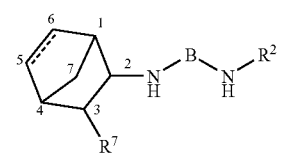
(XII)

including the salts, hydrates, solvates and/or N-oxide thereof, that are enriched in the corresponding diastereomer of structural formula (XIIa):

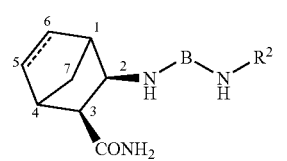
(XIIa)

wherein $R^2$, B and $R^7$ are as previously defined for structural formula (I), and the dotted line represents a single bond or double bond.

In still another illustrative embodiment, the stereoisomerically enriched compounds are compounds according to structural formula (XIIa) that are substantially free of any other enantiomers and diastereomers.

In some specific embodiments of the stereoisomerically enriched compounds described herein, $R^7$ is one of the previously defined specific embodiments and $R^2$ is a phenyl of the formula

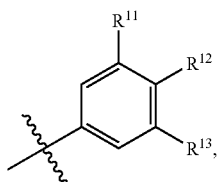

where $R^{11}$ and $R^{12}$ and $R^{13}$ are as previously defined in connection with any of the previously-discussed specific embodiments.

As used herein, a compound is "enriched" in a particular diastereomer when that diastereomer is present in excess over any other diastereomer present in the compound. The actual percentage of the particular diastereomer comprising the enriched compound will depend upon the number of other diastereomers present. As a specific example, a racemic mixture is "enriched" in a specified enantiomer when that enantiomer constitutes greater than 50% of the mixture. Regardless of the number of diastereomers present, a compound that is enriched in a particular diastereomer will typically comprise at least about 60%, 70%, 80%, 90%, or even more, of the specified diastereomer. The amount of enrichment of a particular diastereomer can be confirmed using conventional analytical methods routinely used by those of skill in the art, as will be discussed in more detail, below.

Some embodiments of stereoisomerically enriched compounds are substantially free of specified enantiomers and/or diastereomers. By "substantially free of" is meant that the compound comprises less than about 10% of the undesired diastereomers and/or enantiomers as established using conventional analytical methods routinely used by those of skill in the art (discussed in more detail below). In some embodiments, the amount of undesired stereoisomers may be less than 10%, for example, 9%, 8%, 7%, 6%, 5%, 4%, 3%, 2%, 1% or even less. Stereoisomerically enriched compounds that contain about 95% or more of a desired stereoisomer are referred to herein as "substantially pure" stereoisomers. Stereoisomerically enriched compounds that contain about 99% or more of a desired stereoisomer are referred to herein as "pure" stereoisomers. The purity of any stereoisomerically enriched compound (diastereoisomeric purity; % de) can be confirmed using conventional analytical methods, as will be described in more detail, below.

Various specific exemplary embodiments of the compounds described herein are provided in TABLE 1, in the Examples section. In this table, compounds that were either synthesized or isolated as specific diastereomers are illustrated showing the absolute stereochemistry about the chiral centers of the $R^4$ ring. Compounds having chiral centers in the $R^4$ ring that are not illustrated with a specified stereochemical configuration were synthesized as racemates.

Those of skill in the art will appreciate that the compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, compounds that include ester moieties may be considered prodrugs of their corresponding carboxylic acid, regardless of whether the ester form is pharmacologically active.

Included within the scope of the invention are prodrugs of the various compounds described herein. In such prodrugs, any available functional moiety may be masked with a progroup to yield a prodrug. Functional groups within the compounds described herein that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs described herein.

In one illustrative embodiment, the prodrugs are compounds according to structural formula (I), supra, in which $R^a$, $R^b$ and $R^c$ may be, in addition to their previously-defined alternatives, a progroup.

Those of skill in the art will appreciate that many of the compounds and prodrugs described herein, as well as the various compound species specifically described and/or illustrated herein, may exhibit the phenomena of tautomerism and conformational isomerism. For example, the compounds and prodrugs may exist in several tautomeric forms, including the enol form, the keto form and mixtures thereof. The compounds may also include chiral centers in addition to those specifically discussed herein, and may therefore exist as optical isomers. As the various compound names, formulae and compound drawings within the specification and claims can represent only one of the possible tautomeric or conformational forms, it should be understood that the invention encompasses any tautomers, conformational or optical isomers, of the compounds or prodrugs having one or more of the utilities described herein, as well as mixtures of these various different isomeric forms. In cases of limited rotation around the illustrated central bicyclic heteroaryl ring, atrop isomers are also possible and are also specifically included in the compounds and/or prodrugs of the invention.

Depending upon the nature of the various substituents, the compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, adipic acid, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

methods can be used to synthesize the compounds described herein from the corresponding dichloro bicyclic heteroaryl starting materials. Exemplary pathways and starting materials for compounds of formula (I) in which ring "B" is a variety of different bicyclic heteroaryls are illustrated in Scheme (I), below:

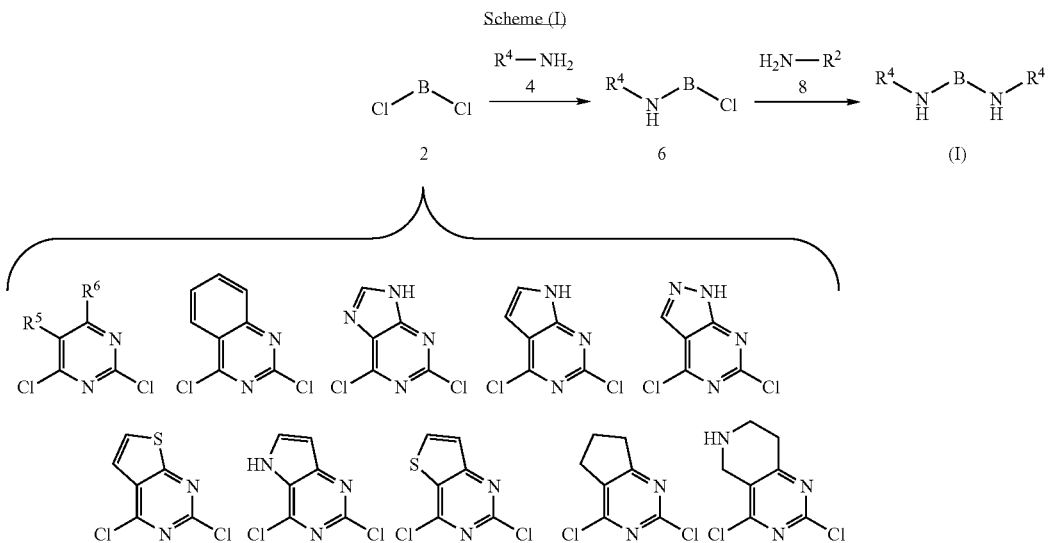

Pharmaceutically acceptable salts also include salts formed when an acidic proton present in the parent compound is either replaced by a metal ion (e.g., an alkali metal ion, an alkaline earth metal ion or an aluminum ion) or coordinates with an inorganic or organic base (e.g., ammonia, ethanolamine, diethanolamine, triethanolamine, N-methylglucamine, morpholine, piperidine, dimethylamine, diethylamine, etc.).

The compounds and prodrugs, as well as the salts thereof, may also be in the form of hydrates, solvates and/or N-oxides, as are well-known in the art.

For embodiments of compounds that are enriched in particular diastereomers, the stereoisomeric enrichment and/or purity may be established by conventional analytical methods well known to those of skill in the art. For example, use of chiral NMR shift reagents, gas chromatographic analysis using chiral columns, high pressure liquid chromatographic analysis using chiral columns, formation of diastereomeric derivatives through reaction with chiral reagents and conventional analysis may be used to establish the stereoisomeric enrichment and/or purity of a specific stereoisomer. Alternatively, synthesis using starting materials of known stereoisomeric enrichment and/or purity may be used to establish the stereoisomeric enrichment and/or purity of the compounds described herein. Other analytical methods for demonstrating stereoisomeric homogeneity are well within the ambit of the skilled artisan.

4.4 Methods of Synthesis

The compounds and prodrugs described herein may be synthesized via a variety of different synthetic routes using commercially available starting materials and/or starting materials prepared by conventional synthetic methods. A variety of routes useful for synthesizing 2,4-pyrimidinediamine compounds from 2,4-dichloropyrimidine are described in WO 03/063794 and US 2004-0029902, the disclosures of which are incorporated herein by reference. These Compounds that are enriched, substantially pure and/or pure in specified diastereomers may be isolated by chiral separation or by other standard techniques. Methods for chirally resolving specific diastereomers are described in more detail in the Examples section.

Methods of synthesizing racemic and/or steroisomerically pure amine 4 are described in detail in application Ser. No. 11/133,419 filed May 18, 2005, US Pat. Publication No. 20060035891 of Feb. 16, 2006; Ser. No. 11/280,066 filed Nov. 15, 2005, US Pat. Publication No. 20060167249 of Jul. 27, 2006; Ser. No. 11/281,186 filed Nov. 15, 2005, issued as U.S. Pat. No. 7,459,301 on Dec. 2, 2008; PCT/US05/017470 filed May 18, 2005, WIPO Publication No. WO 2005/118544 of Dec. 15, 2005; PCT/US05/041359 filed Nov. 15, 2005, WIPO Publication No. WO 2006/055561 of May 26, 2006; and PCT/US05/041276 filed Nov. 15, 2005, WIPO Publication No. WO 2006/055528 of May 26, 2006, the disclosures of which are incorporated herein by reference.

4.5 Activity of the Compounds

The compounds and/or prodrugs described herein are potent and selective inhibitors of protein kinases, especially those of the JAK family and Axl family, as demonstrated by their inhibition of this protein kinase in cellular and biochemical assays. The ability of the compounds to act in this way may be simply determined by employing tests that are well-known in the art. Specific exemplary tests that may be used are described in the Examples section.

In some embodiments, activity of a specified compound can be assessed in a cellular assay. Suitable assays include assays that determine inhibition of phosphorylation activity or ATPase activity of a specified activated kinase, such as an activated JAK kinase. A compound is said to inhibit an activity of kinase such as a JAK kinase if it inhibits phosphorylation or ATPase activity of the activated kinase with an $IC_{50}$ of about 10 ym or less. A specific assay for assessing JAK kinase activity, and in particular JAK1 and/or JAK3 kinase activity, is described in the Examples section.

4.5.1 Inhibitors of Degranulation of Immune Cells

Many of the compounds described herein are potent inhibitors of degranulation of immune cells, such as mast, basophil, neutrophil and/or eosinophil cells. Thus, in still another aspect, the present disclosure provides methods of regulating, and in particular inhibiting, degranulation of such cells. The method generally involves contacting a cell that degranulates with an amount of a suitable compound described herein, or an acceptable salt, hydrate, solvate, N-oxide, prodrug and/or composition thereof, effective to regulate or inhibit degranulation of the cell. The method may be practiced in in vitro or in in vivo as a therapeutic approach towards the treatment or prevention of diseases characterized by, caused by or associated with cellular degranulation.

While not intending to be bound by any theory of operation, biochemical data confirm that many of the compounds of the invention exert a degranulation inhibitory effect, at least in part, by blocking or inhibiting the signal transduction cascade(s) initiated by crosslinking of the high affinity Fc receptors for IgE ("FcεRI") and/or IgG ("FcγRI") Indeed, these active compounds are potent inhibitors of both FcεRI-mediated and FcγRI-mediated degranulation.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a compound described herein, or an acceptable salt, hydrate, solvent, N-oxide, prodrug and/or composition thereof, effective to regulate or inhibit the Fc receptor signaling cascade and/or a downstream process effected by the activation of this signaling cascade. The method may be practiced in in vitro or in in vivo as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present disclosure provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or a human an amount of a compound described herein, or an acceptable salt, hydrate, solvate, N-oxide, prodrug and/or composition thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods of the invention.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods described herein.

Additional diseases that can be treated or prevented according to the methods described herein include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

Many of the compounds are also potent inhibitors of the tyrosine kinase Syk kinase. Thus, in still another aspect, the present disclosure provides methods of regulating, and in particular inhibiting, Syk kinase activity. The method generally involves contacting a Syk kinase or a cell comprising a Syk kinase with an amount of a suitable compound, or an acceptable salt, hydrate, solvate, N-oxide, prodrug and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro or in in vivo as a therapeutic approach towards the treatment or prevention of diseases characterized by, caused by or associated with Syk kinase activity.

While not intending to be bound by any particular theory of operation, it is believed that such active compounds inhibit cellular degranulation and/or the release of other chemical mediators primarily by inhibiting Syk kinase that gets activated through the gamma chain homodimer of FcεRI. This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, the compounds described herein may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling (Turner et al., 2000, Immunology Today 21:148-154) and is an essential component of integrin beta(1), beta(2) and beta(3) signaling in neutrophils (Mocsai et al., 2002, Immunity 16:547-558). Active 2,4-pyrimidinediamine compounds that are potent inhibitors of Syk kinase can be used to regulate, and in particular inhibit, any signaling cascade where Syk plays a role, such as, fore example, the Fc receptor, BCR and integrin signaling cascades, as well as the cellular responses elicited through these signaling cascades. Thus, the compounds described herein can be used to regulate such activities. The particular cellular response regulated or inhibited will depend, in part, on the specific cell type and receptor signaling cascade, as is well known in the art. Non-limiting examples of cellular responses that may be regulated or inhibited with such compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present disclosure provides methods of regulating, and in particular inhibiting, signal transduction cascades in which Syk plays a role. The method generally involves contacting a Syk-dependent receptor or a cell expressing a Syk-dependent receptor with an amount of a suitable compound described herein, or an acceptable salt, hydrate, solvate, N-oxide, prodrug and/or composition thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is now known or later discovered to play a role. The methods may be practiced in in vitro or in in vivo contexts as a therapeutic approach towards the treatment or prevention of diseases characterized by, caused by or associated with activation of the Syk-dependent signal transduction cascade. Non-limited examples of such diseases include those previously discussed.

Cellular and animal data also confirm or can be used to confirm that many of these active compounds may also be used to treat or prevent autoimmune diseases and/or symptoms of such diseases. As a consequence, compounds can likewise be used to treat or prevent such autoimmune diseases and/or symptoms. The methods generally involve administering to a subject suffering from an autoimmune disease or at risk of developing an autoimmune disease an amount of a suitable compound described herein, or an acceptable salt, N-oxide, hydrate, solvate, prodrug or composition thereof, effective to treat or prevent the autoimmune disease and/or its associated symptoms. Autoimmune diseases that can be treated or prevented with the compounds include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include, but are not limited to, those autoimmune diseases that are frequently designated as single organ or single cell-type autoimmune disorders and those autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia (including immune thrombocytopenia purpura), sympathetic ophthalmia, myasthenia gravis, Graves' disease, primary biliary cirrhosis, chronic aggressive hepatitis, ulcerative colitis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid. Additional autoimmune diseases, which can be β-cell (humoral) based or T-cell based, include autoimmune alopecia, Type I or juvenile onset diabetes, and thyroiditis. Uses of the Antiproliferative Compounds As noted previously, the compounds described herein are inhibitors of protein kinases. As a consequence of their biological activities, they can be used in a variety of in vitro, in vivo and ex vivo contexts to regulate or inhibit protein kinase activity, signaling cascades in which protein kinases play a role, and the biological response affected by such signaling cascades. Many of these kinase, such as, for example, SYK kinase and Lyn kinase, are involved in the IgE receptor signaling cascade that lead to degranulation of immune cells such as mast cells, and the consequent release of mediators of inflammation. Thus, the compounds may be used to treat and/or prevent diseases that are characterized by caused by and/or associated with the release of such indicators. Such diseases include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

Many of the compounds described herein are inhibitors of JAK kinases. As a consequence of this activity, the compounds may be used in a variety of in vitro, in vivo and ex vivo contexts to regulate or inhibit JAK kinase activity, signaling cascades in which JAK kinases play a role, and the biological responses affected by such signaling cascades. For example, in one embodiment, the compounds may be used to inhibit JAK kinase, either in vitro or in vivo, in virtually any cell type expressing the JAK kinase. For example, in hematopoietic cells, in which, for example JAK3 is predominantly expressed. They may also be used to regulate signal transduction cascades in which JAK kinases, particularly JAK3, play a role. Such JAK-dependent signal transduction cascades include, but are not limited to, the signaling cascades of cytokine receptors that involve the common gamma chain, such as, for example, the IL-4, IL-7, IL-5, IL-9, IL-15 and IL-21, or IL-2, IL-4, IL-7, IL-9, IL-15 and IL-21 receptor signaling cascades. The compounds may also be used in vitro or in vivo to regulate, and in particular inhibit, cellular or biological responses affected by such JAK-dependent signal transduction cascades. Such cellular or biological responses include, but are not limited to, IL-4/ramos CD23 upregulation, IL-2 mediated T-cell proliferation, etc. Importantly, the compounds may be used to inhibit JAK kinases in vivo as a therapeutic approach towards the treatment or prevention of diseases mediated, either wholly or in part, by a JAK kinase activity (referred to herein as "JAK kinase mediated diseases"). Non-limiting examples of JAK kinase mediated diseases that may be treated or prevented with the compounds, include, but are not limited to allergies, asthma, autoimmune diseases such as transplant rejection (e.g., kidney, heart, lung, liver, pancreas, skin; host versus graft reaction (HVGR), etc.), rheumatoid arthritis, and amyotrophic lateral sclerosis, T-cell mediated autoimmune diseases such as multiple sclerosis, psoriasis and Sjogren's syndrome, Type II inflammatory diseases such as vascular inflammation (including vasculitis, arteritis, atherosclerosis and coronary artery disease), diseases of the central nervous system such as stroke, pulmonary diseases such as bronchitis obliteraus and primary pulmonary hypertension, and solid, delayed Type IV hypersensitivity reactions, and hematologic malignancies such as leukemia and lymphomas.

In a specific embodiment, the compounds can be used to treat and/or prevent rejection in organ and/or tissue transplant recipients (i.e., treat and/or prevent allorgraft rejection).

Allografts may be rejected through either a cell-mediated or humoral immune reaction of the recipient against transplant (histocompatibility) antigens present on the membranes of the donor's cells. The strongest antigens are governed by a complex of genetic loci termed human leukocyte group A (HLA) antigens. Together with the ABO blood groups antigens, they are the chief transplantation antigens detectable in humans.

Rejection following transplantation can generally be broken into three categories: hyperacute, occurring hours to days following transplantation; acute, occurring days to months following transplantation; and chronic, occurring months to years following transplantation.

Hyperacute rejection is caused mainly by the production of host antibodies that attack the graft tissue. In a hyperacute rejection reaction, antibodies are observed in the transplant vascular very soon after transplantation. Shortly thereafter, vascular clotting occurs, leading to ischemia, eventual necrosis and death. The graft infarction is unresponsive to known immunosuppressive therapies. Because HLA antigens can be identified in vitro, pre-transplant screening is used to significantly reduce hyperacute rejection. As a consequence of this screening, hyperacute rejection is relative uncommon today.

Acute rejection is thought to be mediated by the accumulation of antigen specific cells in the graft tissue. The T-cell-mediated immune reaction against these antigens (i.e., the HVGR) is the principle mechanism of acute rejection. Accumulation of these cells leads to damage of the graft tissue. It is believed that both CD4+ helper T-cells and CD8+ cytotoxic T-cells are involved in the process, and that the antigen is presented by donor and host dendritic cells. The CD4+ helper T-cells help recruit other effector cells, such as macrophages and cosinophils, to the graft. Accessing T-cell activation signal transduction cascades (for example, CD28, CD40L and CD2 cascades) are also involved.

Although the graft tissue can suffer from varying degrees of hemorrhage and edema, the vascular integrity is usually maintained, although the arterial endothelium appears to be a primary target of HVGR acute rejection.

The cell-mediated acute rejection may be reversed in many cases by intensifying immunotherapy. After successful reversal, severely damaged elements of the graft heal by fibrosis and the remainder of the graft appears normal. After resolution of acute rejection, dosages of immunosuppressive drugs can be reduced to very low levels.

Chronic rejection, which is a particular problem in renal transplants, often progresses insidiously despite increased immunosuppressive therapy. It is thought to be due, in large part, to cell-mediated Type IV hypersensitivity. The pathologic profile differs from that of acute rejection. The arterial andothelium is primarily involved, with extensive proliferation that may gradually occlude the vessel lumen, leading to ischemia, fibrosis, a thickened intima and atherosclerotic changes. Chronic rejection is mainly due to a progressive obliteration of graft vasculature, and resembles a slow, vasculitic process.

In Type IV hypersensitivity, CD8 cytotoxic T-cells and CD4 helper T cells recognize either intracellular or extracellular synthesized antigen when it is complexed, respectively, with either Class I or Class II MHC molecules. Macrophages function as antigen-presenting cells and release IL-1, which promotes proliferation of helper T-cells. Helper T-cells release interferon gamma and IL-2, which together regulate delayed hyperactivity reactions mediated by macrophage activation and immunity mediated by T cells. In the case of organ transplant, the cytotoxic T-cells destroy the graft cells on contact.

As previously discussed, compounds described herein are potent inhibitors of Syk kinase. As a consequence of these activities, these active compounds may be used in a variety of in vitro, in vivo and ex vivo contexts to regulate or inhibit Syk kinase, signaling cascades in which Syk kinase plays a role, Fc receptor signaling cascades, and the biological responses effected by such signaling cascades. For example, in one embodiment, the compounds may be used to inhibit Syk kinase, either in vitro or in vivo, in virtually any cell type expressing Syk kinase. They may also be used to regulate signal transduction cascades in which Syk kinase plays a role. Such Syk-dependent signal transduction cascades include, but are not limited to, the FcεRI, FcγRI, FcγRIII, BCR and integrin signal transduction cascades. The compounds may also be used in vitro or in vivo to regulate, and in particular inhibit, cellular or biological responses effected by such Syk-dependent signal transduction cascades. Such cellular or biological responses include, but are not limited to, respiratory burst, cellular adhesion, cellular degranulation, cell spreading, cell migration, cell aggregation, phagocytosis, cytokine synthesis and release, cell maturation and $Ca^{2+}$ flux. Importantly, the compounds may be used to inhibit Syk kinase in vivo as a therapeutic approach towards the treatment or prevention of diseases mediated, either wholly or in part, by a Syk kinase activity. Non-limiting examples of Syk kinase mediated diseases that may be treated or prevented with the compounds are those discussed in more detail, below.

In another embodiment, the compounds may be used to regulate or inhibit the Fc receptor signaling cascades and/or FcεRI- and/or FcγRI-mediated degranulation as a therapeutic approach towards the treatment or prevention of diseases characterized by, caused by and/or associated with the release or synthesis of chemical mediators of such Fc receptor signaling cascades or degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

In addition to the myriad diseases discussed above, cellular and animal empirical data confirm that Syk inhibitors are also useful for the treatment or prevention of autoimmune diseases, as well as the various symptoms associated with such diseases. Thus, Syk inhibitors of the invention are useful for treating or preventing such diseases and/or symptoms. The types of autoimmune diseases that may be treated or prevented with such prodrugs generally include those disorders involving tissue injury that occurs as a result of a humoral and/or cell-mediated response to immunogens or antigens of endogenous and/or exogenous origin. Such diseases are frequently referred to as diseases involving the nonanaphylactic (i.e., Type II, Type III and/or Type IV) hypersensitivity reactions.

Type I hypersensitivity reactions generally result from the release of pharmacologically active substances, such as histamine, from mast and/or basophil cells following contact with a specific exogenous antigen. As mentioned above, such Type I reactions play a role in numerous diseases, including allergic asthma, allergic rhinitis, etc.

Type II hypersensitivity reactions (also referred to as cytotoxic, cytolytic complement-dependent or cell-stimulating hypersensitivity reactions) result when immunoglobulins react with antigenic components of cells or tissue, or with an antigen or hapten that has become intimately coupled to cells or tissue. Diseases that are commonly associated with Type II hypersensitivity reactions include, but are not limited, to autoimmune hemolytic anemia, erythroblastosis fetalis and Goodpasture's disease.

Type III hypersensitivity reactions, (also referred to as toxic complex, soluble complex, or immune complex hypersensitivity reactions) result from the deposition of soluble circulating antigen-immunoglobulin complexes in vessels or in tissues, with accompanying acute inflammatory reactions at the site of immune complex deposition. Non-limiting examples of prototypical Type III reaction diseases include the Arthus reaction, rheumatoid arthritis, serum sickness, systemic lupus erythematosis, certain types of glomerulonephritis, multiple sclerosis and bullous pemphingoid.

Type IV hypersensitivity reactions (frequently called cellular, cell-mediated, delayed, or tuberculin-type hypersensitivity reactions) are caused by sensitized T-lymphocytes which result from contact with a specific antigen. Non-limiting examples of diseases cited as involving Type IV reactions are contact dermatitis and allograft rejection.

Autoimmune diseases associated with any of the above nonanaphylactic hypersensitivity reactions may be treated or prevented with the prodrugs according to structural formulae (I) and (Ia). In particular, the methods may be used to treat or prevent those autoimmune diseases frequently characterized as single organ or single cell-type autoimmune disorders including, but not limited to: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, as well as those autoimmune diseases frequently characterized as involving systemic autoimmune disorder, which include but are not limited to: systemic lupus erythematosis (SLE), rheumatoid arthritis, Sjogren's syndrome, Reiter's syndrome, polymyositis-dermatomyositis, systemic sclerosis, polyarteritis nodosa, multiple sclerosis and bullous pemphigoid.

It will be appreciated by skilled artisans that many of the above-listed autoimmune diseases are associated with severe symptoms, the amelioration of which provides significant therapeutic benefit even in instances where the underlying autoimmune disease may not be ameliorated. Many of these symptoms, as well as their underlying disease states, result as a consequence of activating the FcγR signaling cascade in monocyte cells. As compounds of the invention are potent inhibitors of such FcγR signaling in monocytes and other cells, the methods find use in the treatment and/or prevention of myriad adverse symptoms associated with the above-listed autoimmune diseases.

Since JAK kinases play a critical role in the activation of T-cells, the compounds described herein can be used to treat and/or prevent many aspects of transplant rejection, and are particularly useful in the treatment and/or prevention of rejection reactions that are mediated, at least in part, by T-cells, such as the HVGR. The compounds can also be used to treat and/or prevent chronic rejection in transplant recipients, and in particular in renal transplant recipients.

Many of the compounds described herein are inhibitors of Axl kinase. As a consequence of this activity, the compounds may be used in a variety of in vitro, in vivo and ex vivo contexts to regulate or inhibit Axl kinase activity, signaling cascades in which Axl kinases play a role, and the biological responses affected by such signaling cascades. Many of these kinases, such as, for example, Axl and Gas6, are involved in vasculature in both endothelial cells (ECs) and vascular smooth muscle cells (VSMCs) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. Thus, the compounds may be used to treat and/or prevent diseases that are characterized by caused by and/or associated with the release of such indicators.

Such diseases include, by way of example and not limitation, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

4.6 Combination Therapies

The compounds described herein may be used alone, in combination with one another, or as an adjunct to, or in conjunction with, other therapies established for the specific indication being treated. In some embodiments, the compounds are applied in combination with or adjunctive to other common immunosuppressive therapies, such as, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also, the prescribing information in the 2005 Edition of *The Physician's Desk Reference*), the disclosures of which are incorporated herein by reference. Azathioprine is currently available from Salix Pharmaceuticals, Inc. under the brand name AZASAN; mercaptopurine is currently available from Gate Pharmaceuticals, Inc. under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and Abbott under the brand name GENGRAF; IMPDH inhibitors such as mycophenolate mofetil and mycophenolic acid are currently available from Roche under the brand name CELLCEPT and Novartis under the brand name MYFORTIC; azathioprine is currently available from Glaxo Smith Kline under the brand name IMURAN; and antibodies are currently available from Ortho Biotech under the brand name ORTHOCLONE, Novartis under the brand name SIMULECT (basiliximab) and Roche under the brand name ZENAPAX (daclizumab).

In other embodiments, the compounds can be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few.

4.7 Formulations and Administration

The compounds may be administered per se in the form of prodrugs or as pharmaceutical compositions, comprising an active compound or prodrug. Pharmaceutical compositions comprising the active compounds (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see *Remington's Pharmaceutical Sciences*, 15th Ed., Hoover, J. E. ed., Mack Publishing Co. (2003)

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known in the art.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) or other vehicles such as CREMOPHOR (a class of non-ionic solubilizers and emulsifiers manufactured by BASF Corporation, Florham Park, N.J.), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

4.8 Effective Dosages

The active compound(s) or prodrug(s), or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as, for example, the HVGR, or the ability to prolong the time period between onset of acute rejection episodes and/or onset of chronic rejection. Therapeutic benefit also includes halting or slowing the progression of the disease, regardless of whether improvement is realized.

For prophylactic administration, the compound may be administered to a patient at risk of developing one of the previously described conditions. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

In the context of transplant rejection, the compound may be administered while the patient is not having an acute rejection reaction to avoid the onset of rejection and/or prior to the appearance of clinical indications of chronic rejection.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

As known by those of skill in the art, the preferred dosage of the compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one conditions or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in the Examples section.

Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, latest edition, supra, and the references cited therein.

Initial dosages may also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-55 11. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Suitable animal models of transplant rejection, such as models of the HVGR are described in O'Shea et al., 2004, Nature Reviews Drug Discovery 3:555-564; Cetkovic-Curlje & Tibbles, 2004, Current Pharmaceutical Design 10:1767-1784; and Chengelian et al., 2003, Science 302:875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) $LD_{50}/ED_{50}$ effect is the therapeutic index ($LD_{50}$ is the dose lethal to 50% of the population and $ED_{50}$ is the dose therapeutically effective in 50% of the population). Compounds(s) that exhibit high therapeutic indices are preferred.

4.9 Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

5. EXAMPLES

The inventions are further defined by reference to the following examples, which describe the preparation of several exemplary embodiments of the compounds described herein, methods for assaying their biological activity, and methods for their use. It will be apparent to the skilled artisan that many modifications, both to the materials and methods, may be practiced without departing from the scope of the inventions.

Example 1

Synthesis of Racemic 2-Amino-3-dimethylaminocarbonylbicyclo-[2.2.1]hept-5-ene TFA Salt 13

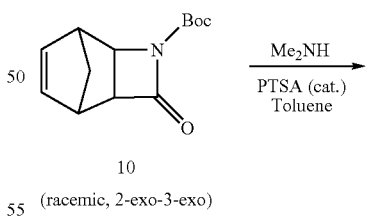

10

(racemic, 2-exo-3-exo)

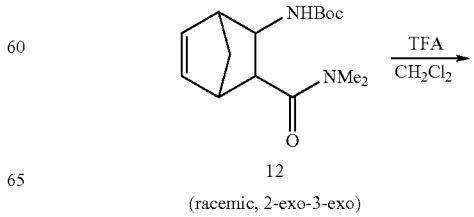

12

(racemic, 2-exo-3-exo)

-continued

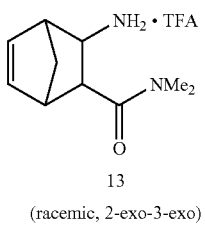

13
(racemic, 2-exo-3-exo)

To a suspension of N-Boc lactam 10 (1.3 g, 5.52 mmol) in toluene (20 mL) were added 40% methylamine solution in water (3 mL) and p-toluenesulfonic acid monohydrate (70 mg). The reaction mixture was stirred at 100° C. for 17 hours to effect cleavage of the β-lactam ring. The volatiles were evaporated under reduced pressure and the residue was then dissolved in $CH_2Cl_2$ (10 mL). Trifluoroacetic acid (TFA, 5 mL) was added and the resulting reaction mixture was stirred at room temperature for 3 hours to remove the Boc-protecting group. The volatiles were evaporated under reduced pressure, and the isolated TFA salt 13 was used in the next step without further purification.

Example 2

General Procedure for Synthesis of Purine Mono-$SN_{Ar}$ Products

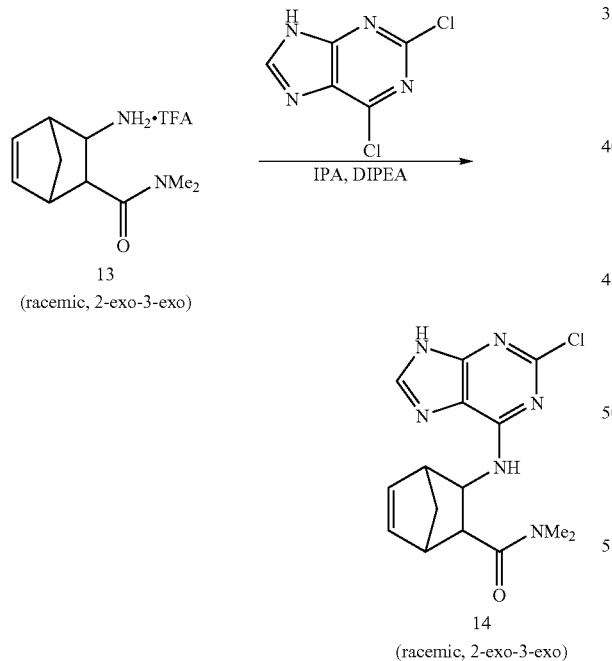

A glass tube was charged with the above amount of TFA salt 13, commercially available 2,6-dichloropurine (1.02 g, 5.43 mmol), N, N-diisopropylethylamine (DIPEA, 3.14 mL, 4.96 mmol) and isopropyl alcohol (IPA, 6 mL). The glass tube was sealed and then shaken at 100° C. for 17 hours. The volatiles were evaporated and the resulting residue was purified by flash chromatography eluting with ethyl acetate-methanol (100:5, including 1% triethylamine) to afford 1.25 g of mono-SNA, product 14, racemic-(2-exo,3-exo-)-N6-[3-(dimethylamino)carbonylbicyclo-[2.2.1]hept-5-en-2-yl)]-2-chloro-1H-purine-6-amine, in 70% yield. $^1$H NMR (300 MHz, $CD_3OD$) δ: 8.05 (s, 1H), 6.35 (m, 2H), 4.68 (m, 1H), 3.00 (s, 1H), 3.04 (s, 1H), 3.00 (s, 3H), 2.95 (s, 1H), 2.83 (s, 1H), 2.68 (s, 3H), 2.39 (d, J=8.7 Hz, 1H), 1.69 (d, J=9.0 Hz, 1H), 1,33 (m, 1H); LC-MS: purity: 90.51%; MS (m/e): 333.43 (M+H)$^+$.

Example 3

General Procedure for Synthesis of Second Purine $SN_{Ar}$ Products

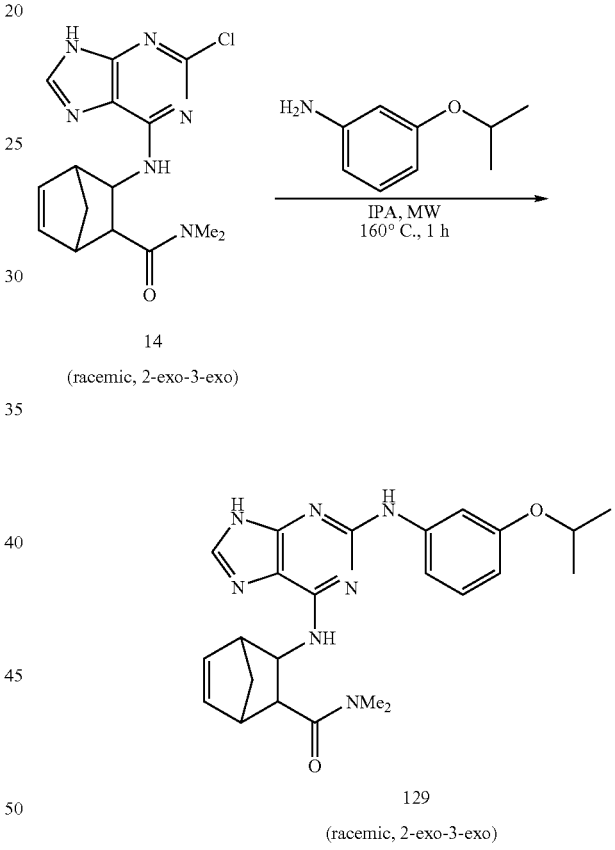

129
(racemic, 2-exo-3-exo)

The mono-$SN_{Ar}$ product 14 (40 mg, 0.12 mmol) and 3-isopropoxyaniline (44 μl, 0.3 mmol) were added to a microwave vial, followed by the addition of isopropyl alcohol (IPA, 0.8 mL) and 4 drops of TFA. The mixture was irradiated in a microwave oven at 155° C. for 60 minutes to effect the desired reaction. After cooling the reaction vessel to room temperature, the volatiles were evaporated under reduced pressure. The residue was purified by reverse-phase high performance liquid chromatography (RP-HPLC), eluting with a gradient of acetonitrile-water to provide the desired product 129, racemic-(2-exo,3-exo-)-N6-[3-(dimethylamino)carbonylbicyclo[2.2.1]hept-5-en-2-yl)]-N2-(3-isopropoxyphenyl)-1H-purine-2,6-diamine.

Example 4

General Procedure for Synthesis of Pyrrolo[2,3-d]pyrimidine Mono-SN$_{Ar}$ Products

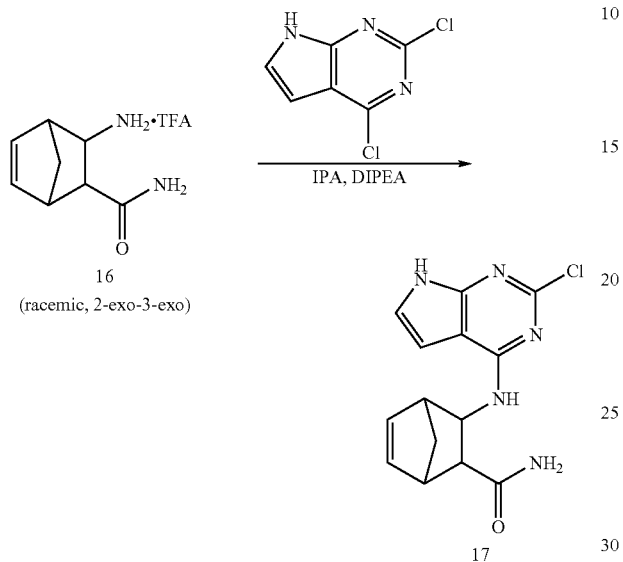

A sealed tube charged with TFA salt 16 (550 mg, 2.06 mmol), 2,4-dichloro-1H-pyrrolo[2,3-d]pyrimidine (350 mg, 1.87 mmol), N, N-diisopropylethylamine (1.02 mL, 6.19 mmol) and isopropyl alcohol (5 mL) was shaken at 60° C. for 48 hours and 100° C. for another 4 hours. The volatiles were evaporated, the resulting residue was then purified by flash chromatography eluting with ethyl acetate to afford 370 mg of mono-SNAr product 17, racemic-(2-exo,3-exo)-N4-(3-aminocarbonylbicyclo[2.2.1]hept-5-en-2-yl)-2-chloro-1H-pyrrolo[2,3-d]pyrimidine-4-amine, in 65% yield. $^1$H NMR (300 MHz, CD$_3$OD) δ: 7.01 (d, J=3.6 Hz, 1H), 6.48 (d, J=3.6 Hz, 1H), 6.32 (m, 2H), 4.45 (d, J=7.2 Hz, 1H), 2.95 (s, 1H), 2.83 (s, 1H), 2.66 (dd, J=1.5, 8.1 Hz, 1H), 2.34 (d, J=9.3 Hz, 1H), 1.59 (d, J=9.0 Hz, 1H); LC-MS: purity: 91.82%; MS (m/e): 304.41 (M+H)$^+$

Example 5

General Procedure for Synthesis of Second Pyrrolo[2,3-d]pyrimidine SNAr Products

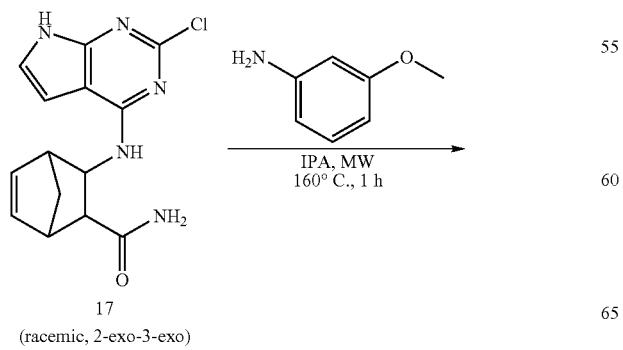

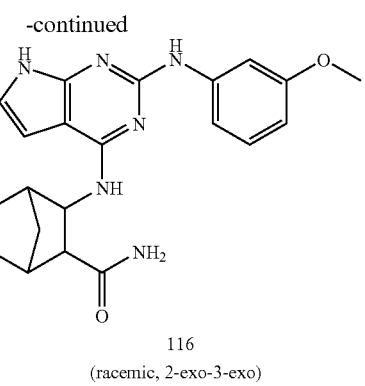

The mono-SNAr product 17 (30 mg, 0.1 mmol) and m-toluidine (22 Pl, 0.2 mmol) were added to a microwave vial, followed by the addition of isopropyl alcohol (0.8 mL) and 4 drops of TFA. The mixture was irradiated in a microwave oven at 155° C. for 60 min. After cooling to room temperature, the volatiles were evaporated under reduced pressure. The residue was purified by HPLC eluting with acetonitrile-water to provide the desired product 116.

Example 6

General Procedure for Synthesis of Quinazoline Mono-SN$_{Ar}$ Products

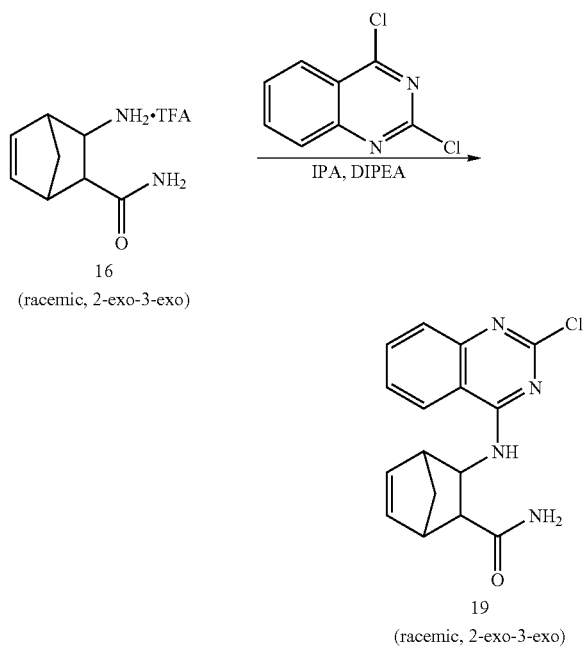

A microwave vial charged with TFA salt 16 (402 mg, 1.5 mmol), commercially available 2,4-dichloroquinazoline (300 mg, 1.5 mmol), N, N-diisopropylethylamine (0.75 mL, 4.5 mmol) and isopropyl alcohol (2 mL) was irradiated in a microwave oven at 160° C. for 40 min. After cooling to room temperature, the volatiles were evaporated under reduced pressure. The resulting residue was then purified by flash chromatography eluting with ethyl acetate-hexanes (100:40, including 1% triethylamine) to afford 150 mg of mono-SNAr product 19, racemic-(2-exo,3-exo)-2-chloro-N4-(3-aminocarbonylbicyclo[2.2.1]hept-5-en-2-yl)-4-quinazoline-amine, in 31% yield. $^1$H NMR (300 MHz, DMSO-d$_6$) δ: 9.11 (d, J=7.2 Hz, 1H), 7.89 (d, J=8.4 Hz, 1H), 7.81-7.51 (m, 4H), 7.17 (s, 1H), 6.32 (m, 2H), 4.22 (t, J=7.2 Hz, 1H), 2.90 (s, 1H), 2.84 (s, 1H), 2.57 (d, J=8.1 Hz, 1H), 2.24 (d, J=8.7 Hz, 1H), 1.44 (d, J=9.0 Hz, 1H); LC-MS: purity: 100%; MS (m/e): 315.00 (M+H)$^+$.

Example 7

General Procedure for Synthesis of Second Quinazoline SN$_{Ar}$ Products

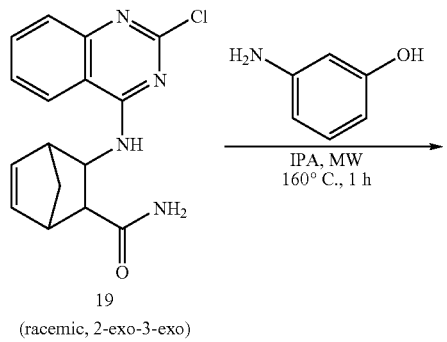

The mono-SNAr product 19 (35 mg, 0.11 mmol) and 3-aminophenol (15 mg, 0.13 mmol) were added to a microwave vial, followed by the addition of isopropyl alcohol (0.6 mL) and N,N-diisopropylethylamine (55 μl, 0.33 mmol). The mixture was irradiated in a microwave oven at 160° C. for 1 hour. After cooling to room temperature, the volatiles were evaporated under reduced pressure. The residue was purified by HPLC eluting with acetonitrile-water to provide the desired product 102.

Example 8

Synthesis of Additional Compounds

Additional compounds synthesized using the above-described methods are illustrated in Tables 1 and 2, below.

TABLE 1

| No. | Structure | Name | Spectroscopic Data |
|---|---|---|---|
| 101 | 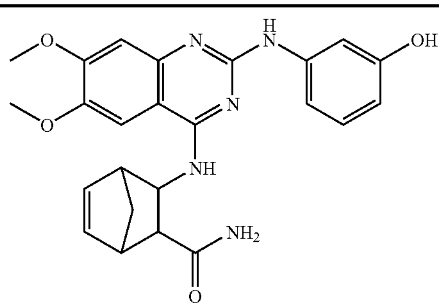 | Racemic-(2-exo,3-exo)-N4-(3-aminocarbonylbicyclo[2.2.1]hept-5-en-2-yl)-6,7-dimethoxy-N2-(3-hydroxy)phenyl-2,4-quinazoline-diamine | $^1$H NMR (CDCl$_3$): δ 8.40 (s, 1H), 7.26 (m, 2H), 7.03 (t, J=8.1 Hz, 1H), 6.87 (m, 2H), 6.46 (dd, J=2.7, 7.8 Hz, 1H), 6.29 (dd, J=2.7, 6.0 Hz, 1H), 6.19 (dd, J=2.7, 6.0 Hz, 1H), 4.15 (d, J=8.1 Hz, 1H), 4.00 (s, 6H), 3.89 (s, 1H), 3.84 (s, 1H), 3.21 (m, 1H), 2.94 (s, 1H), 2.83 (m, 1H), 2.47 (d, J=7.8 Hz, 1H), 2.20 (d, J=9.3 Hz, 1H), 1.47 (d, J=9.9 Hz, 1H), 1.37 (m, 1H); LC-MS: purity: 100%; MS (m/e) : 448.11 (M + H)$^+$ |
| 102 | 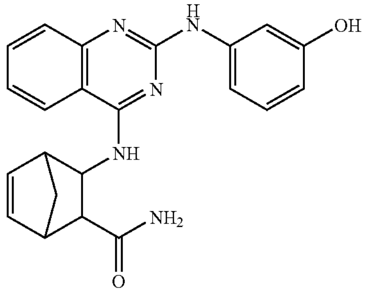 | Racemic-(2-exo,3-exo)-N4-(3-aminocarbonylbicyclo[2.2.1]hept-5-en-2-yl)-N2-(3-hydroxy)phenyl-2,4-quinazoline-diamine | $^1$H NMR (CD$_3$OD): δ 7.81 (m, 3H), 7.48 (m, 2H), 7.21 (t, J=8.1 Hz, 1H), 7.13 (s, 1H), 6.99 (m, 1H), 6.69 (dd, J=1.5, 7.2 Hz, 1H), 6.39 (m, 1H), 4.27 (m, 1H), 3.07 (d, J=8.1 Hz, 1H), 2.65 (m, 1H), 2.16 (d, J=9.0 Hz), 1.58 (d, J=9.3 Hz, 1H); LC-MS: purity: 100%; MS (m/e): 388.39 (M + H)$^+$ |

TABLE 1-continued

| No. | Structure | Name | Spectroscopic Data |
|---|---|---|---|
| 103 | 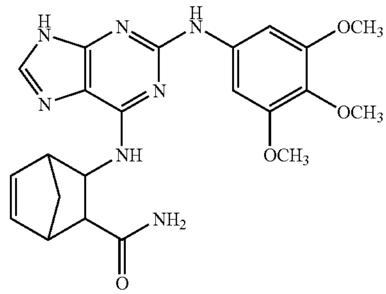 | Racemic-(2-exo,3-exo)-N6-(3-aminocarbonylbicyclo[2.2.1]hept-5-en-2-yl)-N2-(3,4,5-trimethoxy)phenyl-1H-purine-2,6-diamine | $^1$H NMR (CD$_3$OD): δ 8.10 (s, 1H), 7.77 (s, 1H), 7.10 (m, 2H), 6.31 (m, 2H), 4.67 (m, 1H), 3.31 (s, 3H), 3.30 (s, 6H), 2.98 (s, 1H), 2.84 (s, 1H), 2.67 (d, J=8.4 Hz, 1H), 2.38 (d, J=9.3 Hz, 1H), 1.64 (d, J=8.7 Hz, 1H); LC-MS: purity: 100%; MS (m/e): 452.10 (M + H)$^+$ |
| 104 | 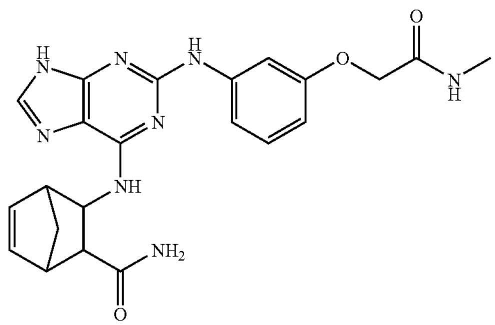 | Racemic-(2-exo,3-exo)-N6-(3-aminocarbonylbicyclo[2.2.1]hept-5-en-2-yl)-N2-[3-[2-(methylamino)-2-oxoethoxy]phenyl]]-1H-purine-2,6-diamine | $^1$H NMR (DMSO-d$_6$): δ 8.89 (s, 1H), 8.10 (s, 1H) 7.26 (m, 4H), 7.10 (m, 1H), 6.42-6.29 (m, 3H), 2.85 (s, 1H), 2.76 (s, 1H), 2.65 (d, J=4.5 Hz, 3H), 3.54 (d, J=8.4 Hz, 1H), 2.19 (d, J=8.1 Hz, 1H), 1.40 (d, J=8.4 Hz, 1H); LC-MS: purity: 100%; MS (m/e): 449.07(M + H)$^+$ |
| 105 | 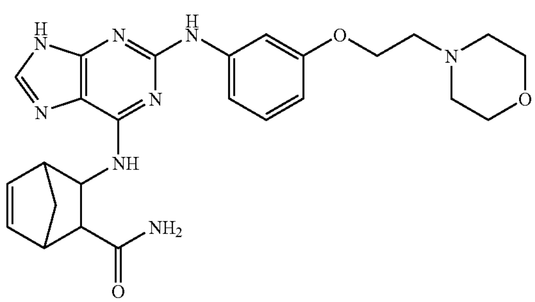 | Racemic-(2-exo,3-exo)-N6-(3-aminocarbonylbicyclo[2.2.1]hept-5-en-2-yl)-N2-[3-(2-morpholin-4-yl-ethoxy)phenyl]-1H-purine-2,6-diamine | $^1$H NMR (CD$_3$OD): δ 8.10 (s, 1H), 7.80 (s, 1H), 7.55 (m, 1H), 7.27-7.12 (m, 2H), 6.60-6.54 (m, 2H), 6.33 (m, 2H), 4.58 (m, 1H), 4.35 (m, 2H), 3.96-3.81 (m, 4H), 3.47 (m, 2H), 3.18 (m, 2H), 3.13 (s, 1H), 2.98 (s, 1H), 2.86 (s, 1H), 2.70 (d, J=7.8 Hz, 1H), 2.36 (d, J=8.1 Hz, 1H), 1.64 (d, J=7.2 Hz, 1H); LC-MS: purity: 100%; MS (m/e): 491.14 (M + H)$^+$ |
| 106 | 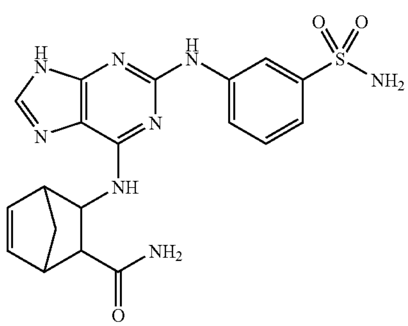 | Racemic-(2-exo,3-exo)-N6-(3-aminocarbonylbicyclo[2.2.1]hept-5-en-2-yl)-N2-(3-aminosulfonyl)phenyl-1H-purine-2,6-diamine | $^1$H NMR (CD$_3$OD): δ 8.49 (s, 1H), 8.12 (s, 1H), 7.79-7.75 (m, 2H), 7.45-7.36 (m, 2H), 6.31 (m, 2H), 4.64 (m, 1H), 2.97 (s, 1H), 2.83 (s, 1H), 2.76 (d, J=7.8 Hz, 1H), 2.39 (d, J=8.7 Hz, 1H), 1.64 (d, J=7.5 Hz, 1H); LC-MS: purity: 100%; MS (m/e): 441.00 (M + H)$^+$ |
| 107 | 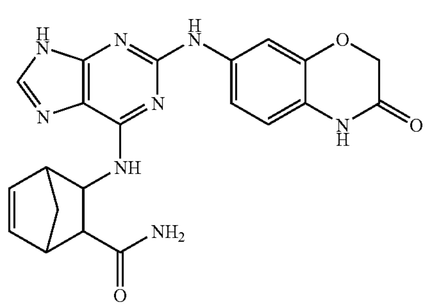 | Racemic-(2-exo,3-exo)-N6-(3-aminocarbonylbicyclo[2.2.1]hept-5-en-2-yl)-N2-(3,4-dihydro-3-oxo-2H-1,4-benzoxazin-7-yl)-1H-purine-2,6-diamine | $^H$ NMR (CD$_3$OD): δ 8.20 (s, 1H), 7.74 (s, 1H), 7.63 (s, 1H), 7.11 (m, 2H), 6.78 (d, J=8.4 Hz, 2H), 6.34 (m, 2H), 4.59 (m, 1H), 4.56 (s, 2H), 2.97 (s, 1H), 2.86 (s, 1H), 2.68 (d, J=8.4 Hz, 1H), 2.36 (d, J=9.0 Hz, 1H), 1.62 (d, J=6.9 Hz, 1H); LC-MS: purity: 100.00%; MS (m/e) : 433.03 (M + H)$^+$ |

TABLE 1-continued

| No. | Structure | Name | Spectroscopic Data |
|---|---|---|---|
| 108 | 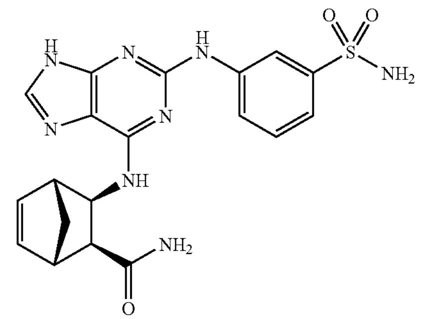 | (1R,2R,3S,4S)-N6-(3-Aminocarbonylbicyclo[2.2.1]hept-5-en-2-yl)-N2-(3-aminosulfonyl)phenyl-1H-purine-2,6-diamine | LC-MS: purity: 100%; MS (m/e) : 441.49 (M + H)+ |
| 109 | 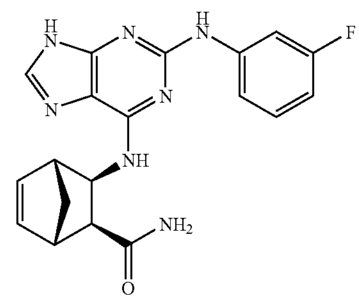 | (1R,2R,3S,4S)-N6-(3-Aminocarbonylbicyclo[2.2.1]hept-5-en-2-yl)-N2-(3-fluoro)phenyl-1H-purine-2,6-diamine | $^1$H NMR (CD$_3$OD): δ 8.15 (s, 1H), 7.91 (d, J=12.6 Hz, 1H), 7.77 (s, 1H), 7.25-7.14 (m, 2H), 6.63-6.56 (m, 1H), 6.37 (m, 2H), 4.53 (m, 1H), 2.98 (s, 1H), 2.87 (s, 1H), 2.70 (d, J=7.8 Hz, 1H), 2.35 (d, J=9.0 Hz, 1H), 1.62 (d, J=9.0 Hz, 1H); LC-MS: purity: 100.00%; MS (m/e) : 356.14 (M +H)+ |
| 110 | 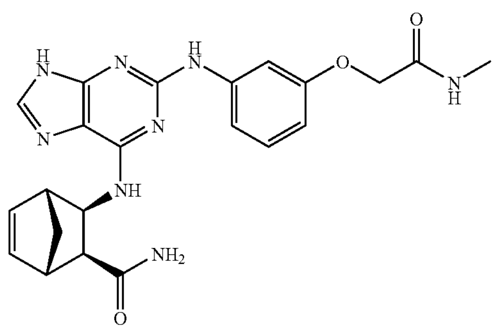 | (1R,2R,3S,4S)-N6-(3-Aminocarbonylbicyclo[2.2.1]hept-5-en-2-yl)-N2-[3-[2-(methylamino)-2-oxoethoxy]phenyl]]-1H-purine-2,6-diamine | LC-MS: purity: 100%; MS (m/e) : 449.48 (M + H)+ |
| 111 | 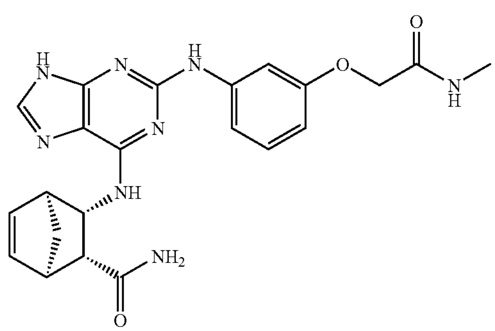 | (1S,2S,3R,4R)-N6-(3-Aminocarbonylbicyclo[2.2.1]hept-5-en-2-yl)-N2-[3-[2-(methylamino)-2-oxoethoxy]phenyl]]-1H-purine-2,6-diamine | LC-MS: purity: 99.00%; MS (m/e) : 449.80 (M + H)+ |
| 112 | 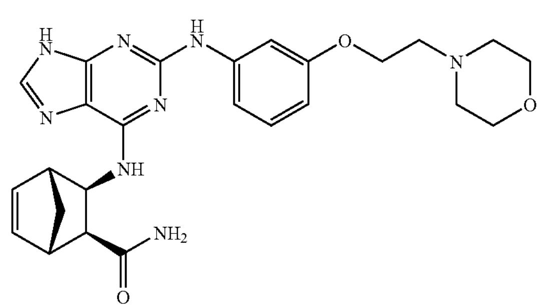 | (1R,2R,3S,4S)-N6-(3-Aminocarbonylbicyclo[2.2.1]hept-5-en-2-yl)-N2-[3-(2-morpholin-4-yl-ethoxy)phenyl]-1H-purine-2,6-diamine | LC-MS: purity: 97.49%; MS (m/e) : 491.91 (M + H)+ |

TABLE 1-continued

| No. | Structure | Name | Spectroscopic Data |
| --- | --- | --- | --- |
| 113 | 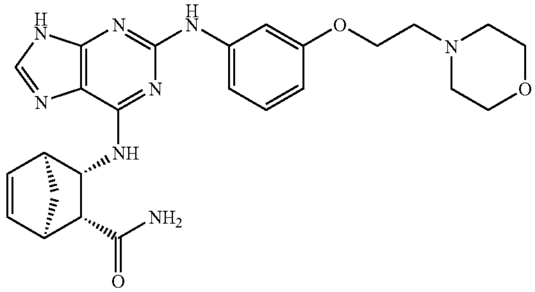 | (1S,2S,3R,4R)-N6-(3-Aminocarbonylbicyclo[2.2.1]hept-5-en-2-yl)-N2-[3-(2-morpholin-4-yl-ethoxy)phenyl]-1H-purine-2,6-diamine | LC-MS: purity: 99.63%; MS (m/e) : 491.72 (M + H)+ |
| 114 | 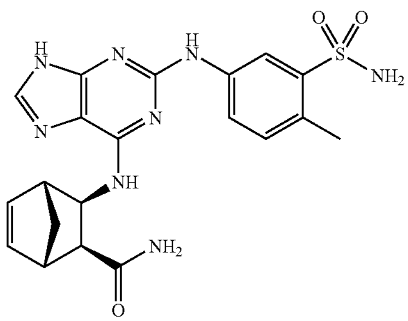 | (1R,2R,3S,4S)-N6-(3-Aminocarbonylbicyclo[2.2.1]hept-5-en-2-yl)-N2-(3-aminosulfonyl-4-methyl)phenyl-1H-purine-2,6-diamine | $^1$H NMR (CD$_3$OD): δ 8.45 (m, 1H), 8.25 (s, 1H), 7.76 (s, 1H), 7.72 (d, J=2.4, 8.1 Hz, 1H), 7.22 (d, J=8.1 Hz, 1H), 6.31 (m, 2H), 4.63 (m, 1H), 2.97 (s, 1H), 2.82 (s, 1H), 2.73 (d, J=8.4 Hz, 1H), 2.60 (s, 3H), 2.37 (d, J=9.3 Hz, 1H), 1.63 (d, J=7.8 Hz, 1H); LC-MS: purity: 100%; MS (m/e): 455.51 (M + H)+ |
| 115 | 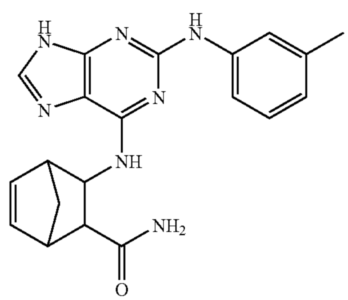 | Racemic-(2-exo,3-exo)-N6-(3-aminocarbonylbicyclo[2.2.1]hept-5-en-2-yl)-N2-(3 methyl)phenyl-1H-purine-2,6-diamine | $^1$H NMR (CD$_3$OD): δ 8.13 (s, 1H), 7.76 (s, 1H), 7.52 (s, 1H), 7.44 (d, J=7.5 Hz, 1H), 7.12 (t, J=7.5 Hz, 1H), 6.75 (d, J=7.5 Hz, 1H), 6.32 (m, 2H), 4.53 (m, 1H), 2.98 (s, 1H), 2.85 (s, 1H), 2.67 (d, J=8.1 Hz, 1H), 2.35 (d, J=9.0 Hz, 1H), 2.32 (s, 3H), 1.64 (d, J=9.3 Hz, 1H); LC-MS: purity: 100.00%; MS (m/e): 376.14 (M + H)+ |
| 116 | 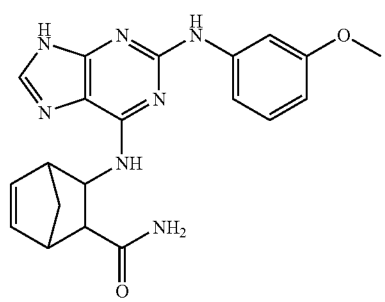 | Racemic-(2-exo,3-exo)-N6-(3-aminocarbonylbicyclo[2.2.1]hept-5-en-2-yl)-N2-(3-methoxy)phenyl-1H-purine-2,6-diamine | $^1$H NMR (CD$_3$OD): δ 8.13 (s, 1H), 7.76 (s, 1H), 7.53 (s, 1H), 7.11 (m, 2H), 6.52 (m, 2H), 6.32 (m, 2H), 4.53 (m, 1H), 3.79 (s, 3H), 2.97 (s, 1H), 2.87 (s, 1H), 2.68 (d, J=7.8 Hz, 1H), 2.35 (d, J=9.0 Hz, 1H), 1.64 (d, J=9.0 Hz, 1H); LC-MS: purity: 100.00%; MS (m/e): 392.13 (M + H)+ |
| 117 | 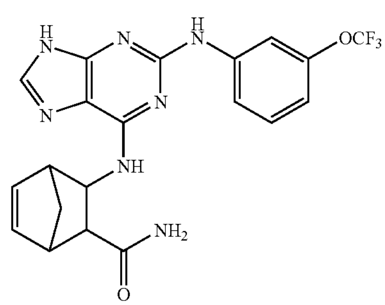 | Racemic-(2-exo,3-exo)-N6-(3-aminocarbonylbicyclo[2.2.1]hept-5-en-2-yl)-N2-(3-trifluoromethoxy)phenyl-1H-purine-2,6-diamine | $^1$H NMR (CD$_3$OD): δ 8.17 (s, 1H), 7.80 (s, 1H), 7.78 (m, 2H), 7.13 (m, 2H), 6.34 (m, 2H), 4.60 (m, 1H), 2.98 (s, 1H), 2.86 (s, 1H), 2.68 (d, J=8.1 Hz, 1H), 2.36 (d, J=9.3 Hz, 1H), 1.62 (d, J=9.0 Hz, 1H); LC-MS: purity: 100.00%; MS (m/e) : 446.10 (M + H)+ |

… TABLE 1-continued

| No. | Structure | Name | Spectroscopic Data |
|---|---|---|---|
| 118 | 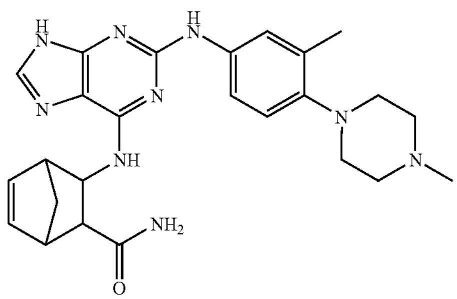 | Racemic-(2-exo,3-exo)-N6-(3-aminocarbonylbicyclo[2.2.1]hept-5-en-2-yl)-N2-[3-methyl-4-(4-methylpiperazine-1-yl)phenyl]-1H-purine-2,6-diamine | $^1$H NMR (CD$_3$OD): δ 8.13 (s, 1H), 7.77 (s, 1H), 7.55-7.47 (m, 2H), 7.03 (d, J=8.4 Hz, 1H), 6.34 (m, 2H), 4.60 (m, 1H), 3.44 (m, 4H), 3.13 (m, 4H), 2.97 (s, 3H), 2.95 (s, 1H), 2.85 (s, 1H), 2.67 (d, J=8.1 Hz, 1H), 2.37 (d, J=8.7 Hz, 1H), 2.32 (s, 3H), 1.62 (d, J=8.7 Hz, 1H); LC-MS: purity: 100.00%; MS (m/e) : 474.70 (M + H)$^+$ |
| 119 | 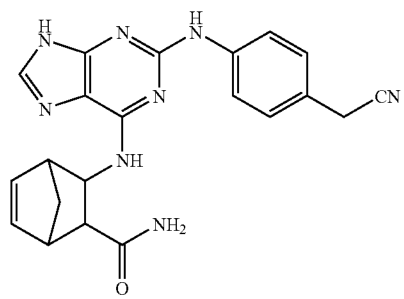 | Racemic-(2-exo,3-exo)-N6-(3-aminocarbonylbicyclo[2.2.1]hept-5-en-2-yl)-N2-(4-cyanomethyl)phenyl-1H-purine-2,6-diamine | $^1$H NMR (CD$_3$OD): δ 7.75 (s, 1H), 7.73 (d, J=8.7 Hz, 2H), 7.22 (d, J=8.7 Hz, 2H), 6.33 (m, 2H), 4.61 (m, 1H), 3.82 (s, 2H), 2.98 (s, 1H), 2.86 (s, 1H), 2.69 (d, J=8.4 Hz, 1H), 2.36 (d, J=9.0 Hz, 1H), 1.62 (d, J=9.0 Hz, 1H); LC-MS: purity: 100.00%; MS (m/e) : 401.10 (M + H)$^+$ |
| 121 | 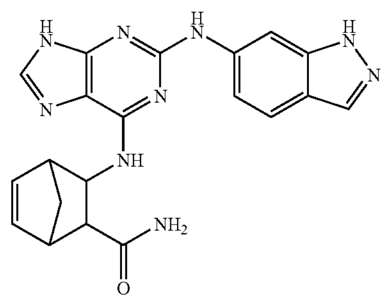 | Racemic-(2-exo,3-exo)-N6-(3-aminocarbonylbicyclo[2.2.1]hept-5-en-2-yl)-N2-(1H-indazol-6-yl)-1H-purine-2,6-diamine | $^1$H NMR (CD$_3$OD): δ 8.27 (s, 1H), 8.19 (s, 1H), 7.89 (s, 1H), 7.78 (m, 1H), 7.61 (s, 1H), 7.58 (s, 1H), 7.23 (d, J=8.4 Hz, 1H), 6.33 (m, 2H), 4.62 (m, 1H), 2.98 (s, 1H), 2.86 (s, 1H), 2.69 (d, J=8.1 Hz, 1H), 2.38 (d, J=9.0 Hz, 1H), 1.64 (d, J=9.0 Hz, 1H); LC-MS: purity: 100.00%; MS (m/e): 402.09 (M + H)$^+$ |
| 122 | 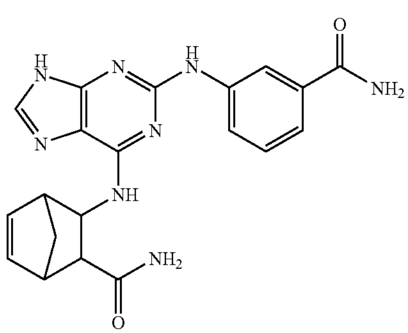 | Racemic-(2-exo,3-exo)-N6-(3-aminocarbonylbicyclo[2.2.1]hept-5-en-2-yl)-N2-(3-aminocarbonyl)phenyl-1H-purine-2,6-diamine | $^1$H NMR (DMSO-d$_6$): δ 8.97 (s, 1H), 8.13 (s, 1H), 7.97 (m, 1H), 7.74 (m, 1H), 7.28 (m, 3H), 6.29 (m, 2H), 4.39 (m, 1H), 2.92 (s, 1H), 2.88 (s, 1H), 2.22 (d, J=8.1 Hz, 1H), 1.41 (d, J=8.4 Hz, 1H); LC-MS: purity: 100%; MS (m/e) : 405.12 (M + H)$^+$ |
| 123 | 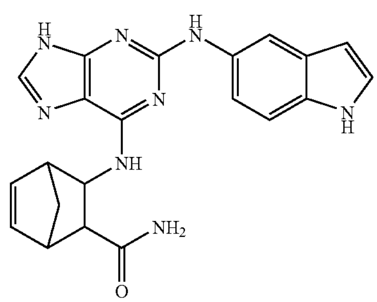 | Racemic-(2-exo,3-exo)-N6-(3-aminocarbonylbicyclo[2.2.1]hept-5-en-2-yl)-N2-(1H-indol-5-yl)-1H-purine-2,6-diamine | $^1$H NMR (CD$_3$OD): δ 8.18 (s, 1H), 7.84 (m, 7.21-7.17 (m, 2H), 6.38 (m, 1H), 6.32 (m, 1H), 7.73 (s, 1H), 7.33 (d, J=8.7 Hz, 1H), 2H), 4.61 (m, 1H), 2.97 (s, 1H), 2.86 (s, 1H), 2.63 (d, J=8.1 Hz, 1H), 2.38 (d, J=9.3 Hz, 1H), 1.63 (d, J=9.0 Hz, 1H); LC-MS: purity: 100.00%; MS (m/e) : 402.09 (M + H)$^+$ |

TABLE 1-continued

| No. | Structure | Name | Spectroscopic Data |
|---|---|---|---|
| 124 | 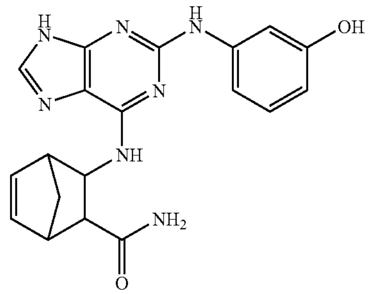 | Racemic-(2-exo,3-exo)-N6-(3-aminocarbonylbicyclo[2.2.1]hept-5-en-2-yl)-N2-(3-hydroxy)phenyl-1H-purine-2,6-diamine | $^1$H NMR (CD$_3$OD): δ 8.13 (s, 1H), 7.76 (s, 1H), 7.31 (m, 1H), 7.05 (m, 2H), 6.41-6.30 (m, 2H), 4.60 (m, 1H), 2.97 (s, 1H), 2.87 (s, 1H), 2.68 (d, J=8.1 Hz, 1H), 2.36 (d, J=9.0 Hz, 1H), 1.62 (d, J=9.0 Hz, 1H); LC-MS: purity: 100.00%; MS (m/e): 378.13 (M + H)$^+$ |
| 125 | 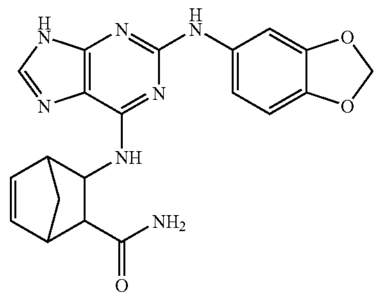 | Racemic-(2-exo,3-exo)-N6-(3-aminocarbonylbicyclo[2.2.1]hept-5-en-2-yl)-N2-(1,3-benzodioxol-5-yl)-1H-purine-2,6-diamine | $^1$H NMR (CD$_3$OD): δ 8.14 (s, 1H), 7.73 (s, 1H), 7.52 (s, 1H), 6.88 (dd, J=2.1, 8.1 Hz, 1H), 6.71 (d, J=8.1 Hz, 1H), 6.33 (m, 2H), 5.89 (s, 2H), 4.58 (m, 1H), 2.97 (s, 1H), 2.87 (s, 1H), 2.66 (d, J=8.4 Hz, 1H), 2.34 (d, J=9.3 Hz, 1H), 1.62 (d, J=9.3 Hz, LC-MS: purity: 100.00%; MS (m/e): 406.11 (M + H)$^+$ |
| 126 | 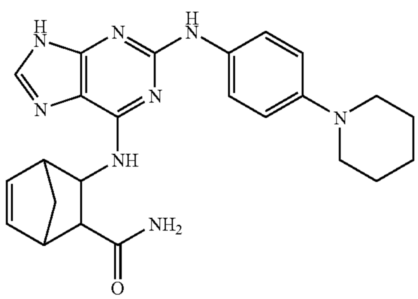 | Racemic-(2-exo,3-exo)-N6-(3-aminocarbonylbicyclo[2.2.1]hept-5-en-2-yl)-N2-(4-piperidino)phenyl-1H-purine-2,6-diamine | $^1$H NMR (CD$_3$OD): δ 8.15 (s, 1H), 7.75 (s, 1H), 7.65 (d, J=8.7 Hz, 1H), 7.13 (d, J=9.0 Hz, 1H), 6.33 (m, 2H), 4.58 (m, 1H), 2.98 (s, 1H), 2.86 (s, 1H), 2.66 (d, J=7.8 Hz, 1H), 2.34 (d, J=8.7 Hz, 1H), 1.84 (m, 4H), 1.65 (m, 5H); LC-MS: purity: 100.00%; MS (m/e) : 445.64 (M + H)$^+$ |
| 127 | 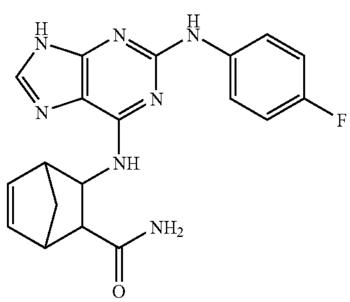 | Racemic-(2-exo,3-exo)-N6-(3-aminocarbonylbicyclo[2.2.1]hept-5-en-2-yl)-N2-(3-fluoro)phenyl-1H-purine-2,6-diamine | $^1$H NMR (CD$_3$OD): δ 8.16 (s, 1H), 7.74 (s, 1H), 7.66 (m, 2H), 6.97 (m, 2H), 6.32 (m, 2H), 4.57 (m, 1H), 2.97 (s, 1H), 2.85 (s, 1H), 2.67 (d, J=8.1 Hz, 1H), 2.35 (d, J=9.3 Hz, 1H), 1.62 (d, J=9.3 Hz, 1H); LC-MS: purity: 100.00%; MS (m/e): 380.53 (M + H)$^+$ |
| 128 | 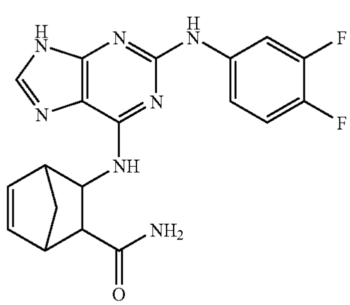 | Racemic-(2-exo,3-exo)-N6-(3-aminocarbonylbicyclo[2.2.1]hept-5-en-2-yl)-N2-(3,4-difluoro)phenyl-1H-purine-2,6-diamine | $^1$H NMR (CD$_3$OD): δ 8.13 (s, 1H), 7.76 (s, 1H), 7.24-7.01 (m, 3H), 6.34 (m, 2H), 4.60 (m, 1H), 2.98 (s, 1H), 2.87 (s, 1H), 2.67 (d, J=8.4 Hz, 1H), 2.34 (d, J=9.0 Hz, 1H), 1.62 (d, J=9.0 Hz, 1H); LC-MS: purity: 100.00%; MS (m/e): 398.54 (M + H)$^+$ |

TABLE 1-continued

| No. | Structure | Name | Spectroscopic Data |
|---|---|---|---|
| 129 | 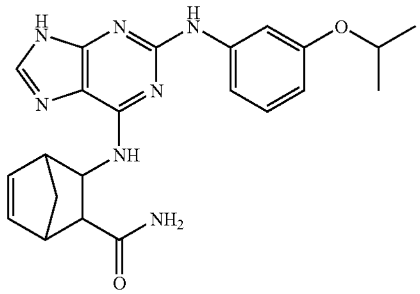 | Racemic-(2-exo,3-exo-)-N6-(3-aminocarbonylbicyclo[2.2.1]hept-5-en-2-yl)-N2-(3-isopropoxy)phenyl-1H-purine-2,6-diamine | $^1$H NMR (CD$_3$OD): δ 8.13 (s, 1H), 7.75 (s, 1H), 7.54 (s, 1H), 7.14-7.05 (m, 2H), 6.49 (d, J=7.8 Hz, 1H), 6.39-6.31 (m, 2H), 4.62-4.54 (m, 2H), 2.98 (s, 1H), 2.87 (s, 1H), 2.69 (d, J=6.9 Hz, 1H), 2.36 (d, J=8.7 Hz, 1H), 1.62 (d, J=8.7 Hz, 1H), 1,32 (d, J=5.7 Hz, 6H); LC-MS: purity: 100.00%; MS (m/e) : 420.09 (M + H)$^+$ |
| 130 | 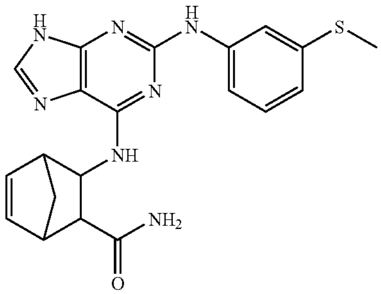 | Racemic-(2-exo,3-exo)-N6-(3-aminocarbonylbicyclo[2.2.1]hept-5-en-2-yl)-N2-(3-methylthio)phenyl-1H-purine-2,6-diamine | $^1$H NMR (CD$_3$OD): δ 8.19 (s, 1H), 7.83-7.75 (m, 2H), 7.37-7.33 (m, 1H), 7.18-7.13 (m, 1H), 6.84-6.80 (m, 1H), 6.34 (m, 2H), 4.62 (m, 1H), 2.98 (s, 1H), 2.86 (s, 1H), 2.69 (d, J=7.5 Hz, 1H), 2.48 (s, 3H), 2.36 (d, J=9.0 Hz, 1H), 1.62 (d, J=9.0 Hz, 1H); LC-MS: purity: 100.00%; MS (m/e): 408.03 (M + H)$^+$ |
| 131 | 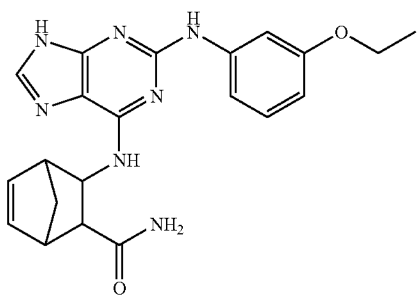 | Racemic-(2-exo,3-exo)-N6-(3-aminocarbonylbicyclo[2.2.1]hept-5-en-2-yl)-N2-(3-ethoxy)phenyl-1H-purine-2,6-diamine | $^1$H NMR (CD$_3$OD): δ 8.15 (s, 1H), 7.75 (s, 1H), 7.57 (s, 1H), 7.14-7.04 (m, 2H), 6.50-6.47 (m, 1H), 6.39-6.31 (m, 2H), 4.62 (m, 1H), 4.01 (q, J=6.9 Hz, 2H), 2.98 (s, 1H), 2.87 (s, 1H), 2.68 (d, J=8.1 Hz, 1H), 2.36 (d, J=8.7 Hz, 1H), 1.62 (d, J=9.0 Hz, 1H), 1.39 (t, J=6.9 Hz, 3H); LC-MS: purity: 100.00%; MS (m/e) : 406.11 (M + H)$^+$ |
| 132 | 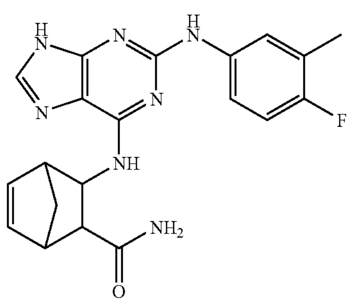 | Racemic-(2-exo,3-exo)-N6-(3-aminocarbonylbicyclo[2.2.1]hept-5-en-2-yl)-N2-[(4-fluoro-3-methyl)phenyl]-1H-purine-2,6-diamine | $^1$H NMR (CD$_3$OD): δ 8.13 (s, 1H), 7.75 (s, 1H), 7.55-7.53 (m, 1H), 7.46-7.41 (m, 1H), 6.89 (t, J=9.0 Hz, 1H), 6.31 (m, 2H), 4.60 (m, 1H), 2.97 (s, 1H), 2.84 (s, 1H), 2.67 (d, J=8.1 Hz, 1H), 2.36 (d, J=9.0 Hz, 1H), 2.24 (s, 3H), 1.62 (d, J=9.0 Hz, 1H); LC-MS: purity: 100.00%; MS (m/e): 394.09 (M + H)$^+$ |
| 133 | 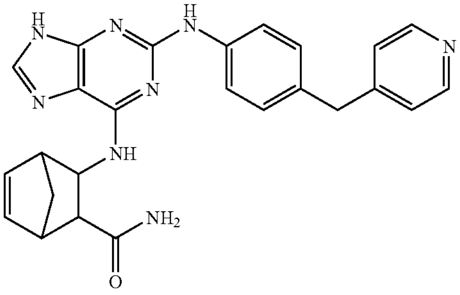 | Racemic-(2-exo,3-exo)-N6-(3-aminocarbonylbicyclo[2.2.1]hept-5-en-2-yl)-N2-[4-(4-pyridinylmethyl)phenyl]-1H-purine-2,6-diamine | $^1$H NMR (CD$_3$OD): δ 8.38 (m, 1H), 8.12 (s, 1H), 7.75 (s, 1H), 7.63 (d, J=8.4 Hz, 2H), 7.29 (m, 2H), 7.12 (d, J=8.7 Hz, 2H), 6.30 (m, 2H), 4.56 (m, 1H), 3.98 (s, 2H), 2.97 (s, 1H), 2.85 (s, 1H), 2.67 (d, J=8.1 Hz, 1H), 2.35 (d, J=8.7 Hz, 1H), 1.62 (d, J=8.7 Hz, 1H); LC-MS: purity: 100.00%; MS (m/e) : 453.08 (M + H)$^+$ |

TABLE 1-continued

| No. | Structure | Name | Spectroscopic Data |
| --- | --- | --- | --- |
| 134 | 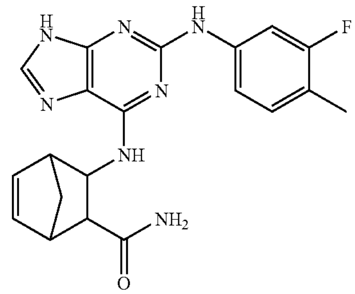 | Racemic-(2-exo,3-exo)-N6-(3-aminocarbonylbicyclo[2.2.1]hept-5-en-2-yl)-N2-(3-fluoro-4-methy)phenyl-1H-purine-2,6-diamine | $^1$H NMR (CD$_3$OD): 7.82-7.68 (m, 2H), 7.39-7.01 (m, 2H), 6.35 (m, 2H), 4.60 (m, 1H), 2.97 (s, 1H), 2.87 (s, 1H), 2.67 (d, J=8.4 Hz, 1H), 2.36 (d, J=8.7 Hz, 1H), 2.19 (s, 3H), 1.62 (d, J=8.7 Hz, 1H); LC-MS: purity: 100.00%; MS (m/e) : 394.039 (M + H)$^+$ |
| 135 | 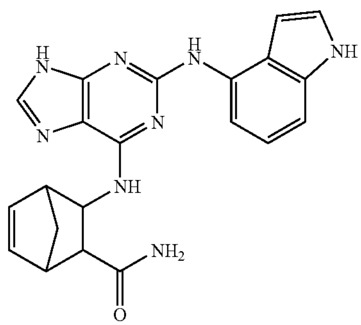 | Racemic-(2-exo,3-exo)-N6-(3-aminocarbonylbicyclo[2.2.1]hept-5-en-2-yl)-N2-(1H-indol-4-yl)-1H-purine-2,6-diamine | $^1$H NMR (CD$_3$OD): δ 8.30 (s, 1H), 7.82-7.79 (m, 1H), 7.75 (s, 1H), 7.18 (d, J=3.3 Hz, 1H), 7.10-7.02 (m, 1H), 6.58 (d, J=3.3 Hz, 1H), 6.33 (m, 2H), 4.61 (m, 1H), 2.97 (s, 1H), 2.86 (s, 1H), 2.63 (d, J=8.4 Hz, 1H), 2.38 (d, J=9.0 Hz, 1H), 1.63 (d, J=9.0 Hz, 1H); LC-MS: purity: 100.00%; MS (m/e) : 401.10 (M + H)$^+$ |
| 136 | 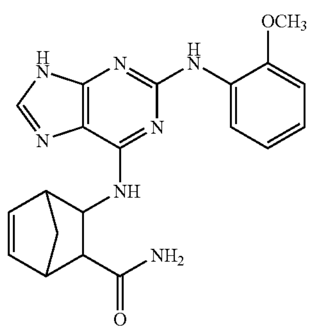 | Racemic-(2-exo,3-exo-)-N6-(3-aminocarbonylbicyclo[2.2.1]hept-5-en-2-yl)-N2-(2-methoxy)phenyl-1H-purine-2,6-diamine | $^1$H NMR (CD$_3$OD): δ 8.54 (s, 1H), 8.50 (m, 1H), 7.80 (s, 1H), 7.71 (m, 1H), 6.91 (m, 3H), 6.34 (m, 2H), 4.58 (m, 1H), 3.92 (s, 3H), 2.99 (s, 1H), 2.89 (s, 1H), 2.69 (d, J=8.4 Hz, 1H), 2.35 (d, J=9.0 Hz, 1H), 1.63 (d, J=7.5 Hz, 1H); LC-MS: purity: 100.00%; MS (m/e): 392.07 (M + H)$^+$ |
| 137 | 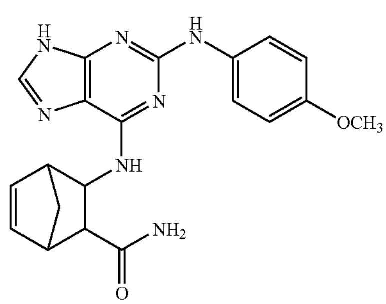 | Racemic-(2-exo,3-exo-)-N6-(3-aminocarbonylbicyclo[2.2.1]hept-5-en-2-yl)-N2-(3-methoxy)phenyl-1H-purine-2,6-diamine | $^1$H NMR (CD$_3$OD): δ 8.19 (s, 1H), 7.72 (s, 1H), 7.71 (m, 1H), 7.52 (d, J=9.0 Hz, 2H), 6.84 (d, J=9.0 Hz, 2H), 6.32 (m, 2H), 4.58 (m, 1H), 3.77 (s, 3H), 2.97 (s, 1H), 2.84 (s, 1H), 2.66 (d, J=8.4 Hz, 1H), 2.35 (d, J=9.0 Hz, 1H), 1.62 (d, J=8.7 Hz, 1H); LC-MS: purity: 100.00%; MS (m/e): 392.07 (M + H)$^+$ |
| 138 | 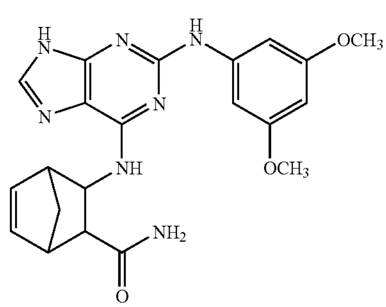 | Racemic-(2-exo,3-exo-)-N6-(3-aminocarbonylbicyclo[2.2.1]hept-5-en-2-yl)-N2-(3,5-dimethoxy)phenyl-1H-purine-2,6-diamine | $^1$H NMR (CD$_3$OD): δ 8.15 (s, 1H), 7.76 (s, 1H), 6.99 (s, 1H), 6.98 (s, 1H), 6.34 (m, 2H), 6.09 (s, 1H), 4.62 (m, 1H), 3.77 (s, 6H), 2.97 (s, 1H), 2.86 (s, 1H), 2.68 (d, J=9.0 Hz, 1H), 2.37 (d, J=8.7 Hz, 1H), 1.63 (d, J=7.2 Hz, 1H); LC-MS: purity: 100.00%; MS (m/e) : 422.06 (M + H)$^+$ |

TABLE 1-continued

| No. | Structure | Name | Spectroscopic Data |
|---|---|---|---|
| 139 | 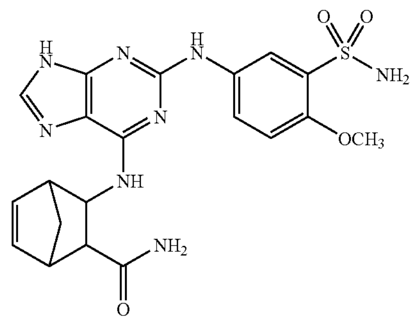 | Racemic-(2-exo,3-exo)-N6-(3-aminocarbonylbicyclo[2.2.1]hept-5-en-2-yl)-N2-(3-aminosulfonyl-4-methoxy)phenyl-1H-purine-2,6-diamine | $^1$H NMR (CD$_3$OD): δ 8.37 (d, J=2.7 Hz, 1H), 8.19 (s, 1H), 7.75 (s, 1H), 7.69 (dd, J=2.7, 9.0 Hz, 1H), 7.09 (d, J=9.3 Hz, 1H), 6.30 (m, 2H), 4.64 (m, 1H), 3.95 (s, 3H), 2.97 (s, 1H), 2.82 (s, 1H), 2.74 (d, J=8.1 Hz, 1H), 2.37 (d, J=9.3 Hz, 1H), 1.64 (d, J=9.0 Hz, 1H); LC-MS: purity: 100%; MS (m/e) : 471.55 (M + H)$^+$ |
| 140 | 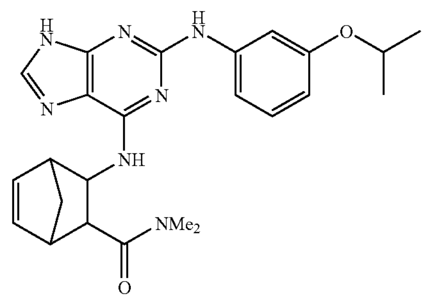 | Racemic-(2-exo,3-exo-)-N6-[3-(dimethylamino)carbonylbicyclo[2.2.1]hept-5-en-2-yl)]-N2-(3-isopropoxy)phenyl-1H-purine-2,6-diamine | $^1$H NMR (CD$_3$OD): δ 8.17 (s, 1H), 7.76 (s, 1H), 7.55 (m, 1H), 7.13-7.04 (m, 2H), 6.50-6.46 (m, 1H), 6.35 (m, 2H), 4.58 (pent, J=6.0 Hz, 1H), 4.91 (m, 1H), 3.00 (s, 1H), 2.98 (s, 1H), 2.91 (s, 3H), 2.83 (s, 1H), 2.72 (s, 3H), 2.65 (s, 1H), 2.35 (d, J=9.0 Hz, 1H), 1.68 (d, J=9.0 Hz, 1H), 1.32 (d, J=6.0 Hz, 6H); LC-MS: purity: 100.00%; MS (m/e) : 448.62 (M + H)$^+$ |
| 141 | 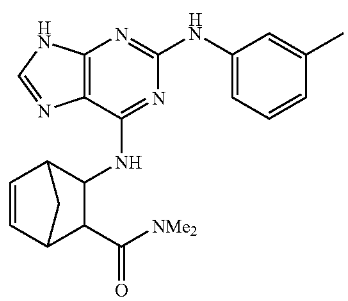 | Racemic-(2-exo,3-exo-)-N6-[3-(dimethylamino)carbonylbicyclo[2.2.1]hept-5-en-2-yl)]-N2-(3-methyl)phenyl-1H-purine-2,6-diamine | $^1$H NMR (CD$_3$OD): δ 8.14 (s, 1H), 7.75 (s, 1H), 7.42 (d, J=8.1 Hz, 1H), 7.10 (t,J=7.5 Hz, 1H), 2H), 6.75 (d, J=7.5 Hz, 1H), 6.33 (m, 2H), 4.92 (m, 1H), 3.00 (s, 1H), 2.97 (s, 1H), 2.89 (s, 3H), 2.82 (s, 1H), 2.72 (s, 3H), 2.35 (d, J=9.3 Hz, 1H), 2.31 (s, 3H), 1.68 (d, J=9.0 Hz, 1H); LC-MS: purity: 100.00%; MS (m/e): 404.63 (M + H)$^+$ |
| 142 | 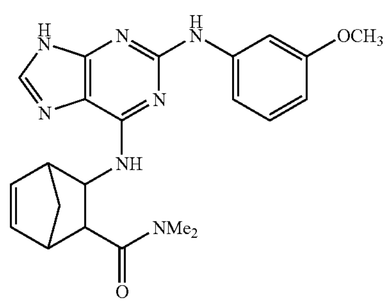 | Racemic-(2-exo,3-exo-)-N6-[3-(dimethylamino)carbonylbicyclo[2.2.1]hept-5-en-2-yl)]-N2-(3-methoxy)phenyl-1H-purine-2,6-diamine | $^1$H NMR (CD$_3$OD): δ 8.08 (s, 1H), 7.78 (s, 1H), 7.54 (s, 1H), 7.10 (m, 2H), 2H), 6.50 (m, 1H), 6.34 (m, 2H), 4.87 (m, 1H), 3.79 (s, 3H), 3.01 (s, 1H), 2.97 (s, 1H), 2.91 (s, 3H), 2.83 (s, 1H), 2.72 (s, 3H), 2.35 (d, J=9.0 Hz, 1H), 1.68 (d, J=9.3 Hz, 1H); LC-MS: purity: 100.00%; MS (m/e) : 420.58 (M + H)$^+$ |
| 143 | 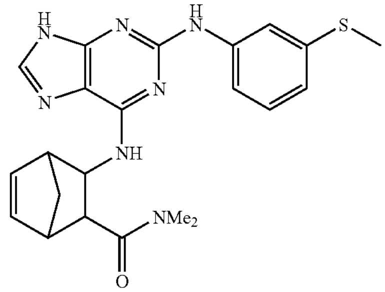 | Racemic-(2-exo,3-exo-)-N6-[3-(dimethylamino)carbonylbicyclo[2.2.1]hept-5-en-2-yl)]-N2-(3-methylthio)phenyl-1H-purine-2,6-diamine | $^1$H NMR (CD$_3$OD): δ 8.15 (s, 1H), 7.86 (s, 1H), 7.77 (s, 1H), 7.34-7.30 (m, 1H), 7.14 (t, J=8.1 Hz, 1H), 6.83-6.80 (m, 1H), 6.34 (m, 2H), 4.87 (m, 1H), 3.02 (s, 1H), 2.98 (m, 1H), 2.90 (s, 3H), 2.82 (s, 1H), 2.71 (s, 3H), 2.48 (s, 3H), 2.35 (d, J=9.0 Hz, 1H), 1.69 (d, J=9.0 Hz, 1H); LC-MS: purity: 100.00%; MS (m/e) : 436.02 (M + H)$^+$ |

TABLE 1-continued

| No. | Structure | Name | Spectroscopic Data |
|---|---|---|---|
| 144 | 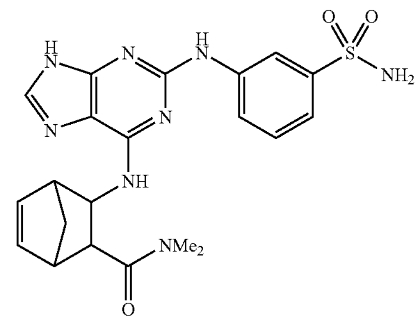 | Racemic-(2-exo,3-exo-)-N6-[3-(dimethylamino)carbonylbicyclo[2.2.1]hept-5-en-2-yl)]-N2-(3-aminosulfonyl)phenyl-1H-purine-2,6-diamine | $^1$H NMR (CD$_3$OD): δ 8.53 (s, 1H), 8.11 (s, 1H), 7.69-7.64 (m, 2H), 7.44-7.33 (m, 2H), 6.29 (m, 2H), 4.84 (m, 1H), 3.01 (s, 1H), 2.98 (m, 1H), 2.89 (s, 3H), 2.81 (s, 1H), 2.72 (s, 3H), 2.28 (d, J=9.0 Hz, 1H), 1.68 (d, J=9.3 Hz, 1H); LC-MS: purity: 100.00%; MS (m/e) : 469.54 (M + H)$^+$ |
| 145 | 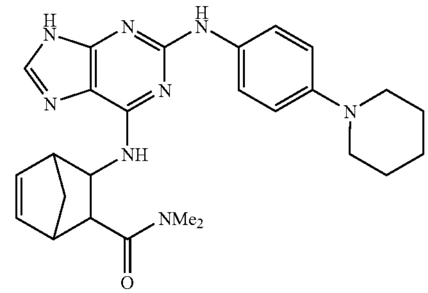 | Racemic-(2-exo,3-exo-)-N6-[3-(dimethylamino)carbonylbicyclo[2.2.1]hept-5-en-2-yl)]-N2-(4-piperidino)phenyl-1H-purine-2,6-diamine | $^1$H NMR (CD$_3$OD): δ 8.13 (m, 2H), 7.79 (s, 1H), 773 (d, d 32 9.0 Hz, 2H), 7.20 (d, J=7.5 Hz, 2H), 6.32 (m, 2H), 4.94 (m, 1H), 2.99 (s, 1H), 2.97 (s, 1H), 2.91 (s, 3H), 2.82 (s, 1H), 2.73 (s, 3H), 2.65 (s, 1H), 2.32 (d, J=8.7 Hz, 1H), 1.87 (m, 5H), 1.68 (m, 4H); LC-MS: purity: 100.00%; MS (m/e) : 473.65 (M + H)$^+$ |
| 146 | 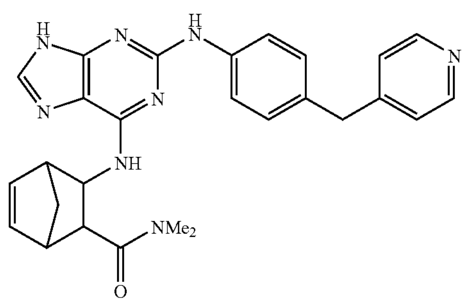 | Racemic-(2-exo,3-exo-)-N6-[3-(dimethylamino)carbonylbicyclo[2.2.1]hept-5-en-2-yl)]-N2-[4-(4-pyridinylmethyl)phenyl]-1H-purine-2,6-diamine | $^1$H NMR (CD$_3$OD): δ 8.40-8.38 (m, 2H), 8.10 (s, 1H), 7.76 (s, 1H), 7.64 (d, J=8.7 Hz, 2H), 7.30-7.28 (m, 2H), 7.11 (d, J=8.4 Hz, 2H), 6.32 (m, 2H), 4.90 (m, 1H), 3.98 (s, 2H), 2.95 (m, 2H), 2.90 (s, 3H), 2.81 (s, 1H), 2.73 (s, 3H), 2.65 (s, 1H), 2.32 (d, J=8.4 Hz, 1H), 1.68 (d, J=9.3 Hz, 1H); LC-MS: purity: 100.00%; MS (m/e) : 481.62 (M + H)$^+$ |
| 147 | 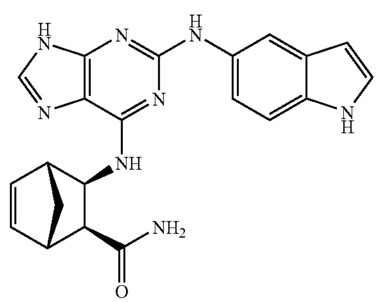 | (1R,2R,3S,4S)-N6-(3-Aminocarbonylbicyclo[2.2.1]hept-5-en-2-yl)-N2-(1H-indol-5-yl)-1H-purine-2,6-diamine | LC-MS: purity: 100.00%; MS (m/e): 402.50 (M + H)$^+$ |
| 148 | 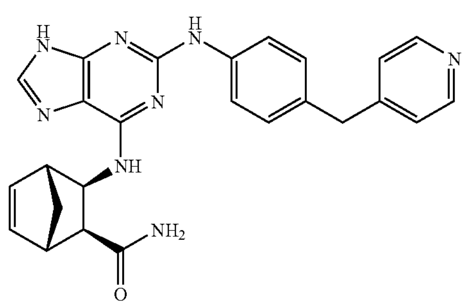 | (1R,2R,3S,4S)-N6-(3-Aminocarbonylbicyclo[2.2.1]hept-5-en-2-yl)-N2-[4-(4-pyridinylmethyl)phenyl]-1H-purine-2,6-diamine | LC-MS: purity: 100.00%; MS (m/e): 453.51 (M + H)$^+$ |

TABLE 1-continued

| No. | Structure | Name | Spectroscopic Data |
|---|---|---|---|
| 149 | 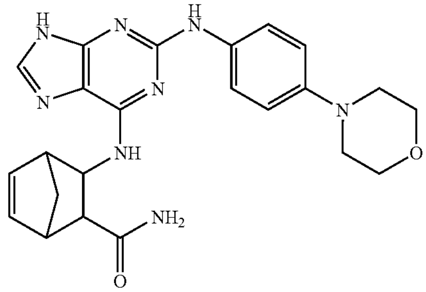 | Racemic-(2-exo,3-exo-)-N6-(3-aminocarbonylbicyclo[2.2.1]hept-5-en-2-yl)-N2-[4-(4-morpholinyl)phenyl]-1H-purine-2,6-diamine | $^1$H NMR (CD$_3$OD): δ 8.20 (s, 1H), 7.72 (s, 1H), 7.54 (d, J=9.0 Hz, 1H), 6.92 (d, J=9.0 Hz, 1H), 6.32 (m, 2H), 4.58 (m, 1H), 3.83 (t, J=4.8 Hz, 4H), 3.07 (t, J=4.8 Hz, 4H), 2.97 (s, 1H), 2.85 (s, 1H), 2.66 (d, J=7.8 Hz, 1H), 2.34 (d, J=9.3 Hz, 1H), 1.62 (d, J=9.3 Hz, 1H); LC-MS: purity: 100.00%; MS (m/e) : 447.09 (M + H)$^+$ |
| 150 | 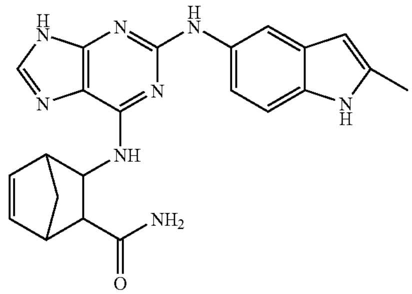 | Racemic-(2-exo,3-exo-)-N6-(3-aminocarbonylbicyclo[2.2.1]hept-5-en-2-yl)-N2-(2-methyl-1H-indol-5-yl)-1H-purine-2,6-diamine | $^1$H NMR (CD$_3$OD): δ 8.27 (s, 1H), 7.68 (m, 1H), 7.16 (d, J=8.4 Hz, 1H), 7.11 (d, J=8.4 Hz, 1H), 6.31 (m, 2H), 6.04 (s, 1H), 4.57 (m, 1H), 2.96 (s, 1H), 2.86 (s, 1H), 2.63 (d, J=7.8 Hz, 1H), 2.40 (s, 3H), 2.33 (d, J=8.7 Hz, 1H), 1.62 (d, J=9.0 Hz, 1H); LC-MS: purity: 100.00%; MS (m/e): 415.75 (M + H)$^+$ |
| 151 | 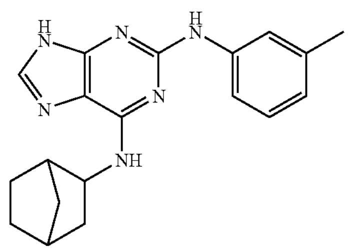 | Racemic-(2-exo)-N6-(bicyclo[2.2.1]hept-2-yl)-N2-(3-methyl)phenyl-1H-purine-2,6-diamine | $^1$H NMR (DMSO-d$_6$): δ 9.13 (s, 1H), 8.17 (s, 1H), 7.58 (d, J=7.5 Hz, 1H), 7.50 (s, 1H), 7.14 (d, J=7.5 Hz, 1H), 6.75 (d, J=7.5 Hz, 1H), 3.96 (s, 1H), 3.40 (brs, 2H), 2.28 (s, 3H), 1.78-1.47 (m, 5H), 1.31-1.14 (m, 3H); LC-MS: purity: 98.80%; MS (m/e): 335.52 (M + H)$^+$ |
| 152 | 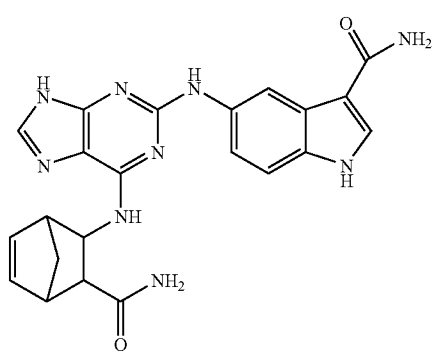 | Racemic-(2-exo,3-exo-)-N6-(3-aminocarbonylbicyclo[2.2.1]hept-5-en-2-yl)-N2-(3-aminocarbonyl-1H-indol-5-yl)-1H-purine-2,6-diamine | $^1$H NMR (CD$_3$OD): δ 8.39 (s, 1H), 8.14 (m, 1H), 7.89 (s, 1H), 7.77 (m, 1H), 7.34 (m, 2H), 6.29-6.21 (m, 2H), 4.62 (m, 1H), 2.94 (s, 1H), 2.81 (s, 1H), 2.68 (d, J=8.7 Hz, 1H), 2.65 (s, 1H), 2.36 (d, J=9.0 Hz, 1H), 1.61 (d, J=8.7 Hz, 1H); LC-MS: purity: 100.00%; MS (m/e): 444.04 (M + H)$^+$ |
| 153 | 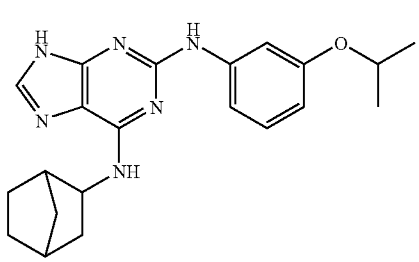 | Racemic-(2-exo)-N6-(bicyclo[2.2.1]hept-2-yl)-N2-(3-isopropoxy)phenyl-1H-purine-2,6-diamine | $^1$H NMR (CD$_3$OD): δ 8.17 (s, 1H), 7.33 (s, 1H), 7.18 (m, 2H), 6.50 (m, 1H), 4.52 (pent, J=6.0 Hz, 1H), 2.38 (m, 1H), 2.31 (s, 1H), 1.92-1.84 (m, 1H), 1.58-1.36 (m, 5H), 1.30 (d, J=6.0 Hz, 6H), 1.23-1.17 (m, 2H); LC-MS: purity: 100.00%; MS (m/e): 379.06 (M + H)$^+$ |

TABLE 1-continued

| No. | Structure | Name | Spectroscopic Data |
|---|---|---|---|
| 154 | 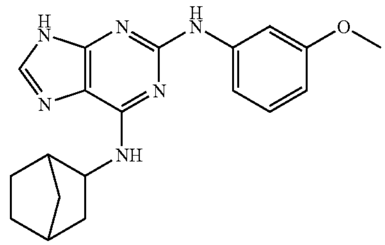 | Racemic-(2-exo)-N6-(bicyclo[2.2.1]hept-2-yl)-N2-(3-methoxy)phenyl-1H-purine-2,6-diamine | $^1$H NMR (CD$_3$OD): δ 8.10 (s, 1H), 7.33 (s, 1H), 7.68 (m, 1H), 7.41 (m, 1H), 7.23 (d, J=8.1 Hz, 1H), 7.15 (t, J=7.8 Hz, 1H), 6.50 (dd, J=2.4, 7.8 Hz, 1H), 4.06 (m, 1H), 3.79 (s, 3H), 2.41 (m, 1H), 2.34 (s, 1H), 1.94-1.87 (m, 1H), 1.60-1.36 (m, 5H), 1.27-1.21 (m, 2H); LC-MS: purity: 100.00%; MS (m/e): 351.02 (M + H)$^+$ |
| 155 | 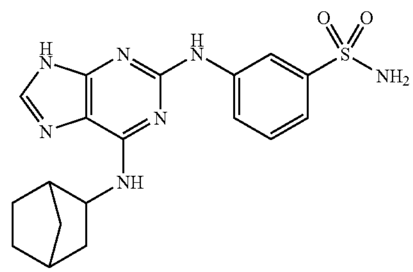 | Racemic-(2-exo)-N6-(bicyclo[2.2.1]hept-2-yl)-N2-(3-aminosulfonyl)phenyl-1H-purine-2,6-diamine | $^1$H NMR (CD$_3$OD): δ 8.26 (m, 1H), 8.09 (s, 1H), 7.91 (d, J=7.8 Hz, 1H), 7.42 (m, 2H), 7.35 (t, J=7.8 Hz, 1H), 3.99 (m, 1H), 2.37 (m, 1H), 2.32 (s, 1H), 1.94-1.86 (m, 1H), 1.58-1.32 (m, 5H), 1.25-1.22 (m, 2H); LC-MS: purity: 100.00%; MS (m/e): 399.97 (M + H)$^+$ |
| 156 | 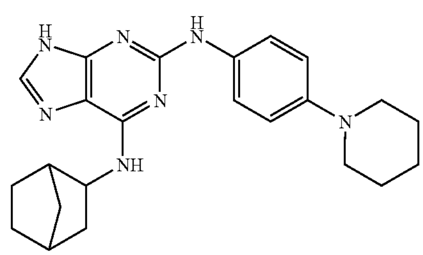 | Racemic-(2-exo)-N6-(bicyclo[2.2.1]hept-2-yl)-N2-(4-piperidino)phenyl-1H-purine-2,6-diamine | $^1$H NMR (CD$_3$OD): δ 8.07 (s, 1H), 7.78 (d, J=8.4 Hz, 2H), 7.35 (d, J=8.4 Hz, 2H), 3.99 (m, 1H), 3.39 (m, 4H), 2.44 (m, 1H), 2.37 (s, 1H), 1.89 (m, 4H), 1.71-1.24 (m, 10H); LC-MS: purity: 100.00%; MS (m/e): 404.07 (M + H)$^+$ |
| 157 | 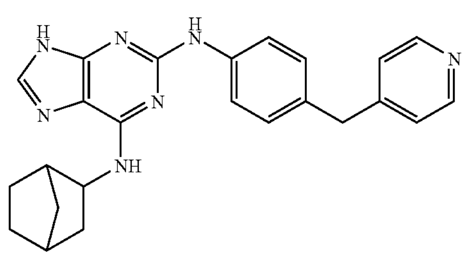 | Racemic-(2-exo)-N6-(bicyclo[2.2.1]hept-2-yl)-N2-[4-(4-pyridinylmethyl)phenyl]-1H-purine-2,6-diamine | $^1$H NMR (CD$_3$OD): δ 8.35 (m, 1H), 8.11 (s, 1H), 7.60 (d, J=7.8 Hz, 1H), 7.13 (d, J=6.0 Hz, 1H), 7.05 (d, J=7.8 Hz, 1H), 3.99 (m, 1H), 3.92 (s, 2H), 2.41 (m, 1H), 2.32 (s, 1H), 1.86-1.80 (m, 1H), 1.60-1.13 (m, 5H); LC-MS: purity: 100.00%; MS (m/e): 412.05 (M + H)$^+$ |
| 158 | 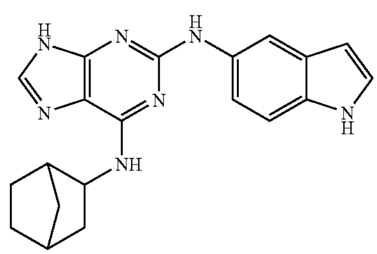 | Racemic-(2-exo)-N6-(bicyclo[2.2.1]hept-2-yl)-N2-(1H-indol-5-yl)-1H-purine-2,6-diamine | $^1$H NMR (DMSO-d$_6$): δ 8.46 (brs, 1H), 8.06 (s, 1H), 7.75 (m, 1H), 7.32 (m, 1H), 7.22 (m, 2H), 7.06 (brs, 1H), 6.27 (m, 1H), 4.02 (m, 1H), 3.30 (s, 1H), 2.30 (s, 1H), 2.24 (s, 1H), 1.74-1.09 (m, 7H); LC-MS: purity: 100.00%; MS (m/e): 360.06 (M + H)$^+$ |

TABLE 1-continued

| No. | Structure | Name | Spectroscopic Data |
|---|---|---|---|
| 159 | 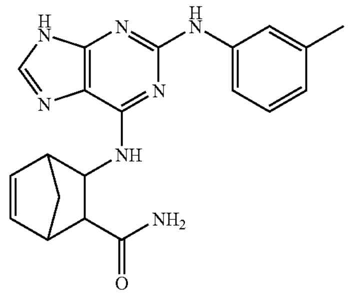 | Racemic-(2-exo,3-exo)-N4-(3-aminocarbonylbicyclo[2.2.1]hept-5-en-2-yl)-N2-(3-methyl)phenyl-1H-pyrrolo[2,3-d]pyrimidine-2,4-diamine | $^1$H NMR (CD$_3$OD): δ 8.22 (s, 1H), 7.49 (s, 1H), 7.47 (d, J=8.4 Hz, 1H), 7.12 (t, J=7.5 Hz, 1H), 6.78 (s, 1H), 6.76 (d, J=7.5 Hz, 1H), 6.33 (m, 2H), 4.52 (m, 1H), 2.96 (s, 1H), 2.89 (s, 1H), 2.66 (d, J=8.1 Hz, 1H), 2.32 (s, 3H), 1.59 (d, J=9.0 Hz, 1H); LC-MS: purity: 100.00%; MS (m/e): 375.04 (M + H)$^+$ |
| 160 | 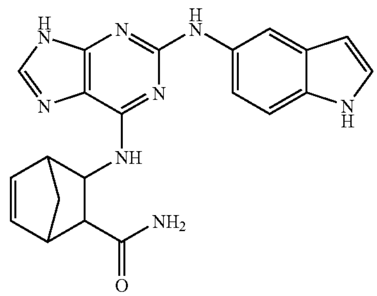 | Racemic-(2-exo,3-exo)-N4-(3-aminocarbonylbicyclo[2.2.1]hept-5-en-2-yl)-N2-(1H-indol-5-yl)-1H-pyrrolo[2,3-d]pyrimidine-2,4-diamine | $^1$H NMR (CD$_3$OD): δ 8.33 (s, 1H), 7.79 (m, 1H), 7.37 (d, J=8.7 Hz, 1H), 7.25 (d, J=3.0 Hz, 1H),7.16 (dd, J=2.4, 8.7 Hz, 1H), 6.77 (d, J=3.6 Hz, 1H), 6.41 (d, J=3.3 Hz, 1H), 6.31 (m, 2H), 4.45 (d, J=7.8 Hz, 1H), 2.96 (s, 1H), 2.91 (s, 1H), 2.61 (d, J=8.1 Hz, 1H), 2.31 (d, J=8.7 Hz, 1H), 1.59 (d, J=9.0 Hz, 1H); LC-MS: purity: 100.00%; MS (m/e) : 400.04 (M + H)$^+$ |
| 161 | 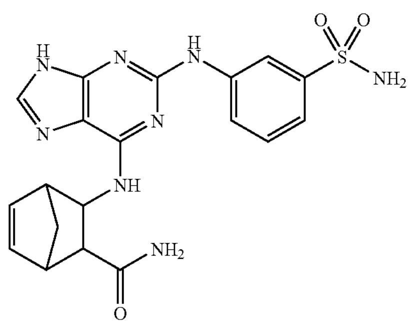 | Racemic-(2-exo,3-exo)-N4-(3-aminocarbonylbicyclo[2.2.1]hept-5-en-2-yl)-N2-(3-aminosulfonyl)phenyl-1H-pyrrolo[2,3-d]pyrimidine-2,4-diamine | $^1$H NMR (CD$_3$OD): δ 8.42 (m, 1H), 8.17 (s, 1H), 7.83 (m, 1H), 7.40 (m, 2H), 6.80 d, J=3.6 Hz, 1H), 6.37 (d, J=3.6 Hz, 1H), 6.33 (m, 2H), 4.55 (m, 1H), 2.96 (s, 1H), 2.86 (s, 1H), 2.74 (d, J=8.1 Hz, 1H), 2.33 (d, J=8.7 Hz, 1H), 1.58 (d, J=9.3 Hz, 1H); LC-MS: purity: 100.00%; MS (m/e): 440.01 (M + H)$^+$ |
| 162 | 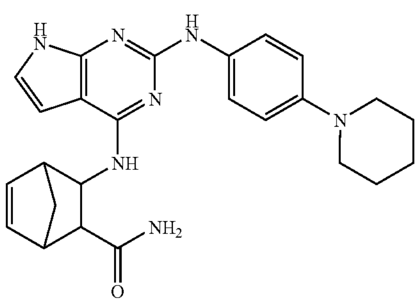 | Racemic-(2-exo,3-exo)-N4-(3-aminocarbonylbicyclo[2.2.1]hept-5-en-2-yl)-N2-(4-piperidino)phenyl-1H-pyrrolo[2,3-d]pyrimidine-2,4-diamine | $^1$H NMR (CD$_3$OD): δ 8.19 (m, 2H), 7.61 (d, J=9.0 Hz, 2H), 7.11 (d, J=8.4 Hz, 2H), 6.79 (m,1H), 6.35 (m, 2H), 4.43 (m, 1H), 3.23 (m, 4H), 2.97 (s, 1H), 2.90 (s, 1H), 2.65 (d, J=8.1 Hz, 1H), 2.29 (d, J=9.0 Hz, 1H), 1.84-1.57 (m, 7H); LC-MS: purity: 100.00%; MS (m/e) : 444.54 (M + H)$^+$ |
| 163 | 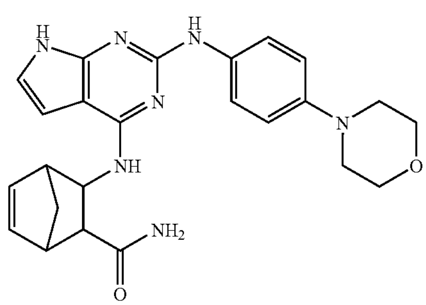 | Racemic-(2-exo,3-exo)-N4-(3-aminocarbonylbicyclo[2.2.1]hept-5-en-2-yl)-N2-[4-(4-morpholinyl)phenyl]-1H-pyrrolo[2,3-d]pyriinidine-2,4-diamine | $^1$H NMR (CD$_3$OD): δ 8.19 (m, 2H), 7.50 (d, J=9.0 Hz, 2H), 6.96 (d, J=9.0 Hz, 2H), 6.80 (d, J=3.6 Hz,1H), 6.38 (d, J=3.6 Hz, 1H), 6.32 (m, 2H), 4.41 (d, J=7.8 Hz, 1H), 3.84 (t, J=4.8 Hz, 4H), 3.10 (t, J=4.8 Hz, 4H), 2.97 (s, 1H), 2.90 (s, 1H), 2.63 (d, J=9.3 Hz, 1H), 2.29 (d, J=8.7 Hz, 1H), 1.59 (d, J=9.0 Hz, 1H); LC-MS: purity: 100.00%; MS (m/e) : 446.49 (M + H)$^+$ |

TABLE 1-continued

| No. | Structure | Name | Spectroscopic Data |
|---|---|---|---|
| 164 | 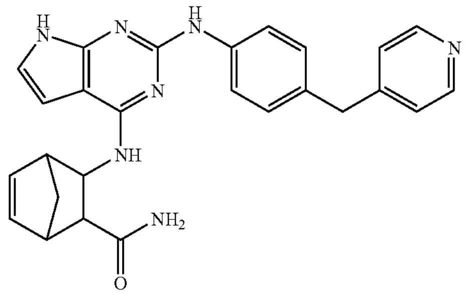 | Racemic-(2-exo,3-exo)-N4-(3-aminocarbonylbicyclo[2.2.1]hept-5-en-2-yl)-N2-[4-(4-pyridinylmethyl)phenyl]-1H-pyrrolo[2,3-d]pyrimidine-2,4-diamine | $^1$H NMR (CD$_3$OD): δ 8.40 (m, 1H), 8.13 (m, 2H), 7.61 (d, J=8.4 Hz, 2H), 7.30 (m, 1H), 7.15 (d, J=8.4 Hz, 2H), 6.80 (d, J=3.3 Hz, 1H), 6.36 (d, J=3.3 Hz, 1H), 6.28 (m, 2H), 4.41 (d, J=7.5 Hz, 1H), 4.00 (s, 2H), 2.97 (s, 1H), 2.90 (s, 1H), 2.62 (d, J=9.3 Hz, 1H), 2.29 (d, J=8.7 Hz, 1H), 1.58 (d, J=9.3 Hz, 1H); LC-MS: purity: 100.00%; MS (m/e) : 452.53 (M + H)$^+$ |
| 165 | 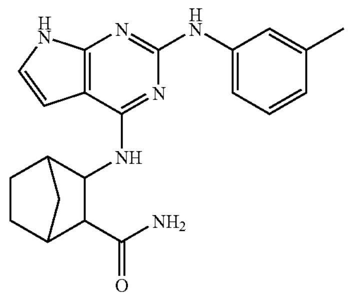 | Racemic-(2-exo,3-exo)-N4-(3-aminocarbonylbicyclo[2.2.1]hept-2-yl)-N2-(3-methyl)phenyl-1H-pyrrolo[2,3-d]pyrimidine-2,4-diamine | $^1$H NMR (CD$_3$OD): δ 8.22 (s, 1H), 7.66 (s, 1H), 7.47 (m, 1H), 7.13 (t, J=7.8 Hz, 1H), 6.76 (d, J=3.3 Hz, 1H), 6.30 (d, J=3.3 Hz, 1H), 4.47 (d, J=8.4 Hz, 1H), 2.68 (d, J=8.4 Hz, 1H), 2.44 (m, 1H), 2.39 (s, 1H), 2.33 (s, 3H), 2.12 (d, J=10.2 Hz, 1H), 1.70-1.28 (m, 5H);LC-MS: purity: 99.70%; MS (m/e): 377.84 (M + H)$^+$ |
| 166 | 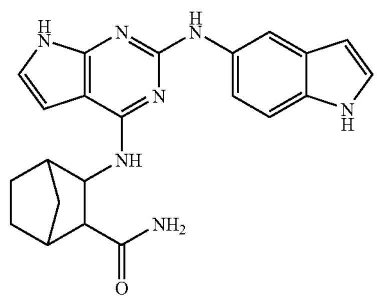 | Racemic (2-exo-3-exo)-N4-(3-aminocarbonylbicyclo[2.2.1]hept-2-yl)-N2-(1H-indol-5-yl)-1H-pyrrolo[2,3-d]pyrimidine-2,4-diamine | $^1$H NMR (CD$_3$OD): δ 8.31 (s, 1H), 7.80 (m, 1H), 7.38 (d, J=8.4 Hz, 1H), 7.25 (d, J=3.3 Hz, 1H), 7.16 (dd, J=2.1, 8.4 Hz, 1H), 6.77 (d, J=3.3 Hz, 1H), 6.41 (dd, J=3.3, 5.7 Hz, 1H), 4.48 (d, J=7.8 Hz, 1H), 2.70 (d, J=8.4 Hz, 1H), 2.42 (s, 1H), 2.36 (m, 1H), 2.19 (d, J=10.2 Hz, 1H), 1.69-1.30 (m, 5H); LC-MS: purity: 99.92%; MS (m/e) : 402.90 (M + H)$^+$ |
| 167 | 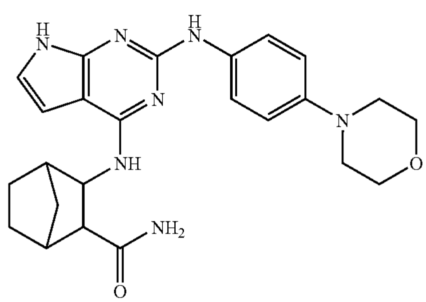 | Racemic (2-exo-3-exo)-N4-(3-aminocarbonylbicyclo[2.2.1]hept-2-yl)-N2-[4-morpholin-4-yl)phenyl]-1H-pyrrolo[2,3-d]pyrimidine-2,4-diamine | $^1$H NMR (CD$_3$OD): δ 8.21 (s, 1H), 7.52 (d, J=9.0 Hz, 2H), 6.95 (d, J=9.0 Hz, 2H), 6.78 (d, J=3.6 Hz, 1H), 6.34 (d, J=3.6 Hz, 1H), 4.45 (d, J=7.8 Hz, 1H), 3.84 (t, J=4.8 Hz, 4H), 3.09 (t, J=4.8 Hz, 4H), 2.71 (d, J=8.4 Hz, 1H), 2.43 (s, 1H), 2.35 (m, 1H), 2.15 (d, J=10.2 Hz, 1H), 1.67-1.29 (m, 5H); LC-MS: purity: 100.00%; MS (m/e): 448.13 (M + H)$^+$ |
| 168 | 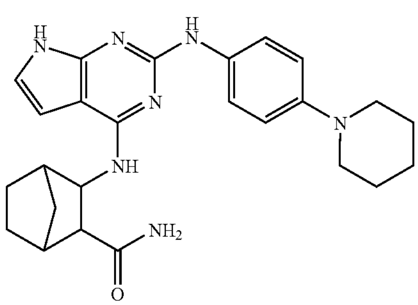 | Racemic-(2-exo,3-exo) N4-(3-aminocarbonylbicyclo[2.2.1]hept-2-yl)-N2-[4-(piperidin-1-yl)phenyl]-1H-pyrrol[2,3-d]pyrimidine-2,4-diamine | $^1$H NMR (CD$_3$OD): δ 8.24 (s, 1H), 7.53 (d, J=8.4 Hz, 1H), 7.08 (d, J=8.7 Hz, 2H), 6.79 (d, J=9.0 Hz, 1H), 6.75 (d, J=3.3 Hz, 1H), 6.38 (d, J=3.3 Hz, 1H), 4.57 (d, J=7.8 Hz, 1H), 3.19 (m, 2H), 3.02 (t, J=4.8 Hz, 2H), 2.85 (d, J=7.8 Hz, 1H), 2.52 (s, 1H), 2.38 (m, 1H), 2.26 (d, J=9.9 Hz, 1H), 1.80-1.36 (m, 11H); LC-MS: purity: 100.00%; MS (m/e) : 446.18 (M + H)$^+$ |

TABLE 1-continued

| No. | Structure | Name | Spectroscopic Data |
|---|---|---|---|
| 169 | 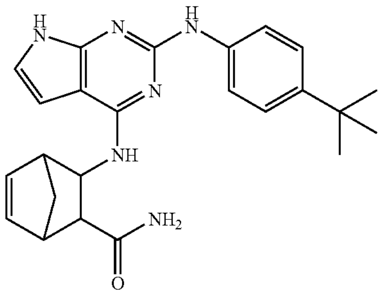 | Racemic-(2-exo,3-exo)-N4-(3-aminocarbonylbicyclo[2.2.1]hept-5-en-2-yl)-N2-[4-(1,1-dimethylethyl)phenyl]-1H-pyrrolo[2,3-d]pyrimidine-2,4-diamine | $^1$H NMR (CD$_3$OD): δ 8.20 (s, 1H), 7.60 (m, 1H), 7.52 (m, 1H), 7.19 (t, J=7.8 Hz, 1H), 7.03-7.00 (m, 1H), 7.78 (d, J=3.6 Hz,1H), 6.36 (d, J=3.6 Hz, 1H), 6.31 (m, 2H), 4.52 (d, J=6.6 Hz, 1H), 2.96 (s, 1H), 2.88 (s, 1H), 2.67 (d, J=9.3 Hz, 1H), 2.31 (d, J=9.0 Hz, 1H), 1.59 (d, J=9.0 Hz, 1H), 1.34 (s, 9H); LC-MS: purity: 100.00%; MS (m/e): 417.57 (M + H)$^+$ |
| 170 | 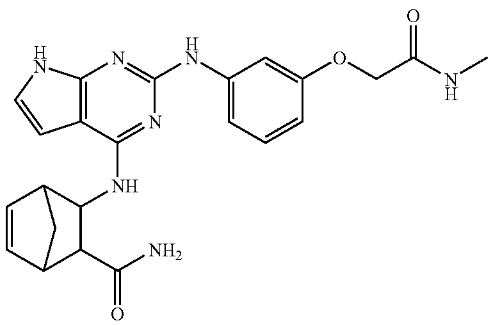 | Racemic-(2-exo,3-exo)-N4-(3-aminocarbonylbicyclo[2.2.1]hept-5-en-2-yl)-N2-[3-[2-(methylamino)-2-oxoethoxy]phenyl]]-1H-pyrrolo[2,3-d]pyrimidine-2,4-diamine | $^1$H NMR (CD$_3$OD): δ 8.13 (s, 1H), 7.60 (m, 1H), 7.18 (d, J=4.8 Hz, 1H), 6.80 (d, J=3.3 Hz,1H), 6.57 (m, 1H), 6.36 (d, J=3.3 Hz, 1H), 6.32 (m, 2H), 4.50 (m, 3H), 2.96 (s, 1H), 2.89 (s, 1H), 2.82 (s, 3H), 2.67 (d, J=9.3 Hz, 1H), 2.31 (d, J=9.0 Hz, 1H), 1.59 (d, J=9.3 Hz, 1H); LC-MS: purity: 100.00%; MS (m/e) : 448.51 (M + H)$^+$ |
| 171 | 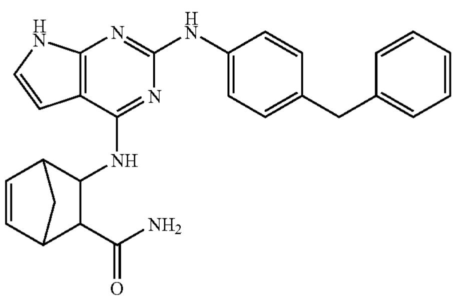 | Racemic-(2-exo,3-exo)-N4-(3-aminocarbonylbicyclo[2.2.1]hept-5-en-2-yl)-N2-(4-phenylmethyl)phenyl-1H-pyrrolo[2,3-d]pyrimidine-2,4-diamine | $^1$H NMR (CD$_3$OD): δ 8.15 (s, 1H), 7.68 (s, 1H), 7.52 (d, J=8.4 Hz, 2H), 7.25-7.09 (m, 5H), 6.76 (d, J=3.6 Hz,1H), 6.34 (d, J=3.6 Hz, 1H), 6.27 (m, 2H), 4.36 (d, J=6.9 Hz, 1H), 3.93 (s, 2H), 2.97 (s, 1H), 2.89 (s, 1H), 2.59 (d, J=7.5 Hz, 1H), 2.23 (d, J=9.3 Hz, 1H), 1.57 (d, J=9.6 Hz, 1H); LC-MS: purity: 100.00%; MS (m/e) : 451.56 (M + H)$^+$ |
| 172 | 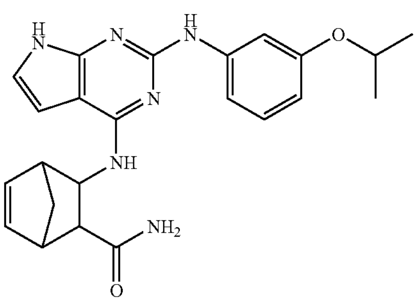 | Racemic-(2-exo,3-exo)-N4-(3-aminocarbonylbicyclo[2.2.1]hept-5-en-2-yl)-N2-(3-isopropoxy)phenyl-1H-pyrrolo[2,3-d]pyrimidine-2,4-diamine | $^1$H NMR (CD$_3$OD): δ 8.17 (s, 1H), 7.51 (m, 1H), 7.13 (t, J=8.1 Hz, 1H), 7.06-7.03 (m, 1H), 6.80 (d, J=3.6 Hz,1H), 6.51 (dd, J=2.4, 8.1 Hz, 1H), 6.42 (dd, J=3.0, 5.4 Hz, 1H), 6.32 (m, 2H), 4.61 (pent, J=6.0 Hz, 1H), 4.48 (d, J=7.8 Hz, 1H), 2.97 (s, 1H), 2.91 (s, 1H), 2.68 (d, J=7.8 Hz, 1H), 2.31 (d, J=8.7 Hz, 1H), 1.59 (d, J=9.0 Hz, 1H), 1.32 (d, J=6.0 Hz, 6H); LC-MS: purity: 100.00%; MS (m/e) : 419.56 (M + H)$^+$ |
| 173 | 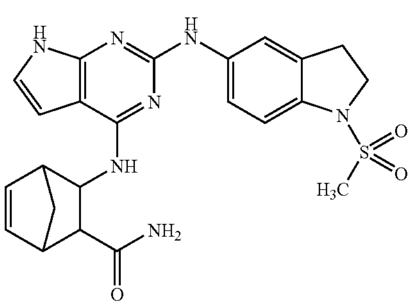 | Racemic-(2-exo,3-exo)-N4-(3-aminocarbonylbicyclo[2.2.1]hept-5-en-2-yl)-N2-(2,3-dihydro-1-methylsulfonyl-1H-indol-5-yl)-1H-pyrrolo[2,3-d]pyrimidine-2,4-diamine | $^1$H NMR (CD$_3$OD): δ 8.19 (s, 1H), 7.65 (m, 1H), 7.42 (dd, J=2.1, 8.7 Hz, 1H), 7.23 (d, J=8.7 Hz, 1H), 6.79 d, J=3.3 Hz, 1H), 6.36 (d, J=3.3 Hz, 1H), 6.32 (m, 2H), 4.44 (d, J=8.7 Hz, 1H), 3.96 (t, J=8.4 Hz, 2H), 2.97 (s, 1H), 2.88 (s, 1H), 2.65 (d, J=8.7 Hz, 1H), 2.31 (d, J=9.3 Hz, 1H), 1.58 (d, J=9.3 Hz, 1H); LC-MS: purity: 100.00%; MS (m/e) : 480.98 (M + H)$^+$ |

TABLE 2

| No. | Structure | Name | Spectroscopic Data |
|---|---|---|---|
| 174 | 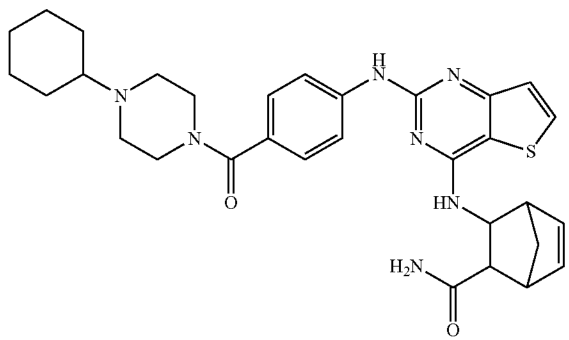 | 3-(2-(4-(4-cyclohexylpiperazine-1-carbonyl)phenylamino)thieno[3,2-d]pyrimidin-4-ylamino)bicyclo[2.2.1]hept-5-ene-2-carboxamide | MS (ES) 572.06 (M + H), 570.02 (M − H). |
| 175 | 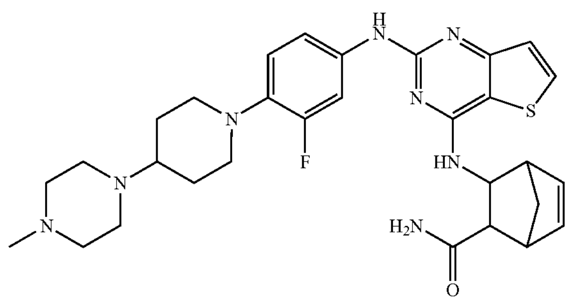 | 3-(2-(3-fluoro-4-(4-(4-methylpiperazin-1-yl)piperidin-1-yl)phenylamino)thieno[3,2-d]pyrimidin-4-ylamino)bicyclo[2.2.1]hept-5-ene-2-carboxamide | MS (ES) 577.10 (M + H), 575.06 (M − H). |
| 176 | 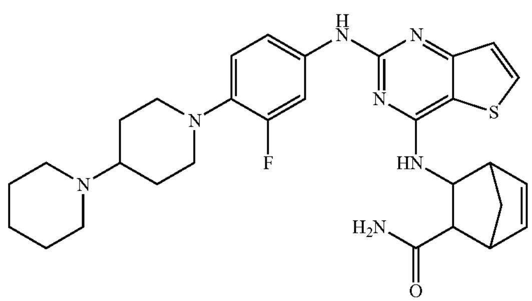 | 3-(2-(4-(1,4'-bipiperidin-1'-yl)-3-fluorophenylamino)thieno[3,2-d]pyrimidin-4-ylamino)bicyclo[2.2.1]hept-5-ene-2-carboxamide | MS (ES) 562.27 (M + H), 560.35 (M − H). |

TABLE 2-continued

| No. | Structure | Name | Spectroscopic Data |
|---|---|---|---|
| 177 | 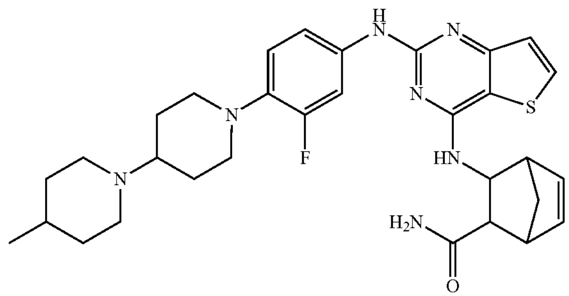 | 3-(2-(3-fluoro-4-(4-methyl-1,4-bipiperidin-1-yl)phenylamino)thieno[3,2-d]pyrimidin-4-ylamino)bicyclo[2.2.1]hept-5-ene-2-carboxamide | MS (ES) 576.13 (M + H), 574.08 (M − H). |
| 178 | 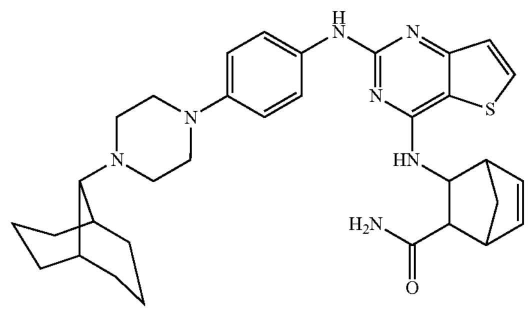 | 3-(2-(4-(4-(bicyclo[3.3.1]nonan-9-yl)piperazin-1-yl)phenylamino)thieno[3,2-d]pyrimidin-4-ylamino)bicyclo[2.2.1]hept-5-ene-2-carboxamide | MS (ES) 584.16 (M + H), 582.12 (M − H). |
| 179 | 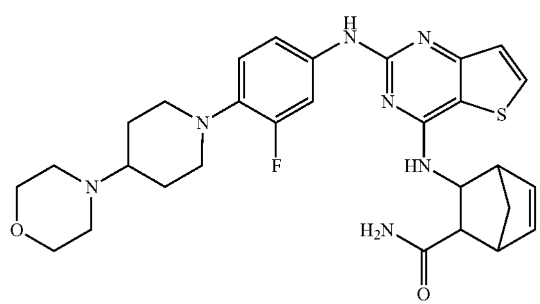 | 3-(2-(3-fluoro-4-(4-morpholinopiperidin-1-yl)phenylamino)thieno[3,2-d]pyrimidin-4-ylamino)bicyclo[2.2.1]hept-5-ene-2-carboxamide | MS (ES) 564.05 (M + H), 562.02 (M − H). |

TABLE 2-continued

| No. | Structure | Name | Spectroscopic Data |
|---|---|---|---|
| 180 | 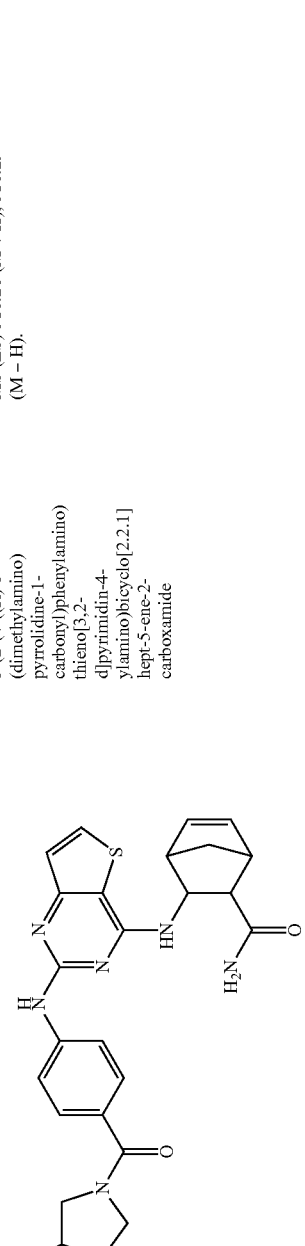 | 3-(2-(4-((R)-3-(dimethylamino)pyrrolidine-1-carbonyl)phenylamino)thieno[3,2-d]pyrimidin-4-ylamino)bicyclo[2.2.1]hept-5-ene-2-carboxamide | MS (ES) 518.20 (M + H), 516.29 (M − H). |
| 181 | 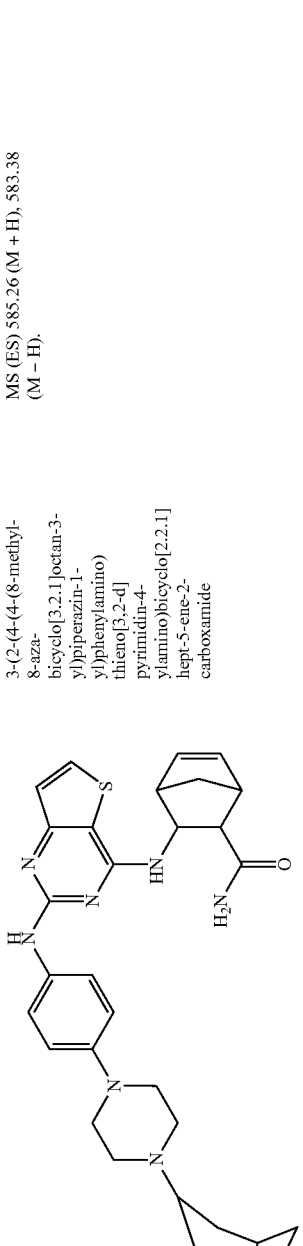 | 3-(2-(4-(8-methyl-8-aza-bicyclo[3.2.1]octan-3-yl)piperazin-1-yl)phenylamino)thieno[3,2-d]pyrimidin-4-ylamino)bicyclo[2.2.1]hept-5-ene-2-carboxamide | MS (ES) 585.26 (M + H), 583.38 (M − H). |
| 182 | 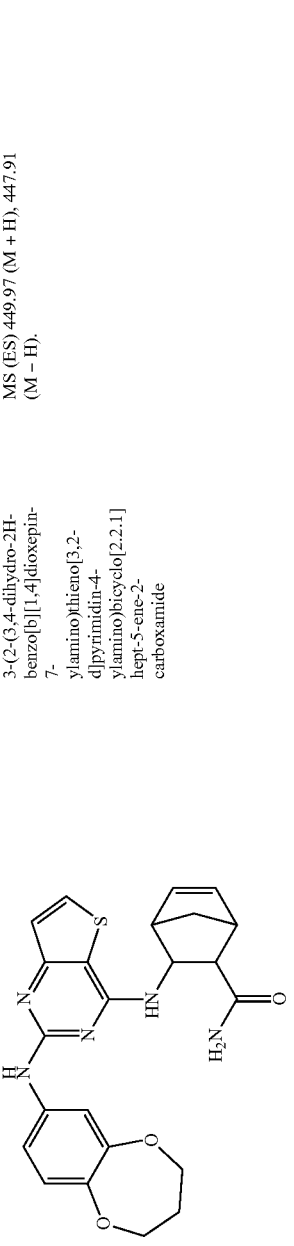 | 3-(2-(3,4-dihydro-2H-benzo[b][1,4]dioxepin-7-ylamino)thieno[3,2-d]pyrimidin-4-ylamino)bicyclo[2.2.1]hept-5-ene-2-carboxamide | MS (ES) 449.97 (M + H), 447.91 (M − H). |

TABLE 2-continued

| No. | Structure | Name | Spectroscopic Data |
|---|---|---|---|
| 183 | 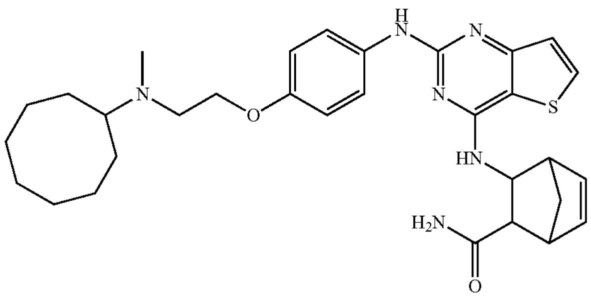 | 3-(2-(4-(2-(cyclooctyl(methyl)amino)ethoxy)phenylamino)thieno[3,2-d]pyrimidin-4-ylamino)bicyclo[2.2.1]hept-5-ene-2-carboxamide | MS (ES) 561.09 (M + H), 559.06 (M − H). |
| 184 | 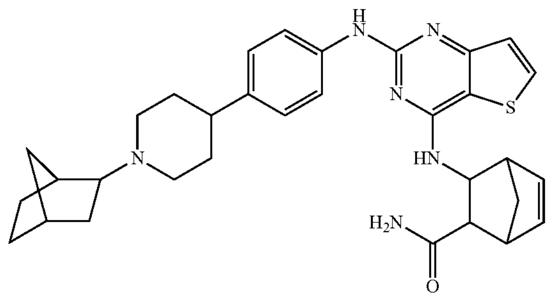 | 3-(2-(4-(1-(bicyclo[2.2.1]heptan-2-yl)piperidin-4-yl)phenylamino)thieno[3,2-d]pyrimidin-4-ylamino)bicyclo[2.2.1]hept-5-ene-2-carboxamide | MS (ES) 555.35 (M + H), 553.23 (M − H). |
| 185 | 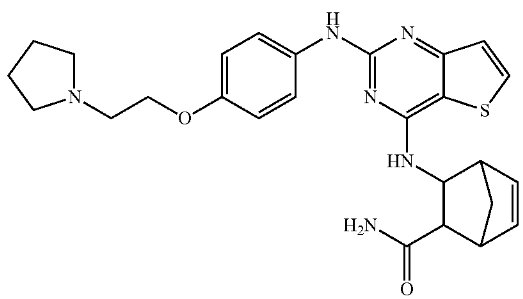 | 3-(2-(4-(2-(pyrrolidin-1-yl)ethoxy)phenylamino)-6,7-dihydro-5H-cyclopenta[d]pyrimidin-4-ylamino)bicyclo[2.2.1]hept-5-ene-2-carboxamide | $^1$H NMR (CDCl$_3$, 300 MHz) 11.20 (s, 1H), 8.25 (d, 1H), 7.58 (d, 2H), 6.78 (m, 3H), 6.29 (m, 1H), 6.20 (m, 1H), 5.87 (s, 1H), 4.29 (m, 2H), 4.09 (t, 1H), 3.46 (m, 6H), 3.02 (s, 1H), 2.89 (m, 3H), 2.54 (m, 4H), 2.17 (m, 6H), 1.53 (d, 1H) ppm; MS (ES) 475.17 (M + H) |

| No. | Structure | Name | Spectroscopic Data |
|---|---|---|---|
| 186 | 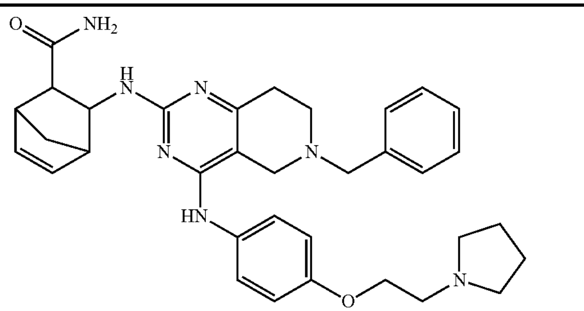 | 3-(6-benzyl-4-(4-(2-(pyrrolidin-1-yl)ethoxy)phenylamino)-5,6,7,8-tetrahydropyrido[4,3-d]pyrimidin-2-ylamino)bicyclo[2.2.1]hept-5-ene-2-carboxamide | $^1$H NMR (MeOD$_4$, 300 MHz) 7.55 (d, 2H), 7.30-7.42 (m, 5H), 7.02 (d, 2H), 6.35 (m, 1H), 6.23 (m, 1H), 4.33 (t, 2H), 4.09 (d, 1H), 3.87 (s, 2H), 3.65 (t, 2H), 3.44 (m, 4H), 3.31 (m, 2H), 2.98 (s, 1H), 2.86 (m, 2H), 2.74 (m, 2H), 2.55 (d, 1H), 2.13 (m, 3H), 2.06 (d, 1H), 1.51 (d, 1H) ppm; MS (ES) 580.26 (M + H). |
| 187 | 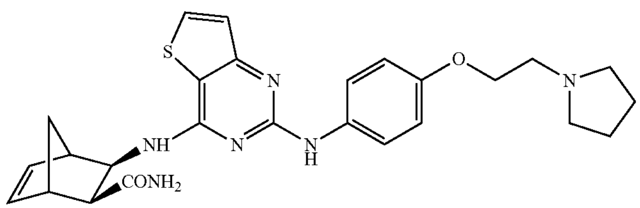 | (2S,3R)-3-(2-(4-(2-(pyrrolidin-1-yl)ethoxy)phenylamino)thieno[3,2-d]pyrimidin-4-ylamino)bicyclo[2.2.1]hept-5-ene-2-carboxamide | $^1$H NMR (CDCl$_3$, 300 MHz) 8.04 (s, 1H), 7.72 (d, 1H), 7.49 (d, 2H), 7.20 (d, 1H), 6.78 (d, 2H), 6.23 (m, 1H), 6.11 (m, 1H), 4.21 (t, 2H), 4.08 (d, 1H), 3.47 (t, 2H), 3.55 (m, 4H), 2.94 (s, 1H), 2.88 (s, 1H), 2.46 (d, 1H), 2.03 (m, 5H), 1.47 (d, 1H) ppm; MS (ES) 491 (M + H). |
| 188 | 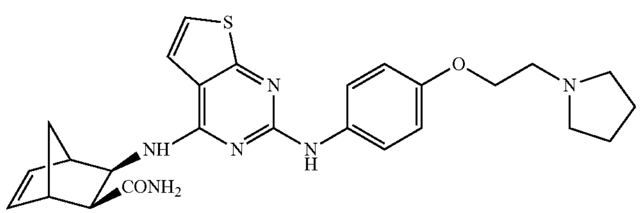 | (2S,3R)-3-(2-(4-(2-(pyrrolidin-1-yl)ethoxy)phenylamino)thieno[2,3-d]pyrimidin-4-ylamino)bicyclo[2.2.1]hept-5-ene-2-carboxamide | $^1$H NMR (CDCl$_3$/MeOD, 300 MHz) 8.20 (s, 1H), 7.49 (d, 2H), 7.24 (br s, 1H), 6.97 (d, 1H), 6.83 (d, 1H), 6.75 (d, 2H), 6.24 (m, 1H), 6.18 (m, 1H), 4.19 (m, 3H), 3.44 (m, 2H), 3.35 (m, 4H), 2.95 (s, 1H), 2.85 (s, 1H), 2.04 (m, 5H), 1.49 (d, 1H) ppm; MS (ES) 491 (M + H). |

TABLE 2-continued

| No. | Structure | Name | Spectroscopic Data |
|---|---|---|---|
| 189 | 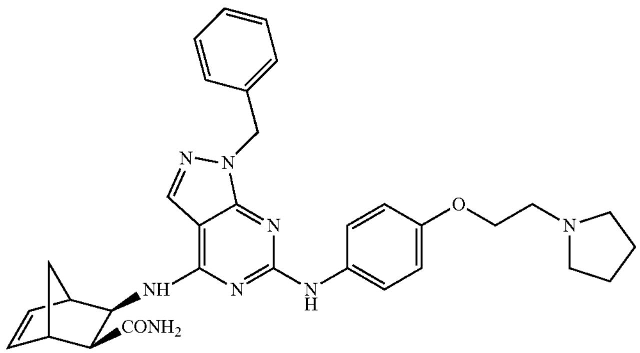 | (2S,3R)-3-(1-benzyl-6-(4-(2-(pyrrolidin-1-yl)ethoxy)phenylamino)-1H-pyrazolo[3,4-d]pyrimidin-4-ylamino)bicyclo[2.2.1]hept-5-ene-2-carboxamide | ¹H NMR (CDCl₃, 300 MHz) 7.61 (s, 1H), 7.58 (d, 2H), 7.24 (s, 5H), 6.93 (d, 1H), 6.81 (d, 2H), 6.20 (m, 2H), 5.60 (br s, 1H), 5.25 (s, 2H), 4.36 (m, 1H), 4.07 (m, 2H), 2.96 (s, 1H), 2.88 (m, 2H), 2.66 (m, 4H), 2.46 (d, 1H), 2.17 (d, 1H), 1.80 (m, 5H), 1.54 (d, 1H) ppm; ¹³C NMR (CDCl₃, 75 MHz) 176.53, 161.64, 158.85, 157.31, 154.20, 138.92, 137.45, 135.69, 134.29, 128.93, 128.42, 128.26, 122.62, 121.33, 115.13, 99.69, 67.81, 57.40, 55.44, 54.88, 53.08, 48.45, 47.35, 46.43, 44.92, 32.21, 30.99, 23.97; MS (ES) 565 (M + H). |
| 190 | 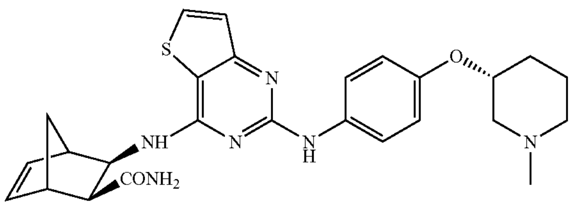 | 3-(2-(4-((R)-1-methylpiperidin-3-yloxy)phenylamino)thieno[3,2-d]pyrimidin-4-ylamino)bicyclo[2.2.1]hept-5-ene-2-carboxamide | ¹H NMR (CDCl₃/MeOD, 300 MHz) 8.34 (s, 2H), 7.64 (d, 1H), 7.49 (d, 2H), 7.10 (d, 1H), 6.83 (d, 2H), 6.21 (m, 1H), 6.17 (m, 1H), 4.42 (m, 1H), 4.18 (d, 1H), 3.10 (m, 1H), 2.88 (m, 3H), 2.40-2.60 (m, 3H), 2.50 (s, 3H), 2.05 (d, 1H), 1.89 (m, 2H), 1.40-1.80 (m, 3H) ppm; MS (ES) 491 (M + H). |
| 191 | 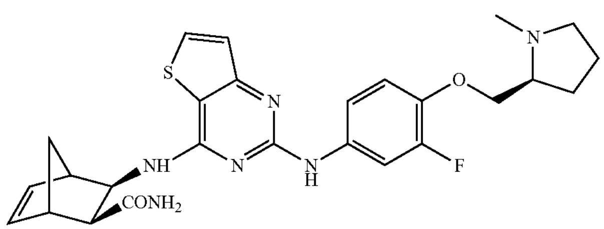 | 3-(2-(3-fluoro-4-(((S)-1-methylpyrrolidin-2-yl)methoxy)phenylamino)thieno[3,2-d]pyrimidin-4-ylamino)bicyclo[2.2.1]hept-5-ene-2-carboxamide | ¹H NMR (CDCl₃/MeOD, 300 MHz) 8.39 (s, 1H), 7.77 (m, 1H), 7.66 (d, 1H), 7.14 (m, 2H), 6.92 (m, 1H), 6.35 (m, 1H), 6.29 (m, 1H), 4.30 (m, 2H), 4.18 (m, 1H), 3.50 (m, 1H), 3.35 (m, 1H), 2.99 (m, 2H), 2.75 (m, 4H), 2.51 (d, 1H), 1.95-2.25 (m, 5H), 1.56 (d, 1H) ppm; MS (ES) 509 (M + H). |

TABLE 2-continued

| No. | Structure | Name | Spectroscopic Data |
|---|---|---|---|
| 192 | 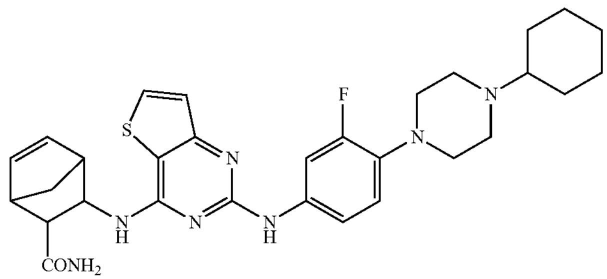 | 3-(2-(4-(4-cyclohexylpiperazin-1-yl)-3-fluorophenylamino)thieno[3,2-d]pyrimidin-4-ylamino)bicyclo[2.2.1]hept-5-ene-2-carboxamide | $^1$H NMR (DMSO-d$_6$, 300 MHz) 10.00 (br s, 1H), 9.49 (br s, 1H), 8.95 (br s, 1H), 8.12 (d, 1H), 7.75-7.85 (m, 2H), 7.29 (m, 2H), 7.21 (d, 1H), 7.08 (t, H), 6.34 (m, 1H), 6.29 (m, 1H), 4.18 (t, 1H), 3.48 (m, 4H), 3.23 (m, 2H), 3.04 (m, 2H), 2.93 (s, 1H), 2.48 (m, 2H), 2.11 (m, 2H), 1.84 (m, 2H), 1.25-1.45 (m, 5H), 1.13 (m, 1H) ppm; MS (ES) 562.08 (M + H). |
| 193 | 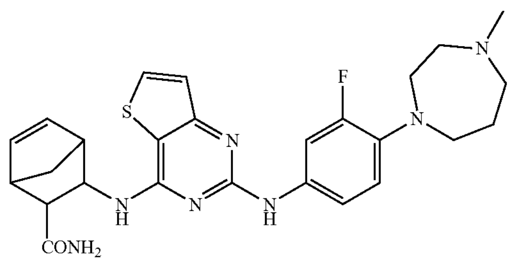 | 3-(2-(3-fluoro-4-(4-methyl-1,4-diazepan-1-yl)phenylamino)thieno[3,2-d]pyrimidin-4-ylamino)bicyclo[2.2.1]hept-5-ene-2-carboxamide | $^1$H NMR (CDCl$_3$/MeOD, 300 MHz) 8.12 (s, 1H), 7.70 (d, 1H), 7.60 (m, 1H), 7.15 (d, 1H), 7.05 (m, 1H), 6.73 (t, 1H), 6.23 (m, 2H), 4.08 (d, 1H), 3.36 (m, 6H), 3.21 (m, 2H), 2.93 (m, 2H), 2.81 (s, 3H), 2.49 (d, 1H), 2.25 (m, 2H), 1.96 (d, 1H), 1.46 (d, 1H) ppm; MS (ES) 508.16 (M + H). |
| 194 | 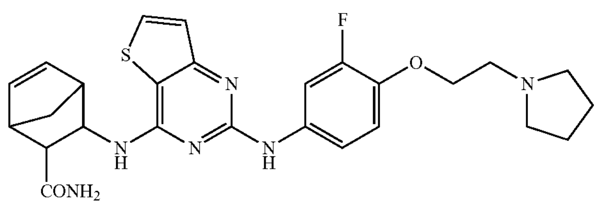 | 3-(2-(3-fluoro-4-(2-(pyrrolidin-1-yl)ethoxy)phenylamino)thieno[3,2-d]pyrimidin-4-ylamino)bicyclo[2.2.1]hept-5-ene-2-carboxamide | $^1$H NMR (CDCl$_3$, 300 MHz) 8.21 (s, 2H), 7.68 (m, 2H), 7.08 (m, 2H), 6.84 (t, 1H), 6.21 (s, 2H), 4.24 (m, 2H), 4.10 (d, 1H), 3.42 (m, 2H), 3.31 (m, 4H), 2.91 (m, 2H), 2.46 (d, 1H), 1.97 (m, 5H), 1.46 (d, 1H) ppm; MS (ES) 509.19 (M + H). |
| 195 | 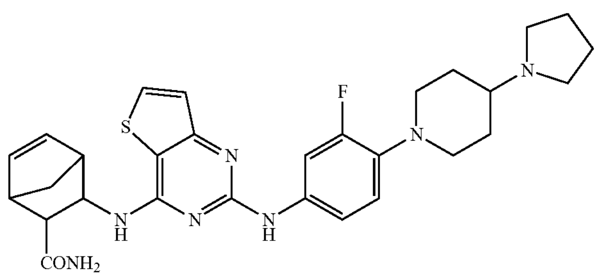 | 3-(2-(3-fluoro-4-(4-(pyrrolidin-1-yl)piperidin-1-yl)phenylamino)thieno[3,2-d]pyrimidin-4-ylamino)bicyclo[2.2.1]hept-5-ene-2-carboxamide | $^1$H NMR (DMSO-d$_6$, 300 MHz) 10.50 (br s, 1H), 10.10 (br s, 1H), 9.15 (br s, 1H), 8.14 (d, 1H), 7.74 (m, 2H), 7.25 (m, 2H), 7.04 (t, 1H), 6.36 (m, 1H), 6.28 (m, 1H), 4.17 (t, 1H), 3.52 (m, 2H), 3.39 (m, 2H), 3.20 (m, 1H), 3.07 (m, 2H), 2.93 (s, 2H), 2.63 (m, 2H), 2.51 (m, 4H), 2.11 (m, 2H), 1.78-2.00 (m, 5H), 1.44 (d, 2H) ppm; MS (ES) 548.35 (M + H). |

| No. | Structure | Name | Spectroscopic Data |
|---|---|---|---|
| 196 | 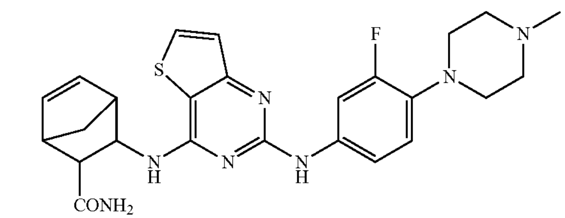 | 3-(2-(3-fluoro-4-(4-methylpiperazin-1-yl)phenylamino)thieno[3,2-d]pyrimidin-4-ylamino)bicyclo[2.2.1]hept-5-ene-2-carboxamide | $^1$H NMR (CDCl$_3$/MeOD, 300 MHz) 7.71 (d, 1H), 7.55 (d, 1H), 7.17 (m, 2H), 6.85 (t, 1H), 6.19 (m, 2H), 4.09 (d, 1H), 3.15-3.30 (m, 8H), 2.90 (s, 2H), 2.73 (s, 3H), 2.43 (d, 1H), 1.97 (d, 1H), 1.45 (d, 1H); MS(ES) 494.21 (M + H). |
| 197 | 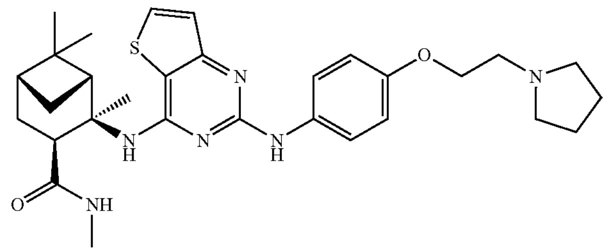 | (1S,2R,3S,5R)-N,2,6,6-tetramethyl-2-(4-(2-(pyrrolidin-1-yl)ethoxy)phenylamino)thieno[3,2-d]pyrimidin-4-ylamino)bicyclo[3.1.1]heptane-3-carboxamide | $^1$H NMR (CDCl$_3$, 300 MHz) 9.08 (br s, 1H), 8.63 (s, 1H), 7.62 (d, 1H), 7.39 (d, 2H), 7.18 (d, 1H), 6.82 (d, 2H), 6.70 (br s, 1H), 4.23 (m, 2H), 3.27 (m, 2H), 3.12 (m, 4H), 3.01 (m, 2H), 2.87 (m, 4H), 2.14 (m, 3H), 2.00 (m, 5H), 1.59 (s, 3H), 1.24 (s, 3H), 1.06 (s, 3H) ppm; $^{13}$C NMR (CDCl$_3$, 75 MHz) 176.18, 169.83, 156.06, 154.68, 154.62, 132.76, 132.59, 124.16, 120.04, 114.72, 109.73, 65.44, 61.20, 54.64, 54.56, 50.36, 47.15, 40.40, 38.73, 32.86, 30.21, 29.48, 27.22, 26.19, 23.80, 23.67; MS(ES) 549.29 (M + H). |
| 198 | 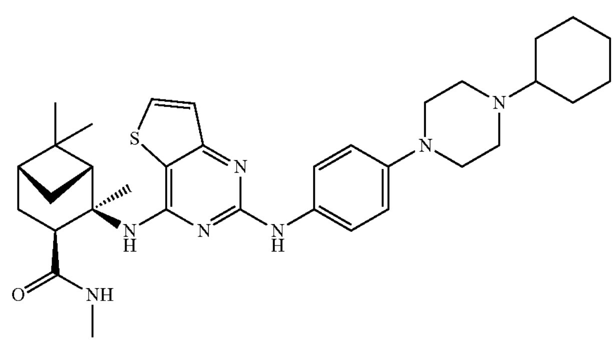 | (1S,2R,3S,5R)-2-(2-(4-(4-cyclohexylpiperazin-1-yl)phenylamino)thieno[3,2-d]pyrimidin-4-ylamino)-N,2,6,6-tetramethylbicyclo[3.1.1]heptane-3-carboxamide | $^1$H NMR (CDCl$_3$, 300 MHz) 11.24 (s, 1H), 9.73 (s, 1H), 7.68 (d, 1H), 7.37 (d, 2H), 7.25 (d, 1H), 6.86 (d, 2H), 6.50 (br s, 1H), 3.20-3.50 (m, 8H), 3.15 (m, 1H), 2.85 (m, 5H), 2.16 (m, 4H), 1.94 (m, 4H), 1.74 (m, 1H), 1.52 (s, 3H), 1.20-1.50 (m, 3H), 1.30 (m, 5H), 1.04 (s, 1H) ppm; MS (ES) 602 (M + H). |

| No. | Structure | Name | Spectroscopic Data |
|---|---|---|---|
| 199 | 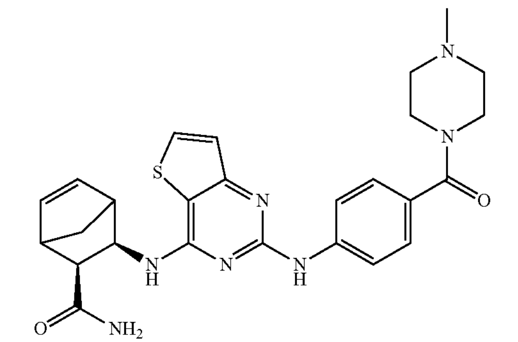 | (2S,3R)-3-(2-(4-(4-methylpiperazine-1-carbonyl)phenylamino)thieno[3,2-d]pyrimidin-4-ylamino)bicyclo[2.2.1]hept-5-ene-2-carboxamide | $^1$H NMR (CDCl$_3$/MeOD$_4$, 300 MHz) 7.75 (m, 3H), 7.32 (d, 2H), 7.26 (d, 1H), 6.27 (m, 1H), 6.18 (m, 1H), 4.15 (d, 1H), 3.22 (s, 3H), 3.11 (m, 6H), 2.95 (m, 2H), 2.73 (m, 2H), 2.48 (d, 1H), 2.01 (d, 1H), 1.50 (d, 1H) ppm; MS (ES) 504.20 (M + H). |
| 200 | 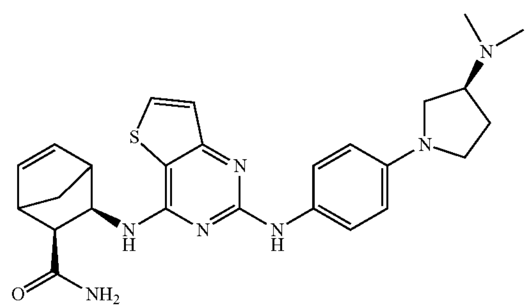 | (2S,3R)-3-(2-(4-((S)-3-(dimethylamino)pyrrolidin-1-yl)phenylamino)thieno[3,2-d]pyrimidin-4-ylamino)bicyclo[2.2.1]hept-5-ene-2-carboxamide | $^1$H NMR (CDCl$_3$/MeOD$_4$, 300 MHz) 8.15 (s, 2H), 7.65 (d, 1H), 7.32 (d, 2H), 7.09 (d, 1H), 6.43 (d, 2H), 6.16 (m, 1H), 6.08 (m, 1H), 3.53 (m, 1H), 3.99 (m, 3H), 3.19 (m, 2H), 2.87 (d, 2H), 2.60 (s, 6H), 2.38 (d, 1H), 2.28 (m, 1H), 2.14 (m, 1H), 1.96 (d, 1H), 1.43 (d, 1H) ppm; MS(ES) 490.12 (M + H). |
| 201 | 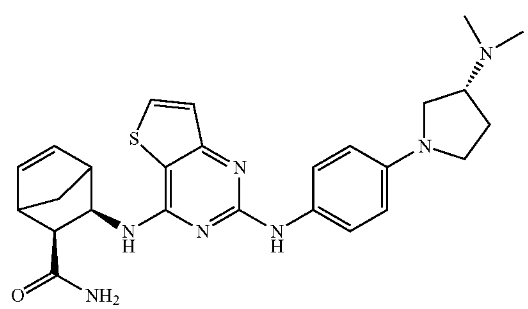 | (2S,3S)-3-(2-(4-((R)-3-(dimethylamino)pyrrolidin-1-yl)phenylamino)thieno[3,2-d]pyrimidin-4-ylamino)bicyclo[2.2.1]hept-5-ene-2-carboxamide | $^1$H NMR (CDCl$_3$/MeOD$_4$, 300 MHz) 8.22 (s, 2H), 7.72 (d, 1H), 7.44 (d, 2H), 7.20 (d, 1H), 6.54 (d, 2H), 6.28 (m, 1H), 6.19 (m, 1H), 4.20 (m, 1H), 2.40-2.80 (m, 4H), 3.31 (m, 1H), 2.96 (m, 2H), 2.67 (s, 6H), 2.50 (m, 1H), 2.36 (m, 1H), 2.22 (m, 1H), 2.09 (m, 1H), 1.56 (m, 1H) ppm; MS (ES) 490.31 (M + H). |

| No. | Structure | Name | Spectroscopic Data |
|---|---|---|---|
| 202 | 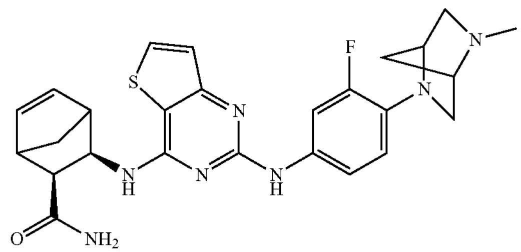 | (2S,3R)-3-(2-(3-fluoro-4-(5-methyl-2,5-diaza-bicyclo[2.2.1]heptan-2-yl)phenylamino)thieno[3,2-d]pyrimidin-4-ylamino)bicyclo[2.2.1]hept-5-ene-2-carboxamide | $^1$H NMR (CDCl$_3$/MeOD, 300 MHz) 8.34 (s, 2H), 7.73 (m, 2H), 6.63 (t, 1H), 6.31 (m, 2H), 4.46 (m, 1H), 4.29 (m, 1H), 4.14 (m, 1H), 3.63 (m, 2H), 3.30-3.40 (m, 2H), 3.00 (m, 2H), 2.78 (s, 3H), 2.57 (d, 1H), 2.16 (m, 3H), 1.57 (d, 1H) ppm; MS (ES) 506.12 (M + H). |
| 203 | 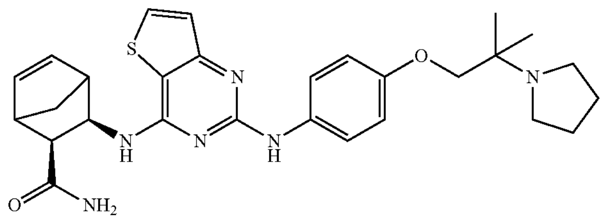 | (2S,3R)-3-(2-(4-(2-methyl-2-(pyrrolidin-1-yl)propoxy)phenylamino)thieno[3,2-d]pyrimidin-4-ylamino)bicyclo[2.2.1]hept-5-ene-2-carboxamide | $^1$H-NMR (DMSO-d$_6$, 300 MHz) 8.92 (s, 1H), 8.12 (s, 1H), 7.94 (d, J=5.1 Hz, 1H), 7.73 (d, J=9.0 Hz, 2H), 7.66 (s, 2H), 7.22 (s, 1H), 7.10 (d, J=5.4 Hz, 1H), 6.93 (d, J=8.7 Hz, 2H), 6.33 (s, 2H), 4.26 (t, J=6.6 Hz, 1H), 3.99 (s, 2H), 3.19 (s, 4H), 2.87 (d, J=9.6 Hz, 2H), 2.55 (d, J=6.6 Hz, 1H), 2.17 (d, J=8.7 Hz, 1H), 1.86 (s, 4H), 1.43 (d, J=8.1 Hz, 1H), 1.34 (s, 6H) ppm; MS (ES) 519.12 (M + H), 517.26 (M − H). |
| 204 | 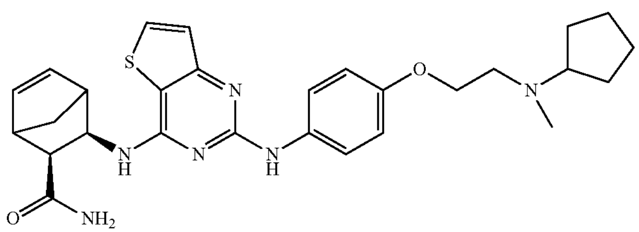 | (2S,3R)-3-(2-(4-(2-(cyclopentyl(methyl)amino)ethoxy)phenylamino)thieno[3,2-d]pyrimidin-4-ylamino)bicyclo[2.2.1]hept-5-ene-2-carboxamide | $^1$H-NMR (DMSO-d$_6$, 300 MHz) 8.98 (s, 1H), 8.11 (s, 1H), 7.95 (d, J=5.4 Hz, 1H), 7.73 (d, J=9.0 Hz, 2H), 7.66 (s, 2H), 7.23 (s, 1H), 7.11 (d, J=5.4 Hz, 1H), 6.93 (d, J=9.0 Hz, 2H), 6.32 (s, 2H), 4.26-4.12 (m, 4H), 3.69 (t, 1H), 3.55 (s, 2H), 2.89 (s, 2H), 2.85 (s, 3H), 2.53 (d, J=8.4 Hz, 1H), 2.16 (d, J=8.7 Hz, 1H), 1.71 (s, 4H), 1.55 (s, 2H), 1.43 (d, J=8.7 Hz, 1H) ppm; MS (ES) 519.03 (M + H), 516.91 (M − H). |

TABLE 2-continued

| No. | Structure | Name | Spectroscopic Data |
|---|---|---|---|
| 205 | 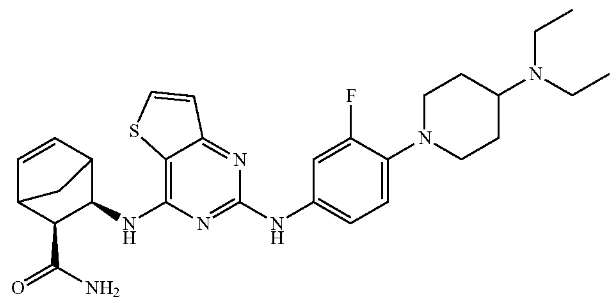 | (2S,3R)-3-(2-(4-(4-(diethylamino)piperidin-1-yl)-3-fluorophenylamino)thieno[3,2-d]pyrimidin-4-ylamino)bicyclo[2.2.1]hept-5-ene-2-carboxamide | $^1$H-NMR (DMSO-d$_6$, 300 MHz) 9.10 (s, 1H), 8.13 (s, 1H), 7.95 (d, J=5.4 Hz, 1H), 7.89 (d, J=15.6 Hz, 1H), 7.54 (d, J=6.9 Hz, 1H), 7.68 (s, 1H), 7.32 (d, J=8.4 Hz, 1H), 7.24 (s, 1H), 7.13 (d, J=5.1 Hz, 1H), 6.93 (t, J=8.7 Hz, 1H), 6.34 (s, 2H), 4.25 (t, J=7.5 Hz, 1H), 2.89 (s, 4H), 2.80 (m, 4H), 2.64 (t, J=11.4 Hz, 3H), 2.55 (d, J=7.8 Hz, 1H), 2.16 (d, J=8.4 Hz, 1H), 1.87 (d, J=11.1 Hz, 2H), 1.72-1.61 (m, 2H), 1.42 (d, J=8.4 Hz, 1H), 1.09 (t, J=7.2 Hz, 6H) ppm; MS (ES) 550.19 (M + H), 548.32 (M − H). |
| 206 | 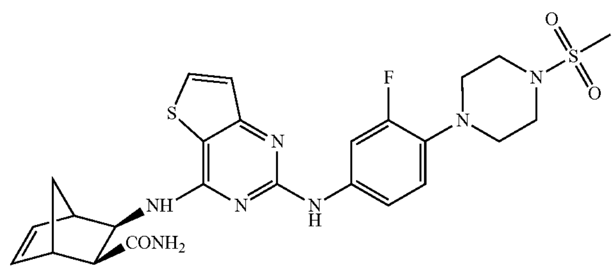 | (2S,3R)-3-(2-(3-fluoro-4-(4-(methylsulfonyl)piperazin-1-yl)phenylamino)thieno[3,2-d]pyrimidin-4-ylamino)bicyclo[2.2.1]hept-5-ene-2-carboxamide | $^1$H-NMR (DMSO-d$_6$, 300 MHz) 9.23 (s, 1H), 8.11 (s Hz, 1H), 7.97 (d, J=5.1 Hz, 1H), 7.90 (d, J=15.3 Hz, 1H), 7.69 (s, 1H), 7.34 (d, J=8.7 Hz, 1H), 7.25 (t, J=5.1 Hz, 1H), 7.15 (d, J=5.1 Hz, 1H), 6.99 (t, J=9.3 Hz, 1H), 6.34 (s, 2H), 4.25 (t, J=7.5 Hz, 1H), 3.26 (s, 4H), 3.03 (s, 4H), 2.93 (s, 3H), 2.89 (s, 2H), 2.56 (d, J=8.1 Hz, 1H), 2.16 (d, J=8.4 Hz, 1H), 1.43 (d, J=8.4 Hz, 1H) ppm; MS (ES) 558.12 (M + H), 556.25 (M − H). |
| 207 | 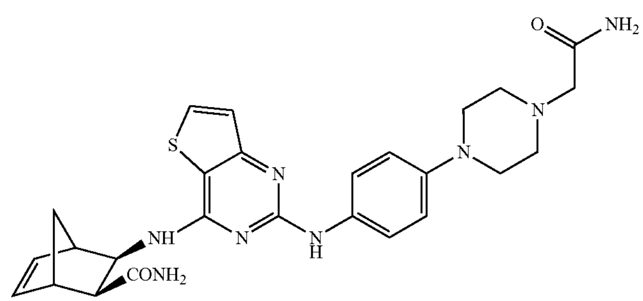 | (2S,3R)-3-(2-(4-(4-(2-amino-2-oxoethyl)piperazin-1-yl)phenylamino)thieno[3,2-d]pyrimidin-4-ylamino)bicyclo[2.2.1]hept-5-ene-2-carboxamide | $^1$H-NMR (DMSO-d$_6$, 300 MHz) 8.80 (s, 1H), 8.11 (s, 1H), 7.92 (d, J=5.4 Hz, 1H), 7.68-7.60 (m, 4H), 7.21 (s, 2H), 7.09 (d, J=4.5 Hz, 1H), 6.33 (s, 2H), 4.26 (t, J=8.1 Hz, 1H), 3.24 (s, 2H), 3.13 (s, 4H), 2.87 (d, J=9.0 Hz, 2H), 2.74 (s, 4H), 2.55 (d, J=7.8 Hz, 1H), 2.17 (d, J=8.7 Hz, 1H), 1.42 (d, J=8.4 Hz, 1H) ppm; MS (ES) 519.17 (M + H), 517.30 (M − H). |

| No. | Structure | Name | Spectroscopic Data |
|---|---|---|---|
| 208 | 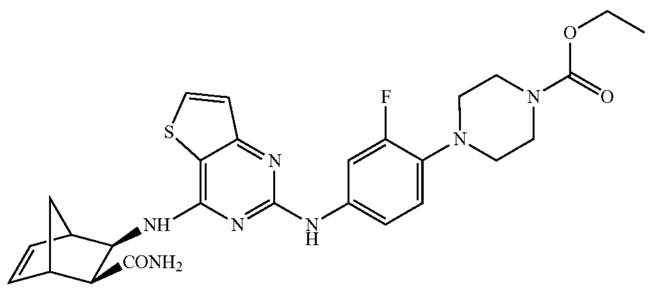 | ethyl 4-(4-((2R,3S)-3-carbamoylbicyclo[2.2.1]hept-5-en-2-ylamino)thieno[3,2-d]pyrimidin-2-ylamino)-2-fluorophenyl)piperazine-1-carboxylate | 1H-NMR (DMSO-d6, 300 MHz) 9.39 (s, 1H), 8.03 (m, 1H), 7.85 (d, J=15.0 Hz, 1H), 7.71 (s, 1H), 7.31-7.25 (m, 2H), 7.20-7.16 (m, 1H), 7.10-6.95 (m, 1H), 6.34 (s, 2H), 4.23 (t, J=7.5 Hz, 1H), 4.10-4.02 (m, 2H), 3.51 (s, 4H), 2.90 (s, 6H), 2.56 (d, J=8.1 Hz, 1H), 2.15 (d, J=7.5 Hz, 1H), 1.43 (d, J=6.9 Hz, 1H), 1.23-1.16 (m, 3H) ppm; MS (ES) 552.18(M + H), 550.26 (M − H). |
| 209 | 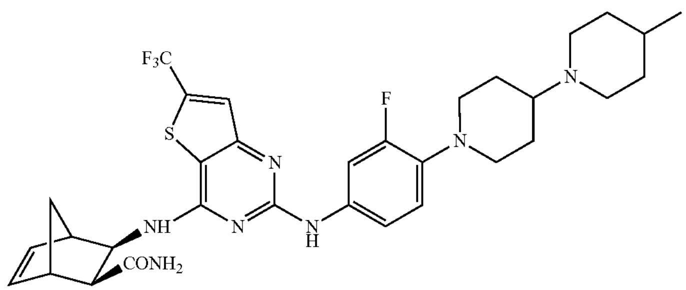 | (2S,3R)-3-(2-(3-fluoro-4-(4-methyl-1,4'-bipiperidin-1'-yl)phenylamino)-6-(trifluoromethyl)thieno[3,2-d]pyrimidin-4-ylamino)bicyclo[2.2.1]hept-5-ene-2-carboxamide | 1H-NMR (DMSO-d6, 300 MHz) 9.27 (s, 1H), 8.11 (s, 1H), 7.86 (d, J=15.3 Hz, 1H), 7.79 (s, 1H), 7.52 (s, 1H), 7.32 (d, J=9.0 Hz, 1H), 7.14 (s, 1H), 6.95 (t, J=9.0 Hz, 1H), 6.33 (s, 2H), 4.27 (t, J=7.2 Hz, 1H), 3.23 (d, J=11.4 Hz, 4H), 2.95 (m, 1H), 2.88 (d, J=4.5, Hz 2H), 2.72-2.58 (m, 4H), 2.54 (d, J=8.1 Hz, 1H), 2.21 (d, J=8.1 Hz, 1H), 1.98 (d, J=10.2 Hz, 2H), 1.77-170 (m, 4H), 1.52 (m, 1H), 1.43 (d, J=8.4 Hz, 1H), 1.33-1.23 (m, 2H), 0.91 (d, J=6.0 Hz, 3H) ppm; MS (ES) 644.15 (M + H), 642.32 (M − H). |
| 210 | 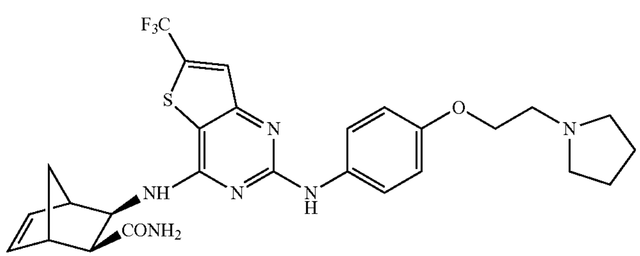 | (2S,3R)-3-(2-(4-(2-(pyrrolidin-1-yl)ethoxy)phenylamino)-6-(trifluoromethyl)thieno[3,2-d]pyrimidin-4-ylamino)bicyclo[2.2.1]hept-5-ene-2-carboxamide | 1H-NMR (DMSO-d6, 300 MHz) 9.05 (s, 1H), 8.02 (d, J=6.3 Hz, 1H), 7.72 (d, J=10.5 Hz, 2H), 7.68 (s, 1H), 7.49 (s, 1H), 7.12 (s, 1H), 6.90 (d, J=9.0 Hz, 2H), 6.30 (s, 2H), 4.27 (t, J=7.5 Hz, 1H), 4.15 (m, 2H), 3.30 (s, 2H), 3.08 (s, 4H), 2.87 (d, J=10.2 Hz, 2H), 2.54 (d, J=7.8 Hz, 1H), 2.20 (d, J=8.4 Hz, 1H), 1.86 (s, 4H), 1.43 (d, J=8.4 Hz, 1H) ppm; MS (ES) 559.07 (M + H), 557.28 (M − H). |

TABLE 2-continued

| No. | Structure | Name | Spectroscopic Data |
|---|---|---|---|
| 211 | 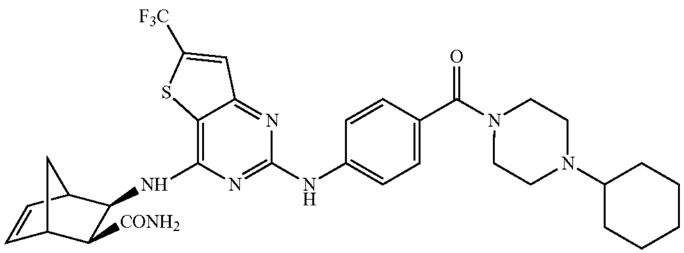 | (2S,3R)-3-(2-(4-(4-cyclohexylpiperazine-1-carbonyl)phenylamino)-6-(trifluoromethyl)thieno[3,2-d]pyrimidin-4-ylamino)bicyclo[2.2.1]hept-5-ene-2-carboxamide | $^1$H-NMR (DMSO-d$_6$, 300 MHz) 9.45 (s, 1H), 8.14 (d, J=6.9 Hz, 1H), 8.11 (s, 1H), 7.85 (d, J=8.4 Hz, 2H), 7.82 (s, 1H), 7.48 (s, 1H), 7.30 (d, J=8.7 Hz, 2H), 7.09 (s, 1H), 6.32 (s, 2H), 4.32 (t, J=8.1 Hz, 1H), 3.49 (s,2H), 3.31 (m, 4H), 2.88 (d, J=8.4 Hz, 2H), 2.56 (d, J=6.6 Hz, 2H), 2.25 (d, J=9.0 Hz, 2H), 1.75 (s, 4H), 1.56 (d, J=11.7 Hz, 1H),1.44 (d, J=8.1 Hz, 1H), 1.00-1.30 (m, 6H) ppm; MS (ES) 640.22 (M + H), 638.34 (M − H). |
| 212 | 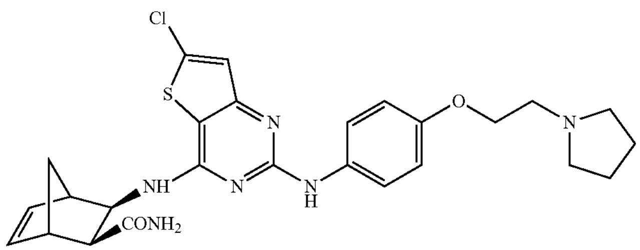 | (2S,3R)-3-(6-chloro-2-(4-(2-(pyrrolidin-1-yl)ethoxy)phenylamino)thieno[3,2-d]pyrimidin-4-ylamino)bicyclo[2.2.1]hept-5-ene-2-carboxamide | $^1$H-NMR (DMSO-d$_6$, 300 MHz) 9.16 (s, 1H), 8.03 (s, 1H), 7.94 (d, J=6.3 Hz, 1H), 7.78 (d, J=9.3 Hz, 2H), 7.61 (s, 1H), 7.20 (s, 1H), 6.90 (d, J=9.0 Hz, 2H), 6.32 (s, 2H), 4.20 (m, 3H), 3.42 (s, 2H), 3.21 (s, 4H), 2.87 (d, J=9.3 Hz, 2H), 2.54 (d, J=8.4 Hz, 1H), 2.17 (d, J=8.1 Hz, 1H), 1.90 (s, 4H), 1.43 (d, J=7.8 Hz, 1H) ppm; MS (ES) 525.10 (M + H), 523.22 (M − H). |
| 213 | 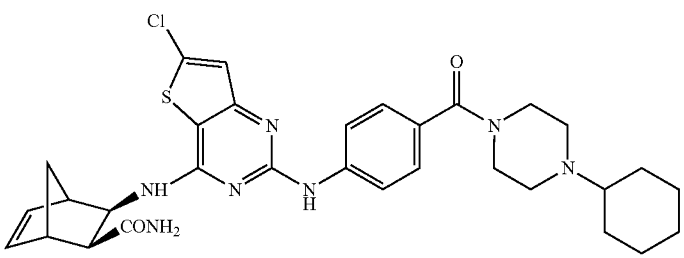 | (2S,3R)-3-(6-chloro-2-(4-(4-cyclohexylpiperazine-1-carbonyl)phenylamino)thieno[3,2-d]pyrimidin-4-ylamino)bicyclo[2.2.1]hept-5-ene-2-carboxamide | $^1$H-NMR (DMSO-d$_6$, 300 MHz) 9.52 (s, 1H), 8.11 (s, 1H), 8.07 (d, J=6.9 Hz, 1H), 7.92 (d, J=8.4 Hz, 2H), 7.60 (s, 1H), 7.28 (d, J=8.4 Hz, 2H), 7.17 (s, 1H), 6.33 (s, 2H), 4.28 (t, J=7.2 Hz, 1H), 3.47 (s, 4H), 3.31 (s, 2H), 2.89 (s, 2H), 2.56 (d, J=8.1 Hz, 2H), 2.60-2.17 (m, 2H), 1.73 (s, 4H), 1.56 (d, J=11.4 Hz, 1H),1.44 (d, J=8.4 Hz, 1H), 1.00-1.30 (m, 6H) ppm; MS (ES) 606.15 (M + H), 604.31 (M − H). |

TABLE 2-continued

| No. | Structure | Name | Spectroscopic Data |
|---|---|---|---|
| 214 | 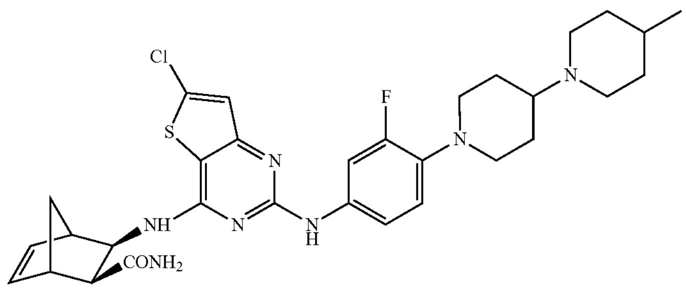 | (2S,3R)-3-(6-chloro-2-(3-fluoro-4-(4-methyl-1,4'-bipiperidin-1'-yl)phenylamino)thieno[3,2-d]pyrimidin-4-ylamino)bicyclo[2.2.1]hept-5-ene-2-carboxamide | $^1$H-NMR (DMSO-d$_6$, 300 MHz) 9.27 (s, 1H), 8.05 (s, 1H), 7.96 (d, J=15.9 Hz, 1H), 7.62 (s, 1H), 7.38 (d, J=8.7 Hz, 1H), 7.20 (s, 1H), 6.94 (t, J=9.0 Hz, 1H), 6.33 (s, 2H), 4.25 (t, J=7.2 Hz, 1H), 3.23 (d, J=11.4 Hz, 4H), 2.89 (s, 2H), 2.72-2.58 (m, 4H), 2.54 (d, J=8.1 Hz, 1H), 2.16 (d, J=9.0 Hz, 1H), 1.97 (d, J=9.9 Hz, 2H), 1.77-1.70 (m, 4H), 1.52 (m, 1H), 1.43 (d, J=8.7 Hz, 1H), 1.33-1.23 (m, 2H), 0.91 (d, J=6.3 Hz, 3H) ppm; MS (ES) 610.18 (M + H), 608.28 (M – H). |
| 215 | 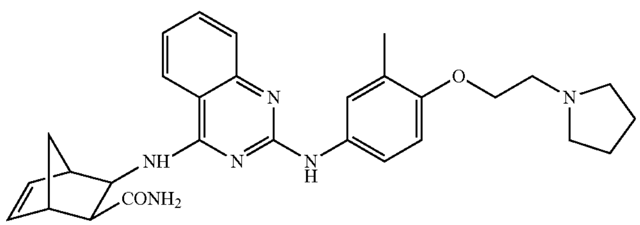 | Racemic-(2-exo,3-exo)-N4-(3-aminocarbonylbicyclo[2.2.1]hept-5-en-2-yl)-N2-(3-methyl-4-(2-(1-pyrrolidinyl)ethoxy)phenyl)-2,4-quinazoline-diamine | $^1$H-NMR (DMSO-d$_6$, 300 MHz) 8.78 (s, 1H), 8.42-8.34 (m, 1H), 7.62-7.51 (m, 3H), 7.32 (d, J=8.7 Hz, 1H), 7.17 (s, 1H), 7.12 (t, J=7.4 Hz, 1H), 6.82 (d, J=8.4 Hz, 1H), 6.32-6.29 (m, 2H), 4.35-4.25 (m, 1H), 4.03 (t, J=6.0 Hz, 2H), 2.88 (s, 2H), 2.68-2.58 (m, 4H), 2.57-2.55 (m, 2H), 2.22 (d, J=8.7 Hz, 1H), 2.14 (s, 3H), 1.74-1.64 (m, 4H), 1.43 (d, J=8.1 Hz, 1H) ppm; MS (ES) 499.47 (M + H), 497.30 (M – H). |
| 216 | 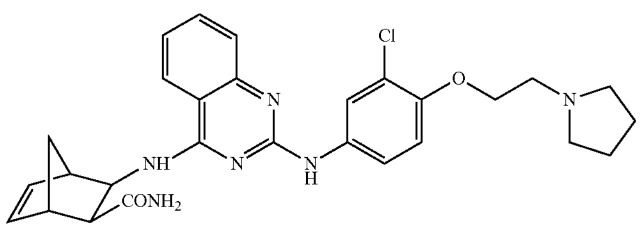 | Racemic-(2-exo,3-exo)-N4-(3-aminocarbonylbicyclo[2.2.1]hept-5-en-2-yl)-N2-(3-Chloro-4-(2-(1-pyrrolidinyl)ethoxy)phenyl)-2,4-quinazoline-diamine | $^1$H-NMR (DMSO-d$_6$, 300 MHz) 9.06 (s, 1H), 8.52-8.42 (m, 1H), 8.07 (s, 1H), 7.67-7.61 (m, 2H), 7.55 (t, J=7.8 Hz, 1H), 7.33 (d, J=8.4 Hz, 1H), 7.19 (s, 1H), 7.15 (t, J=7.2 Hz, 1H), 7.04 (d, J=9.0 Hz, 1H), 6.33 (s, 2H), 4.30-4.22 (m, 1H), 4.10 (t, J=5.7 Hz, 2H), 2.89-2.85 (m, 3H), 2.70-2.60 (m, 4H), 2.55 (d, J=8.4 Hz, 1H), 2.42-2.38 (m, 1H), 2.20 (d, J=7.5 Hz, 1H), 1.74-1.64 (m, 4H), 1.42 (d, J=9.0 Hz, 1H) ppm; MS (ES) 519.18 (M + H), 517.25 (M – H). |

TABLE 2-continued

| No. | Structure | Name | Spectroscopic Data |
|---|---|---|---|
| 217 | 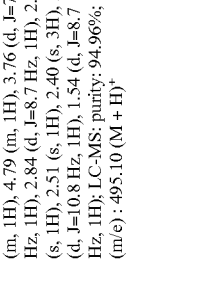 | Racemic-(5-exo,6-exo)-N4-(4,7-methano-1,2-benzisoxazol-3a,4,5,6,7,7a-hexahydro-3-phenyl-5-aminocarbonyl-6-yl)-N2-(3-methyl)phenyl[2,3-d]pyrimidine-2,4-diamine | $^1$H NMR (CD$_3$OD): δ 8.23 (s, 1H), 7.72 (m, 1H), 7.58-7.55 (m, 1H), 7.47-7.43 (m, 3H), 7.37-7.20 (m, 4H), 7.00-6.98 (m, 1H), 4.79 (m, 1H), 3.76 (d, J=7.8 Hz, 1H), 2.84 (d, J=8.7 Hz, 1H), 2.78 (s, 1H), 2.51 (s, 1H), 2.40 (s, 3H), 2.13 (d, J=10.8 Hz, 1H), 1.54 (d, J=8.7 Hz, 1H); LC-MS: purity: 94.96%; MS (m/e) : 495.10 (M + H)$^+$ |
| 218 | 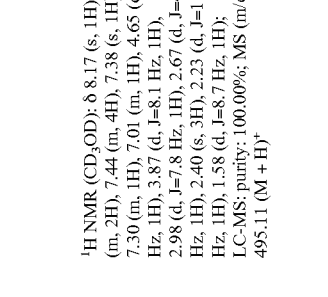 | Racemic-(5-exo,6-exo)-N4-(4,7-methano-1,2-benzisoxazol-3a,4,5,6,7,7a-hexahydro-3-phenyl-6-aminocarbonyl-5-yl)-N2-(3-methyl)phenyl[2,3-d]pyrimidine-2,4-diamine | $^1$H NMR (CD$_3$OD): δ 8.17 (s, 1H), 7.75 (m, 2H), 7.44 (m, 4H), 7.38 (s, 1H), 7.30 (m, 1H), 7.01 (m, 1H), 4.65 (d, J=7.5 Hz, 1H), 3.87 (d, J=8.1 Hz, 1H), 2.98 (d, J=7.8 Hz, 1H), 2.67 (d, J=4.8 Hz, 1H), 2.40 (s, 3H), 2.23 (d, J=11.4 Hz, 1H), 1.58 (d, J=8.7 Hz, 1H); LC-MS: purity: 100.00%; MS (m/e): 495.11 (M + H)$^+$ |
| 219 | 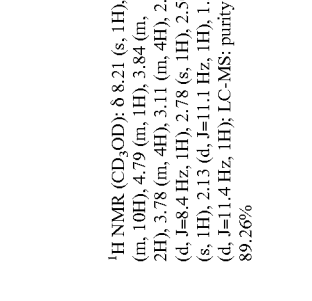 | Racemic-(5-exo,6-exo)-N4-(4,7-methano-1,2-benzisoxazol-3a,4,5,6,7,7a-hexahydro-3-phenyl-5-aminocarbonyl-6-yl)-N2-[4-(4-morpholinyl)phenyl]-1H-pyrrolo[2,3-d]pyrimidine-2,4-diamine | $^1$H NMR (CD$_3$OD): δ 8.21 (s, 1H), 7.64-7.07 (m, 10H), 4.79 (m, 1H), 3.84 (m, 2H), 3.78 (m, 4H), 3.11 (m, 4H), 2.84 (d, J=8.4 Hz, 1H), 2.78 (s, 1H), 2.50 (s, 1H), 2.13 (d, J=11.1 Hz, 1H), 1.53 (d, J=11.4 Hz, 1H); LC-MS: purity: 89.26% |

| No. | Structure | Name | Spectroscopic Data |
|---|---|---|---|
| 220 | 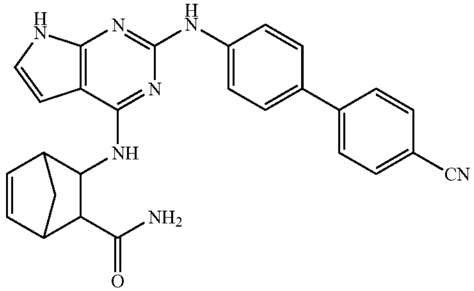 | Racemic-(2-exo,3-exo)-N4-(3-aminocarbonylbicyclo[2.2.1]hept-5-en-2-yl)-N2-[(4'-cyano[1,1'-biphenyl]-4-yl)]-1H-pyrrolo[2,3-d]pyrimidine-2,4-diamine | $^1$H NMR (CD$_3$OD): δ 8.20-8.18 (m, 1H), 7.82-7.61 (m, 6H), 8.35 (t, J=8.1 Hz, 1H), 8.16 (t, J=8.1 Hz, 1H), 6.98-6.92 (m, 2H), 6.80 (d, J=3.6 Hz, 1H), 6.35 (d, J=3.6 Hz, 1H), 6.21 (m, 1H), 6.06 (m, 1H), 4.47 (d, J=7.5 Hz, 1H), 2.93 (s, 1H), 2.83 (s, 1H), 2.60 (d, J=8.1 Hz, 1H), 2.29 (d, J=8.7 Hz, 1H), 1.55 (d, J=9.0 Hz, 1H); LC-MS: purity: 100.00%; MS (m/e): 462.04 (M + H)$^+$ |
| 221 | 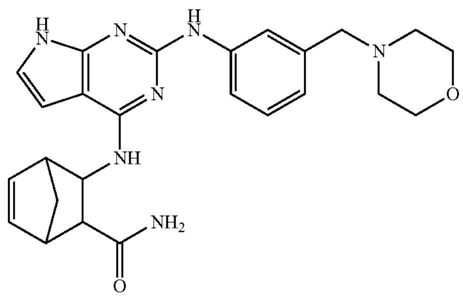 | Racemic-(2-exo,3-exo)-N4-(3-aminocarbonylbicyclo[2.2.1]hept-5-en-2-yl)-N2-(3-morpholin-4-yl-methylphenyl)-1H-pyrrolo[2,3-d]pyrimidine-2,4-diamine | $^1$H NMR (CD$_3$OD): δ 8.23 (s, 1H), 7.78 (m, 1H), 7.31-6.80 (m, 3H), 6.38 (m, 2H), 4.51 (d, J=9.3 Hz, 1H), 3.85-3.63 (m, 4H), 2.97 (s, 1H), 2.93 (s, 1H), 2.88-2.76 (m, 6H), 2.64 (d, J=8.7 Hz, 1H), 2.42 (d, J=9.3 Hz, 1H), 1.59 (d, J=9.6 Hz, 1H); LC-MS: purity: 100.00%; MS (m/e): 460.09 (M + H)$^+$ |
| 222 | 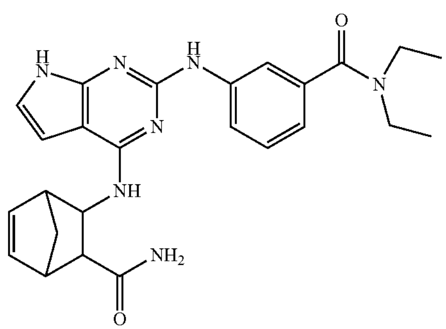 | Racemic-(2-exo,3-exo)-N4-(3-aminocarbonylbicyclo[2.2.1]hept-5-en-2-yl)-N2-(3-N,N-diethyl-aminocarbonyl-phenyl)-1H-pyrrolo[2,3-d]pyrimidine-2,4-diamine | $^1$H NMR (CD$_3$OD): δ 8.13 (s, 1H), 8.01 (s, 1H), 7.64 (dd, J=2.1, 7.8 Hz, 1H),7.31 (t, J=7.5 Hz, 1H), 6.87 (d, J=7.5 Hz, 1H), 6.80 (d, J=3.6 Hz, 1H), 3.35 (d, J=3.6 Hz, 1H), 6.32 (m, 2H), 4.48 (d, J=7.5 Hz, 1H), 3.56 (m, 4H), 2.96 (s, 1H), 2.88 (s, 1H), 2.66 (d, J=6.3 Hz, 1H), 2.32 (d, J=8.7 Hz, 1H), 1.58 (d, J=9.6 Hz, 1H), 1.27 (t, J=6.6 Hz, 3H), 1.16 (t, J=6.6 Hz, 3H); LC-MS: purity: 100.00%; MS (m/e): 460.09 (M + H)$^+$ |

TABLE 2-continued

| No. | Structure | Name | Spectroscopic Data |
|---|---|---|---|
| 223 | 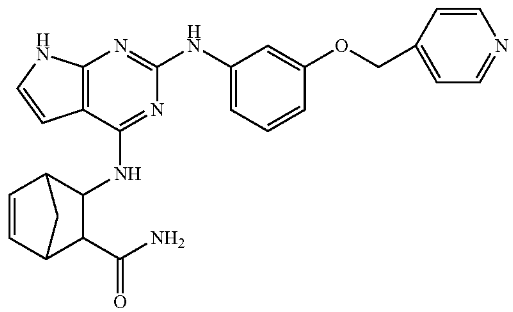 | Racemic-(2-exo,3-exo-)N4-(3-aminocarbonylbicyclo[2.2.1]hept-5-en-2-yl)-N2-[3-(4-pyridinylmethoxy)phenyl-1H-pyrrolo[2,3-d]pyrimidine-2,4-diamine | $^1$H NMR (CD$_3$OD): δ 8.52 (m, 2H), 8.10 (m, 2H), 7.68–6.63 (m, 4H), 6.39 (d, J=3.3 Hz, 1H), 6.35–6.26 (m, 2H), 5.18 (s, 2H), 4.46 (d, J=8.1 Hz, 1H), 2.94 (s, 1H), 2.91 (s, 1H), 2.65 (d, J=8.1 Hz, 1H), 2.30 (d, J=9.0 Hz, 1H), 1.58 (d, J=9.0 Hz, 1H); LC-MS: purity: 100.00%; MS (m/e): 468.11 (M + H)$^+$ |
| 224 | 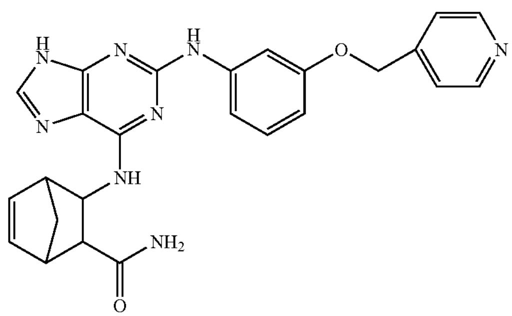 | Racemic-(2-exo,3-exo-)N6-(3-aminocarbonylbicyclo[2.2.1]hept-5-en-2-yl)-N2-[3-(4-pyridinylmethoxy)phenyl-1H-purine-2,6-diamine | $^1$H NMR (CD$_3$OD): δ 8.52 (dd, J=1.8, 4.5 Hz, 2H), 8.23 (s, 1H), 7.76 (s, 1H), 7.73 (m, 1H), 7.53 (d, J=6.0 Hz, 2H), 6.59 (m, 1H), 6.34–6.26 (m, 2H), 5.18 (s, 2H), 4.48 (d, J=7.8 Hz, 1H), 2.96 (s, 1H), 2.86 (s, 1H), 2.67 (d, J=8.7 Hz, 1H), 2.35 (d, J=8.7 Hz, 1H), 1.62 (d, J=9.0 Hz, 1H); LC-MS: purity: 100.00%; MS (m/e): 469.35 (M + H)$^+$ |
| 225 | 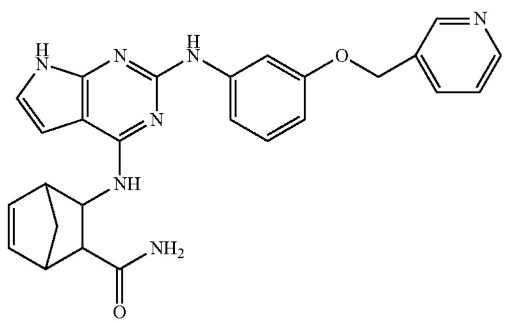 | Racemic-(2-exo,3-exo-)N4-(3-aminocarbonylbicyclo[2.2.1]hept-5-en-2-yl)-N2-[3-(3-pyridinylmethoxy)phenyl-1H-pyrrolo[2,3-d]pyrimidine-2,4-diamine | $^1$H NMR (CD$_3$D): δ 8.65 (d, J=1.5 Hz, 1H), 8.50 (dd, J=1.5, 4.8 Hz, 1H), 8.11 (bs, 2H), 7.96–7.34 (m, 1H), 7.72 (t, J=2.1 Hz, 1H), 7.49–7.44 (m, 1H), 7.19 (t, J=8.1 Hz, 1H), 7.07–7.04 (m, 1H), 6.82 (d, J=3.6 Hz, 1H), 6.68–6.64 (m, 1H), 6.38 (d, J=3.6 Hz, 1H), 6.29 (m, 1H), 6.20 (m, 1H), 5.15 (s, 2H), 4.44 (d, J=7.8 Hz, 1H), 2.94 (s, 1H), 2.90 (s, 1H), 2.65 (d, J=8.1 Hz, 1H), 2.29 (d, J=9.3 Hz, 1H), 1.56 (d, J=9.0 Hz, 1H); LC-MS: purity: 100.00%; MS (m/e): 468.09 (M + H)$^+$ |

TABLE 2-continued

| No. | Structure | Name | Spectroscopic Data |
|---|---|---|---|
| 226 | 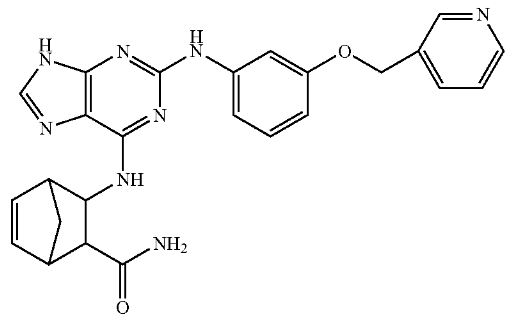 | Racemic-(2-exo,3-exo-)-N6-(3-aminocarbonylbicyclo[2.2.1]hept-5-en-2-yl)-N2-[3-(3-pyridinylmethoxy)phenyl]-1H-purine-2,6-diamine | $^1$H NMR (CD$_3$OD): δ 8.65 (m, 1H), 8.49 (dd, J=1.8, 5.1 Hz, 1H), 8.11 (bs, 2H), 7.97-7.94 (m, 1H), 7.79 (t, J=1.8 Hz, 1H), 7.76 (s, 1H), 7.49-7.44 (m, 1H), 7.16 (t, J=8.1 Hz, 1H), 7.09-7.05 (m, 1H), 6.62-6.58 (m, 1H), 6.28 (m, 1H), 6.21 (m, 1H), 5.15 (s, 2H), 4.62 (d, J=7.8 Hz, 1H), 2.95 (s, 1H), 2.85 (s, 1H), 2.67 (d, J=7.2 Hz, 1H), 2.34 (d, J=9.3 Hz, 1H), 1.61 (d, J=9.0 Hz, 1H); LC-MS: purity: 100.00%; MS (m/e): |
| 227 | 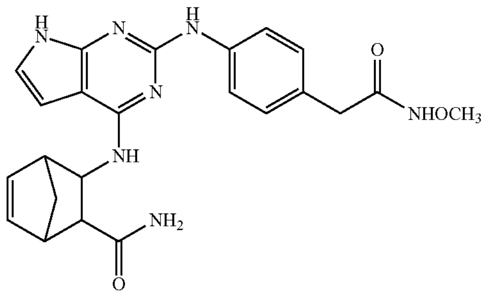 | Racemic-(2-exo,3-exo-)-N4-(3-aminocarbonylbicyclo[2.2.1]hept-5-en-2-yl)-N2-[4-(N-methoxy)aminocarbonyl-methylphenyl]-1H-pyrrolo[2,3-d]pyrimidine-2,4-diamine | 469.06 (M + H)$^+$ $^1$H NMR (CD$_3$OD): δ 8.15 (m, 1H), 7.63 (d, J=8.7 Hz, 1H), 7.20 (d, J=8.4 Hz, 2H), 6.34 (m, 4H), 4.45 (d, J=7.5 Hz, 1H), 3.68 (s, 3H), 3.35 (s, 2H), 2.97 (s, 1H), 2.91 (s, 1H), 2.65 (d, J=8.1 Hz, 1H), 2.30 (d, J=8.4 Hz, 1H), 1.59 (d, J=9.6 Hz, 1H); LC-MS: purity: 100.00%; MS (m/e): 448.06 (M + H)$^+$ |
| 228 | 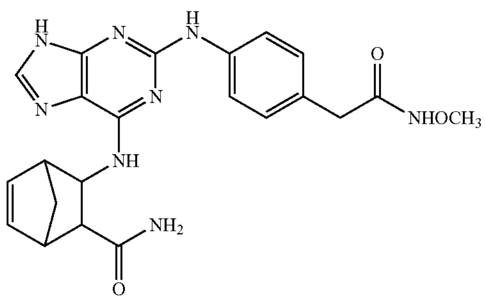 | Racemic-(2-exo,3-exo-)-N6-(3-aminocarbonylbicyclo[2.2.1]hept-5-en-2-yl)-N2-[4-(N-methoxy)aminocarbonyl-inethylphenyl]-1H-purine-2,6-diamine | $^1$H NMR (CD$_3$OD): δ 8.23 (m, 1H), 8.14 (s, 1H), 7.76 (d, J=1.8 Hz, 1H), 7.64 (m, 2H), 7.50 (m, 2H), 7.24-7.13 (m, 4H), 6.33 (m, 2H), 4.45 (m, 1H), 3.68 (s, 3H), 3.57 (s, 2H), 2.98 (s, 1H), 2.87 (s, 1H), 2.66 (d, J=7.2 Hz, 1H), 2.36 (d, J=9.3 Hz, 1H), 1.62 (d, J=9.0 Hz, 1H); LC-MS: purity: 100.00%; MS (m/e): 449.05 (M + H)$^+$ |

TABLE 2-continued

| No. | Structure | Name | Spectroscopic Data |
|---|---|---|---|
| 229 | 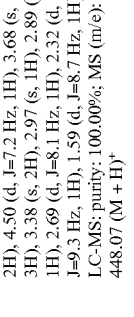 | Racemic-(2-exo,3-exo)-N4-(3-aminocarbonylbicyclo[2.2.1]hept-5-en-2-yl)-N2-[3-(N-methoxy)aminocarbonyl-methylphenyl]-1H-pyrrolo[2,3-d]pyrimidine-2,4-diamine | ¹H NMR (CD₃OD): δ 8.16 (m, 1H), 7.62 (m, 2H), 7.22 (m, 1H), 6.87 (m, 1H), 6.80 (m, 1H), 6.38 (m, 1H), 6.33 (m, 2H), 4.50 (d, J=7.2 Hz, 1H), 3.68 (s, 3H), 3.38 (s, 2H), 2.97 (s, 1H), 2.89 (s, 1H), 2.69 (d, J=8.1 Hz, 1H), 2.32 (d, J=9.3 Hz, 1H), 1.59 (d, J=8.7 Hz, 1H); LC-MS: purity: 100.00%; MS (m/e): 448.07 (M + H)⁺ |
| 230 | 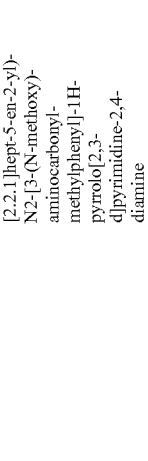 | Racemic-(2-exo,3-exo-)-N6-(3-aminocarbonylbicyclo[2.2.1]hept-5-en-2-yl)-N2-[3-(N-methoxy)aminocarbonyl-methylphenyl]-1H-purine-2,6-diamine | ¹H NMR (CD₃OD): δ 8.32 (s, 1H), 7.76 (d, J=2.4 Hz, 1H) 7.69 (s, 1H) <7.60-7.42 (m, 2H), 7.19 (m, 2H), 7.02 (m, 1H), 6.84 (m, 1H), 6.61 (m, 2H), 6.33 (m, 2H), 4.61 (m, 1H), 3.69 (s, 3H), 3.37 (s, 2H), 2.98 (s, 1H), 2.85 (s, 1H), 2.71 (d, J=7.8 Hz, 1H), 2.38 (d, J=8.7 Hz, 1H), 1.63 (d, J=9.0 Hz, 1H); LC-MS: purity: 100.00%; MS (m/e): 449.65 (M + H)⁺ |
| 231 | 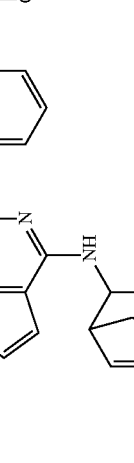 | Racemic-(2-exo,3-exo)-N4-(3-hydrazidebicyclo[2.2.1]hept-2-yl)-N2-(3-methoxyphenyl)-1H-pyrrolo[2,3-d]pyrimidine-2,4-diamine | ¹H NMR (CD₃OD): δ 8.18 (m, 2H), 7.96 (m, 1H), 7.43 (m, 1H), 7.16 (m, 2H), 6.80 (m, 1H), 6.54 (m, 1H), 6.39 (m, 2H), 4.49 (m, 1H), 3.81 (s, 3H), 2.77-2.20 (m, 5H), 1.65-1.31 (m, 6H); LC-MS: purity: 100.00%; MS (m/e): 408.08 (M + H)⁺ |

| No. | Structure | Name | Spectroscopic Data |
|---|---|---|---|
| 232 | 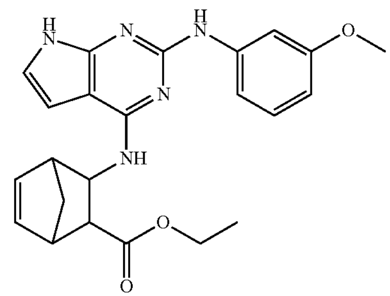 | Racemic-(2-exo,3-exo)-N4-(3-ethoxycarbonylbicyclo[2.2.1]hept-5-en-2-yl)-N2-(3-methoxyphenyl)-1H-pyrrolo[2,3-d]pyrimidine-2,4-diamine | $^1$H NMR (CD$_3$OD): δ 7.24 (m, 2H), 7.08 (m, 1H), 6.92 (s, 1H), 6.78 (m, 2H), 6.36 (m, 2H), 4.12 (q, J=4.2 Hz, 2H), 3.81 (s, 3H), 3.05 (s, 1H), 2.95 (s, 1H), 2.69 (d, J=8.1 Hz, 1H), 2.40 (d, J=9.0 Hz, 1H), 1.59 (d, J=8.7 Hz, 1H), 0.89 (t, J=4.2 Hz, 3H); LC-MS: purity: 95.69%; MS (m/e): 420.66 (M + H)$^+$ |
| 233 | 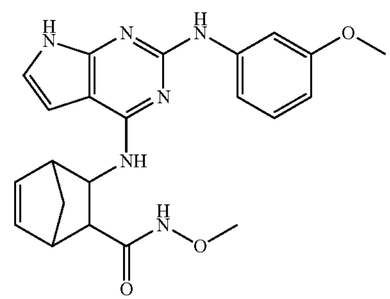 | Racemic-(2-exo,3-exo)-N4-(N-methoxy-3-aminocarbonylbicyclo[2.2.1]hept-5-en-2-yl)-N2-(3-methoxyphenyl)-1H-pyrrolo[2,3-d]pyrimidine-2,4-diamine | $^1$H NMR (CD$_3$OD): δ 8.24 (s, 1H), 7.92 (s, 1H), 7.11 (m, 2H), 6.79 (m, 1H), 6.50 (m, 1H), 6.38 (m, 2H), 6.27 (m, 1H), 4.53 (d, J=7.5 Hz, 1H), 3.78 (s, 3H), 2.93 (s, 1H), 2.90 (s, 1H), 2.46 (d, J=8.4 Hz, 1H), 2.41 (d, J=8.4 Hz, 1H), 1.63 (d, J=8.7 Hz, 1H); LC-MS: purity: 100.00%; MS (m/e): 421.01 (M + H)$^+$ |
| 234 | 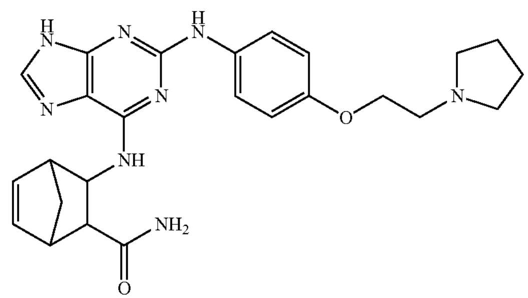 | Racemic-(2-exo,3-exo-)-N6-(3-aminocarbonylbicyclo[2.2.1]hept-5-en-2-yl)-[2-(4-pyrrolidinyl)ethoxy]phenyl]-1H-purine-2,6-diamine | LC-MS: purity: 100.00%; MS (m/e): 475.18 (M + H)$^+$ |

| No. | Structure | Name | Spectroscopic Data |
|---|---|---|---|
| 235 | 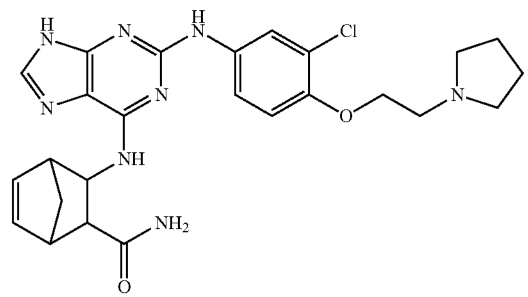 | Racemic-(2-exo,3-exo-)-N6-(3-aminocarbonylbicyclo[2.2.1]hept-5-en-2-yl)-N2-[3-chloro-4-[2-(1-pyrrolidinyl)ethoxy]phenyl]-1H-purine-2,6-diamine | LC-MS: purity: 93.00%; MS (m/e): 509.17 (M + H)+ |
| 236 | 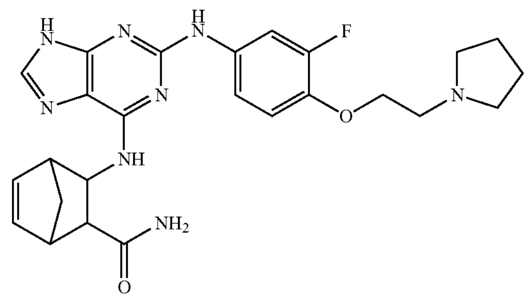 | Racemic-(2-exo,3-exo-)-N6-(3-aminocarbonylbicyclo[2.2.1]hept-5-en-2-yl)-N2-[3-fluoro-4-[2-(1-pyrrolidinyl)ethoxy]phenyl]-1H-purine-2,6-diamine | LC-MS: purity: 74.34%; MS (m/e): 493.18 (M + H)+ |
| 237 | 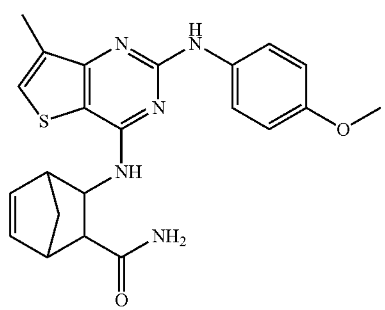 | Racemic-(2-exo,3-exo-)-7-methyl-N4-(3-aminocarbonylbicyclo[2.2.1]hept-5-en-2-yl)-N2-[4-methoxyphenyl]-thieno[3,2-d]pyrimidine-2,4-diamine | 1H NMR (CD3OD): δ 7.65 (s, 1H), 7.50 (m, 2H), 6.94 (m, 2H), 6.36 (m, 1H), 6.23 (m, 1H), 4.25 (d, J=7.2 Hz, 1H), 3.81 (s, 3H), 2.98 (s, 1H), 2.94 (s, 1H), 2.59 (d, J=7.8 Hz, 1H), 2.37 (s, 3H), 2.18 (d, J=9.6 Hz, 1H), 1.57 (d, J=9.0 Hz, 1H); LC-MS: purity: 100.00%; MS (m/e): 422.13 (M + H)+ |

| No. | Structure | Name | Spectroscopic Data |
|---|---|---|---|
| 238 | 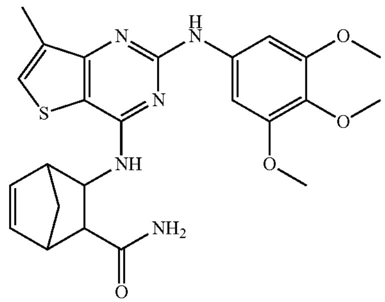 | Racemic-(2-exo,3-exo-)-7-methyl-N4-(3-aminocarbonylbicyclo[2.2.1]hept-5-en-2-yl)-N2-[(3,4,5-trimethoxyphenyl]-thieno[3,2-d]pyrimidine-2,4-diamine | $^1$H NMR (CD$_3$OD): δ 8.09 (s, 1H), 7.52 (s, 1H), 7.14 (s, 1H), 6.32 (m, 1H), 6.27 (m, 1H), 4.47 (d, J=7.2 Hz, 1H), 3.855 (s, 3H), 3.851 (s, 3H), 3.75 (s, 1H), 2.97 (s, 1H), 2.90 (s, 1H), 2.65 (d, J=6.9 Hz, 1H), 2.36 (s, 3H), 2.30 (d, J=9.6 Hz, 1H), 1.58 (d, J=9.6 Hz, 1H); LC-MS: purity: 100.00%; MS (m/e): 482.13 (M + H)$^+$ |
| 239 | 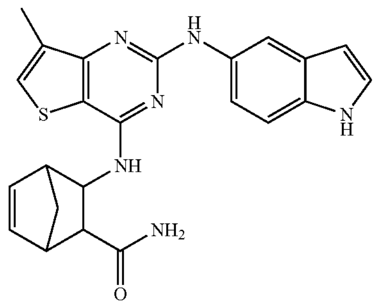 | Racemic-(2-exo,3-exo-)-7-methyl-N4-(3-aminocarbonylbicyclo[2.2.1]hept-5-en-2-yl)-N2-[1H-indol-5-yl]-thieno[3,2-d]pyrimidine-2,4-diamine | $^1$H NMR (CD$_3$OD): δ 8.21 (s, 1H), 7.87, 7.25 (m, 2H), 6.42 (m, 1H), 6.29 (m, 1H), 6.18 (m, 1H), 4.30 (d, J=8.7 Hz, 1H), 2.95 (m, 2H), 2.56 (d, J=9.0 Hz, 1H), 2.36 (s, 3H), 2.19 (d, J=9.6 Hz, 1H), 1.55 (d, J=9.3 Hz, 1H); LC-MS: purity: 100.00%; MS (m/e) : 431.10 (M + H)$^+$ |
| 240 | 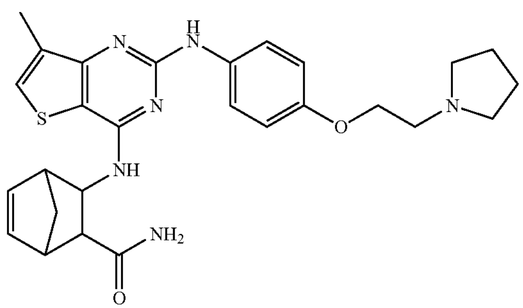 | Racemic-(2-exo,3-exo-)-7-methyl-N4-(3-aminocarbonylbicyclo[2.2.1]hept-5-en-2-yl)-N2-[2-(1-pyrrolidinyl)ethoxy]phenyl]-thieno[3,2-d]pyrimidine-2,4-diamine | $^1$H NMR (CD$_3$OD): δ 7.72 (s, 1H), 7.61 (d, J=8.7 Hz, 2H), 7.08 (d, J=8.7 Hz, 2H), 6.36 (m, 1H), 6.24 (m, 1H), 4.36 (m, 2H), 4.24 (d, J=7.5 Hz, 1H), 3.68 (m, 4H), 3.25 (m, 2H), 3.01 (s, 1H), 2.98 (s, 1H), 2.59 (d, J=7.8 Hz, 1H), 2.39 (s, 3H), 2.20 (d, J=9.3 Hz, 1H), 2.09 (m, 4H), 1.57 (d, J=9.0 Hz, 1H); LC-MS: purity: 100.00%; MS (m/e): 505.20 (M + H)$^+$ |

TABLE 2-continued

| No. | Structure | Name | Spectroscopic Data |
|---|---|---|---|
| 241 | 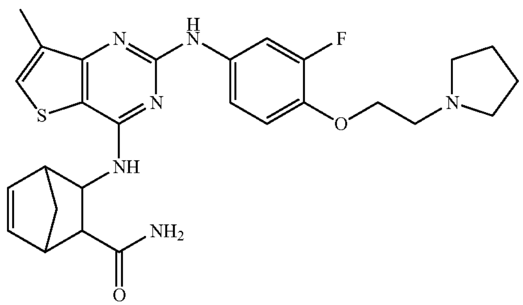 | Racemic-(2-exo,3-exo-)-7-methyl-N4-(3-aminocarbonylbicyclo[2.2.1]hept-5-en-2-yl)-N2-[3-fluoro-4-[2-(1-pyrrolidinyl)ethoxy]phenyl]-thieno[3,2-d]pyrimidine-2,4-diamine | $^1$H NMR (CD$_3$OD): δ 8.05 (s, 1H), 7.92 (d, J=12.3 Hz, 2H), 7.29-7.16 (m, 2H), 6.36 (m, 1H), 6.34 (m, 1H), 4.38 (m, 2H), 4.32 (d, J=7.8 Hz, 1H), 3.69 (m, 4H), 3.28 (m, 2H), 3.01 (s, 2H), 2.63 (d, J=7.5 Hz, 1H), 2.38 (s, 3H), 2.21 (d, J=9.6 Hz, 1H), 2.15 (m, 4H), 1.59 (d, J=8.7 Hz, 1H); LC-MS: purity: 100.00%; MS (m/e): 523.22 (M + H)$^+$ |
| 242 | 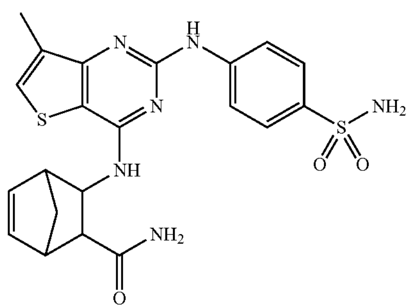 | Racemic-(2-exo,3-exo-)-7-methyl-N4-(3-aminocarbonylbicyclo[2.2.1]hept-5-en-2-yl)-N2-(4-aminosulfonyl)phenyl-thieno[3,2-d]pyrimidine-2,4-diamine | $^1$H NMR (CD$_3$OD): δ 8.13 (s, 1H), 7.98 (m, 2H), 7.78 (m, 2H), 7.43 (m, 1H), 6.36 (m, 2H), 4.46 (d, J=6.6 Hz, 1H), 2.98 (s, 1H), 2.95 (s, 1H), 2.68 (d, J=8.4 Hz, 1H), 2.35 (s, 3H), 2.27 (d, J=8.7 Hz, 1H), 1.58 (d, J=9.3 Hz, 1H); LC-MS: purity: 100.00%; MS (m/e): 471.08 (M + H)$^+$ |

Example 9

The Compounds Inhibit Protein Kinases

JAK inhibition was tested in human Ramos B-cells activated with IL-4. Twenty to 24 hours post stimulation, the cells are stained for upregulation of CD23 and analyzed by FACS. Stimulation of the B-cells with IL-4 leads to the activation of the JAK/STAT pathway through phosphorylation of the JAK kinase JAK1 and JAK3, which in turn phosphorylate and activate transcription of factor STAT-5. The low-affinity IgE receptor (CD23) is upregulated by activated STAT-5.

For the assay, human Ramos B-cells (ATCC, Catalog No. CRL-1596) are cultured in RPMI 1640 medium (Cellgro, Catalog No. 10-040-CM) containing 10% fetal bovine serum (JRH, Catalog No. 12106-500M) according to the propagation protocol supplied with the cells, and maintained at a density of approximately $3.5 \times 10^5$ cells/ml. The day before the assay, the cells are diluted to $3.5 \times 10^5$ cells/ml to insure they are in the logarithmic growth phase. The cells are spun down, and suspended in RPMI 1640 medium containing 5% fetal bovine serum to a density of $3.5 \times 10^4$ cells/ml and aliquots dispensed into a 96-well tissue culture plate. Cells are incubated with test compound (dissolved in DMSO) or DMSO (control) for 1 hr at 37° C. and then stimulated with IL-4 (Pepotech, Catalog No. 200-04) for 20-24 hours (final concentration is 50 Units/ml). Cells are then spun down, stained with anti-CD23-PE antibody (BD Pharmigen, Catalog No. 555711) and analyzed by FACS.

All of the compounds in Table 1 were tested for their ability to inhibit JAK kinases in this cellular assay. All of the compounds tested exhibited $IC_{50}$s of less than 1 μM, with the exception of compounds 101, 102, 110, 122, 125, 135, 140-146, 150, 152, 153, and 168. Compounds 125, 135, 142, 150, 152 and 168 exhibited $IC_{50}$s of greater than 10 μM. Compound 110 exhibited an $IC_{50}$ of less than 10 MM. Compounds 101, 102, 122, 140, 141, 143-147, and 153 exhibited $IC_{50}$s of less than 5 μM.

Compounds 217-231 and 233-242 in Table 2 were tested for their ability to inhibit JAK kinases in this cellular assay. All of the compounds tested exhibited $IC_{50}$s of less than 1 μM, with the exception of compounds 217, 218, 219, 223-226, 231, 233, and 237-242. Compounds 223-226 exhibited $IC_{50}$s of greater than 10 μM. Compounds 217 and 219 exhibited an $IC_{50}$ of less than 10 μM. Compounds 218, 231, 233, and 237-242 exhibited $IC_{50}$s of less than 5 μM.

The compounds of the invention were tested in the following assay for their ability to inhibit Axl activity.

Phospho-Akt in-Cell Western Assay

Reagents and Buffers:

Cell culture plate: 96 well assay plate (Coming 3610), white, clear bottom, tissue-culture treated.

Cells: Hela cells.

Starvation medium: For Axl stimulation: 0.5% FCS (fetal calf serum) in DMEM, plus Axl/Fc (extracellular domain of AXL fused to immunoglobulin Fc region) (R&D, 154-AL) 500 ng/mL.

For EGF (epidermal growth factor) stimulation: 0.5% FCS in DMEM (Dulbecco's modified Eagles medium).

Poly-L-Lysine 0.01% solution (the working solution): 10 μg/ml, dilute In PBS (phosphate buffered saline).

Axl antibody cross-linking:

$1^{st}$: Mouse anti-Axl (R&D, MAB 154).

$2^{nd}$: Biotin-SP-conjugated AffiniPure goat anti-mouse IgG (H+L) (Jackson ImmunoResearch #115-065-003).

Fixing buffer: 4% formaldehyde in PBS.

Wash buffer: 0.1% TritonX-100 in PBS.

Quenching buffer: 3% $H_2O_2$, 0.1% Azide in wash buffer, Azide and hydrogen peroxide ($H_2O_2$) are added fresh.

Blocking buffer: 5% BSA in TBST (tris buffered saline plus 0.1% Tween 20).

Primary antibody: Rabbit anti-human Phospho-Akt antibody (Cell Signaling 9271): 1×250 diluted in blocking buffer.

Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.

Chemiluminescent working solution (Pierce, 37030): SuperSignal ELISA (enzyme linked immunosorbant assay) Pico Chemiluminescent substrate.

Crystal Violet solution: Stock: 2.5% Crystal violet in methanol, filtered and kept at ambient temperature. The working solution: dilute the stock 1:20 with PBS immediately before use.

10% SDS: working solution: 5% SDS (sodium dodecyl-sulfate), diluted in PBS

Methods:

Day 1:

A 96 well TC (tissue culture treated) plate was coated with 10 μg/mL poly-L-Lysine at 37° C. for 30 min, washed twice with PBS, and air-dried for 5 minutes before cells were added. Hela cells were seeded at 10,000 cells/well and the cells were starved in 100 μL starvation medium containing Axl/Fc for 24 hrs.

Day 2:

The cells were pre-treated with test compounds by adding 100 μL of 2× test compound to the starvation medium on the cells. The cells were incubated at 37° C. for 1 hr before stimulation.

The cells were stimulated by Axl-antibody cross-linking as follows: A 5× $1^{st}/2^{nd}$ Axl antibody mixture was made (37.5 μg/mL $1^{st}$/100 μg/mL $2^{nd}$) in starvation medium and nutated at 4° C. with thorough mixing for 1-2 hours for clustering. The resulting mix was warmed to 37° C. 50 μL of 5× Axl $1^{st}/2^{nd}$ of antibody cluster was added to the cells and the cells were incubated at 37° C. for 5 min.

After 5 minutes stimulation, the plate was flicked to remove medium and the plate was tapped onto paper towels. Formaldehyde (4.0% in PBS, 100 μL) was added to fix the cells and the cells were incubated at ambient temperature for 20 min without shaking.

The cells were washed with a plate washer buffer to remove the formaldehyde solution. The plate was flicked to remove excess wash buffer and tapped onto paper towels. Quenching buffer (100 μL) was added to each well and the cells were incubated at ambient temperature for 20 minutes without shaking.

The cells were washed with a plate washer buffer to remove the quenching buffer. Blocking buffer (100 μL) was added and the cells were incubated at ambient temperature for at least an hour with gentle shaking.

The cells were washed with a plate washer buffer and diluted primary antibody (50 μL) was added to each well (blocking buffer was added to the negative control wells instead). The plates were incubated overnight at 4° C. with gentle shaking.

Day 3:

The wash buffer was removed, diluted secondary antibody (100 μL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 μL: 40 μL A and 40 μL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 μL) was added to each well and the cells were incubated at ambient temperature for 30 min. The crystal violet solution was removed, and the wells were rinsed with PBS, then washed 3× with PBS (200 μL) for 5 minutes each.

5% SDS solution (70 μL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

All the compounds in Table 2 were tested for their ability to inhibit Axl kinase. All of the compounds tested exhibited $IC_{50}$s of less than 1 μM, with the exception of compounds 182, 185, 186, 188, 189, 197, 198, 208-211, 215-234, and 237-242. Compounds 189, 208, 210, 217-220, 227, 228, 230, 237-239, and 242 exhibited an $IC_{50}$ of greater than 10 μM. Compounds 211, 223, 224, 229, 231, 232, and 240 exhibited $IC_{50}$s of less than 10 μM. Compounds 182, 185, 186, 197, 198, 209, 215, 216, 221, 222, 225, 226, 233, 234, and 241 exhibited $IC_{50}$s of less than 5 μM.

All of the compounds in Table 1 were tested for their ability to inhibit Lck kinase, with the exception of compounds 138, 139, 147, 148, 149, and 168-173. With the exception of compounds 135, 136, 151, 152, 153, and 165, all of these compounds exhibited $IC_{50}$s of less than 1 μM. Compound 136 exhibited an $IC_{50}$ of less than 10 μM. Compounds 135, 151, 152, 153, and 165 exhibited $IC_{50}$s of less than 5 μM.

Compounds 104, 107, 109, 112, 113, 131, 134, 136, 148, and 154 were tested for their ability to inhibit kinase Lyn b. With the exception of compound 136, which exhibited an $IC_{50}$ of greater than 10 μM, all of the compounds tested exhibited $IC_{50}$s of less than 1 μM.

All of the compounds on Table 1 were tested in a cell-based Syk assay for their ability to inhibit Syk kinase, with the exception of compounds 138, 139, 147-149, and 168-173. Compound 140 exhibited an $IC_{50}$ of greater than 10 μM. Compounds 110, 136, 141-146, 151 and 153 exhibited $IC_{50}$s of less than 10 μM. All others exhibited $IC_{50}$s of less than 1 μM. Compounds 190-192, 217-231, and 235-239 in Table 2 were tested in a cell-based Syk assay for their ability to inhibit Syk kinase. All of the compounds tested exhibited $IC_{50}$s of less than 1 μM, with the exception of compounds 217-219, 221, 227, 228, 230, 231, and 235-239. Compounds 217, 219, 228, 237, and 238 exhibited an $IC_{50}$ of greater than 10 μM. Compounds 21 8, 227, and 236 exhibited $IC_{50}$s of less than 10 μM. Compounds 221, 230, 231, 235, and 239 exhibited $IC_{50}$s of less than 5 μM.

Compounds 218, 220, and 221 in Table 2 were tested for their ability to inhibit PRK1 kinase. All of the compounds tested exhibited $IC_{50}$s of less than 5 μM.

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated into the application by reference for all purposes.

What is claimed is:

1. A compound according to structural formula (I):

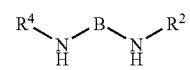

or a salt, or N-oxide thereof, wherein:

B is

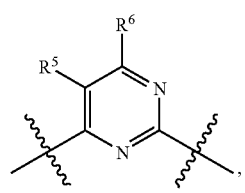

(B.1)

wherein $R^5$ and $R^6$ together with the carbon atoms of the pyrimidine ring to which they are attached form a diazole ring, optionally substituted with one or more $R^a$ and/or $R^b$;

$R^2$ is selected from the group consisting of a ($C_6$-$C_{20}$) aryl optionally substituted with one or more $R^8$, a 5-20 membered heteroaryl optionally substituted with one or more $R_8$, a ($C_7$-$C_{28}$) arylalkyl optionally substituted with one or more $R^8$ and a 6-28 membered heteroarylalkyl optionally substituted with one or more $R^8$;

$R^4$ is a saturated or unsaturated, bridged cycloalkyl containing a total of from 3 to 16 annular carbon atoms that is substituted with an $R^7$ group, wherein $R^4$ is further optionally substituted with one or more $R^f$;

$R^7$ selected from the group consisting of —(O)$OR^d$, —C(O)$NR^dR^d$, —C(O)$NR^dOR^d$, or —C(O)$NR^dN$-$R^dR^d$;

each $R^8$ group is, independently of the others, selected from the group consisting of $R^a$, $R^b$, $C_1$-$C_8$ alkyl optionally substituted with one or more $R^a$ and/or $R^b$, $C_3$-$C_8$ cycloalkyl optionally substituted with one or more $R^a$ and/or $R^b$, heterocycloalkyl containing 3 to 12 annular atoms, optionally substituted with one or more $R^a$ and/or $R^b$, $C_1$-$C_8$ alkoxy optionally substituted with one or more $R^a$ and/or $R^b$, and —O—$(CH_2)_x$—$R^b$, where x is 1-6, a water-solubilizing group of the formula

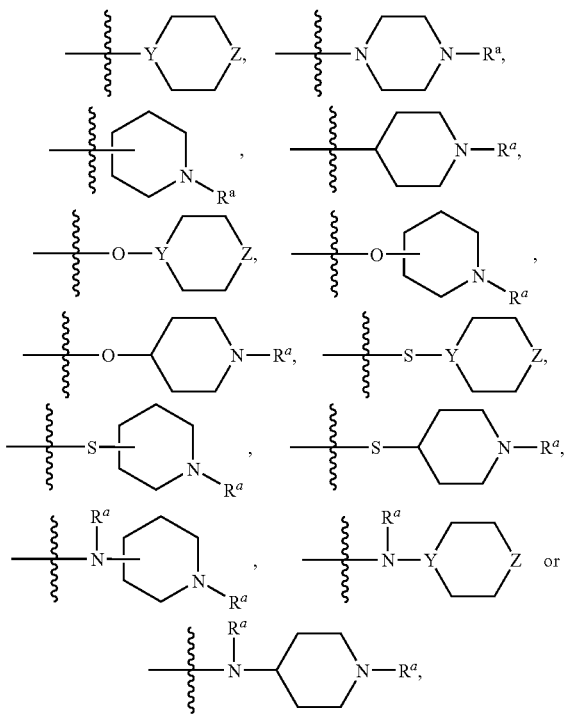

where Y is selected from the group consisting of CH and N, Z is selected from the group consisting of —C(H(R$^a$))—, —CH$_2$—, —O—, —S—, —NH—, —N(—(CH$_2$)$_y$—R$^a$)—, —N(—(CH$_2$)$_y$—C(O)R$^a$)—, —N(—(CH$_2$)$_y$—C(O)OR$^a$)—, —N(CH$_2$)$_y$—S(O)$_2$R$^a$)—, —N(—(CH$_2$)$_y$—S(O)$_2$OR$^a$)—, with the proviso that Y and Z are not both simultaneously CH and CH$_2$, respectively, or a water solubilizing group selected from the group consisting of morpholino, piperidinyl, (C$_1$-C$_6$) N-alkyl piperidinyl, N-methyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, 1-C$_6$) N-alkylpiperazinyl, N-methylpiperazinyl, N-ethyl piperidinyl, N-ethyl piperazinyl, N-cycloalkyl piperazinyl, N-cyclohexyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, and imidazolyl;

each R$^a$ is, independently of the others, selected from the group consisting of hydrogen, C$_1$-C$_8$ alkyl, bridged or unbridged C$_3$-C$_{10}$ cycloalkyl, bridged or unbridged heterocycloalkyl containing 3 to 12 annular atoms, heteroaryl, (C$_6$-C$_{14}$) aryl, and (C$_7$-C$_{20}$) arylalkyl, wherein R$^a$ is optionally substituted with one or more R$^f$;

each R$^b$ is, independently of the others, a group selected from the group consisting of =O, —OR$^a$, (C$_1$-C$_3$) haloalkyloxy, =S, SR$^a$, =NR$^a$, =NOR$^a$, —NR$^c$R$^c$, halogen, —C$_1$-C$_3$haloalkyl, —CN, —NC, —OCN, —SCN, —NO, —NO$_2$, =N$_2$, —N$_3$, —S(O)R$^a$, —S(O)$_2$R$^a$, —S(O)$_2$OR$^a$, —S(O)NR$^c$R$^c$, —S(O)$_2$NR$^c$R$^c$, —OS(O)R$^a$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(O)NR$^a$OR$^a$, —C(NH)NR$^c$R$^c$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NH)NR$^c$R$^c$ and —OC(NR$^a$)NR$^c$R$^c$;

each R$^c$ is, independently of the others, R$^a$ or a substituted or unsubstituted alkyl or heteroalkyl moiety such that the two R$^c$ moieties, taken together with the R$^b$ nitrogen atom to which they are both attached, form a heterocycloalkyl group containing 5 to 8 annular atoms, which optionally includes from 1 to 3 additional heteroatomic groups selected from the group consisting of —O—, —S—, —N(—(CH$_2$)$_y$—R$^a$)—, —N(—(CH$_2$)$_y$—C(O)OR$^a$)—, —N(—(CH$_2$)$_y$—S(O)$_2$R$^a$)—, and —N(—(CH$_2$)$_y$—C(O)NR$^a$R$^a$)—, where y is 0-6, wherein the heterocycloalkyl is optionally substituted with one or more R$^f$;

each R$^d$ is, independently of the others, selected from the group consisting of R$^a$ and R$^c$; and each R$^f$ is independently —C$_1$-C$_8$ alkoxy, —C$_1$-C$_8$ alkyl, —C$_1$-C$_6$ haloalkyl, cyano, nitro, amino, (C$_1$-C$_8$ alkyl)amino, di(C$_1$-C$_8$ alkyl)amino, phenyl, benzyl, oxo, or halogen, or any two R$^f$ bonded to adjacent atoms, taken together with the atoms to which they are each attached, form a fused saturated or unsaturated cycloalkyl or a fused saturated or unsaturated heterocycloalkyl group containing 5 to 8 annular atoms, wherein the formed cycloalkyl and heterocycloalkyl groups are optionally substituted with one or more groups which are each independently selected from halogen, C$_1$-C$_8$ alkyl, and phenyl.

2. The compound of claim 1 in which R$^5$ and R$^6$ are taken together to form a heteroalkylene bridge selected from the group consisting of —N=CH—Y—, —CH=N—Y—, and Y—N=CH—, wherein Y is NH, wherein each of the bridges is optionally substituted with 1 or 2 R$^g$, wherein each R$^g$ is independently, =OH, —C$_1$-C$_6$ alkoxy, (C$_1$-C$_3$) haloalkyloxy, —NR$^c$R$^c$, halogen, —C$_1$-C$_3$alkyl, —C$_1$-C$_3$haloalkyl, —CN, —NO$_2$, —S(O)$_2$R$^a$, —S(O)$_2$OR$^a$, —S(O)$_2$NR$^c$R$^c$, —OS(O)$_2$R$^a$, —OS(O)$_2$OR$^a$, —OS(O)$_2$NR$^c$R$^c$, —C(O)R$^a$, —C(O)OR$^a$, —C(O)NR$^c$R$^c$, —C(O)NR$^a$OR$^a$, —C(NR$^a$)NR$^c$R$^c$, —C(NOH)R$^a$, —C(NOH)NR$^c$R$^c$, —OC(O)R$^a$, —OC(O)OR$^a$, —OC(O)NR$^c$R$^c$, —OC(NR$^a$)NR$^c$R$^c$; aryl, or (C$_7$-C$_{20}$) arylalkyl.

3. The compound of claim 2 in which B is selected from the group consisting of

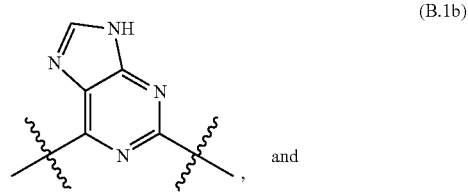

(B.1b)

and,

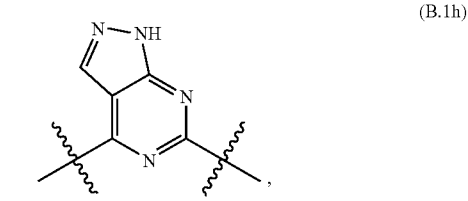

(B.1h)

, wherein each of the preceding groups are optionally substituted with 1 or 2 R$^g$.

4. The compound of claim 3 in which R$^2$ is phenyl substituted with one or more of the same or different R$^8$.

5. The compound of claim 4 in which R$^2$ is phenyl substituted with one R$^8$ group.

6. The compound of claim 5 in which the one R$^8$ substituent is positioned at the meta or para position of the R$^2$ phenyl.

7. The compound of claim 4 in which R$^2$ is phenyl substituted with two of the same or different R$^8$.

8. The compound of claim 7 in which the R$^8$ substituents are positioned 3,4- or 3,5- of the R$^2$ phenyl.

9. The compound of claim 4 in which R$^2$ is phenyl substituted with three of the same or different R$^8$.

10. The compound of claim 9 in which the R$^8$ substituents are positioned 3,4,5- of the R$^2$ phenyl.

11. The compound of claim 3 in which R$^2$ is of the formula

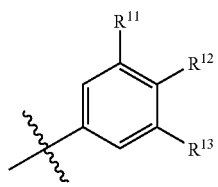

wherein one of R$^{11}$, R$^{12}$ or R$^{13}$ is a water-solubilizing group of the formula,

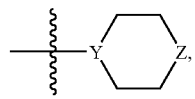

wherein Y is selected from the group consisting of CH and N, and Z is selected from the group consisting of CH$_2$, CH(R$^a$), O, S, NH, N—(CH$_2$)$_y$—R$^a$, N—(CH$_2$)$_y$—C(O)R$^a$, N—(CH$_2$)$_y$—C(O)OR$^a$, N—(CH$_2$)$_y$—S(O)$_2$ R$^a$, N—(CH$_2$)$_y$—S(O)$_2$OR$^a$ and N—(CH$_2$)$_y$—C(O)NR$^c$R$^c$, provided that Y and Z are not simultaneously CH and CH$_2$, respectively, or a water solubilizing group selected from the group consisting of morpholino, piperidinyl, (C$_1$-C$_6$) N-alkyl piperidinyl, N-methyl piperidinyl, N-(4-piperidinyl)piperidinyl, 4-(1-piperidinyl) piperidinyl, 1-pyrrolidinylpiperidinyl, 4-morpholinopiperidinyl, 4-(N-methyl-1-piperazinyl) piperidinyl, piperazinyl, (C$_1$-C$_6$) N-alkylpiperazinyl, N-methylpiperazinyl, N-ethyl piperidinyl, N-ethyl piperazinyl, N-cycloalkyl piperazinyl, N-cyclohexyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, and imidazolyl; and the other two of R$^{11}$, R$^{12}$ and R$^{13}$ are each, independently of one another, selected from the group consisting of hydrogen, C$_1$-C$_8$ alkyl, halo, hydroxy, (C$_1$-C$_3$) hydroxyalkyl, —O(CH$_2$)$_x$—R$^b$, —NR$^c$R$^c$, —C(O)NR$^c$R$^c$, and —C(O)NHR$^a$.

12. The compound of claim 11, wherein one of R$^{11}$, R$^{12}$, and R$^{13}$ is halogen, one is hydrogen, and the other is the water-solubilizing group.

13. The compound of claim 12, wherein one of R$^{11}$, R$^{12}$, and R$^{13}$ is fluoro, one is hydrogen, and the other is the water-solubilizing group.

14. The compound of claim 13, wherein one of R$^{12}$ is the water solubilizing group, R$^{11}$ is hydrogen; and R$^{13}$ is fluoro.

15. The compound of claim 11, wherein Y is N and Z is CH(R$^a$) or N—(CH$_2$)$_y$—R$^a$.

16. The compound of claim 15, wherein Z is CH(R$^a$1), wherein R$^a$1 is —NR$^c$R$^c$.

17. The compound of claim 3 in which R$^2$ is a heteroaryl, optionally substituted with one or more R$^h$, wherein each R$^h$ is independently =O, —OH, —C$_1$-C$_6$ alkoxy, —C$_1$-C$_3$alkyl, (C$_1$-C$_3$) haloalkyloxy, —NR$^c$R$^c$, halogen, —C$_1$-C$_3$haloalkyl, —CN, —NO$_2$, —S(O)$_2$R$^a$, —S(O)$_2$OR$^a$, —S(O)$_2$NR$^c$R$^c$, —C(O)R$^a$, —C(O)OR$^a$, —C(O)NR$^c$R$^c$, aryl, or (C$_7$-C$_{20}$) arylalkyl.

18. The compound of any one of claims 1-11 and 12-17 in which R$^4$ is selected from the group consisting of R$^7$

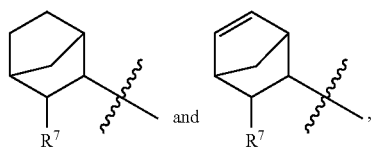

where R$^7$ is selected from the group consisting of —C(O)OR$^a$ and —C(O)NR$^c$R$^c$, where R$^a$ and R$^c$ are as previously defined.

19. The compound of claim 18, where R$^4$ is

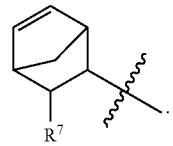

20. The compound of claim 18 in which R$^7$ is —C(O)O (C$_1$-C$_8$ alkyl) or —C(O)NH$_2$.

21. The compound of claim 20 in which R$^7$ is —C(O)NH$_2$.

22. A compound according to structural formula (XII):

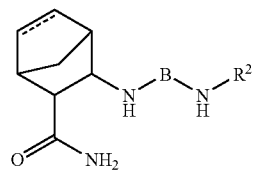

or a salt or N-oxide thereof, wherein B and R$^2$ are as defined in claim 1 and the bond including the dotted line is a single bond or a double bond.

23. The compound of claim 22 which is enriched in the corresponding diastereomer of structural formula (XIIa):

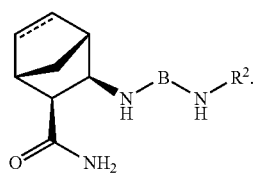

24. The compound of claim 23 in which $R^5$ and $R^6$ are taken together to form a heteroalkylene bridge selected from the group consisting of —CH=N—Y—, Y—N=CH—, and —N=CH—Y—, wherein Y is NH, wherein each of the bridges is optionally substituted with 1 or 2 $R^g$, wherein each $R^g$ is independently, =OH, —$C_1$-$C_6$ alkoxy, ($C_1$-$C_3$) haloalkyloxy, —$NR^cR^c$, halogen, —$C_1$-$C_3$alkyl, —$C_1$-$C_3$haloalkyl, —CN, —$NO_2$, —$S(O)_2R^a$, —$S(O)_2OR^a$, —$S(O)_2NR^cR^c$, —$OS(O)_2R^a$, —$OS(O)_2OR^a$, —$OS(O)_2NR^cR^c$, —$C(O)R^a$, —$C(O)OR^a$, —$C(O)NR^cR^c$, —$C(O)NR^aOR^a$, —$C(NR^a)NR^cR^c$, —$C(NOH)R^a$, —$C(NOH)NR^cR^c$, —$OC(O)R^a$, —$OC(O)OR^a$, —$C(O)NR^cR^c$, —$OC(NR^a)NR^cR^c$; aryl, or aralkyl.

25. The compound of claim 24 in which B is selected from the group consisting of

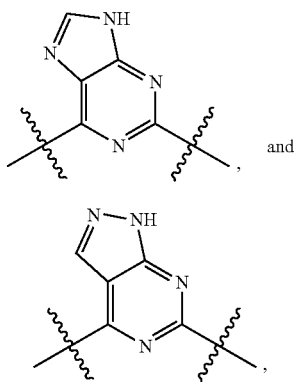

(B.1b)

(B.1h)

wherein each of the preceding groups are optionally substituted with 1 or 2 $R^g$.

26. The compound of claim 25 in which $R^2$ is phenyl substituted with one or more of the same or different $R^8$.

27. The compound of claim 26 in which $R^2$ is phenyl substituted with one $R^8$ group.

28. The compound of claim 27 in which the $R^8$ substituent is positioned at the meta or para position of the $R^2$ phenyl.

29. The compound of claim 26 in which $R^2$ is phenyl substituted with two of the same or different $R^8$.

30. The compound of claim 29 in which the substituents are positioned 3,4- or 3,5- of the $R^2$ phenyl.

31. The compound of claim 27 in which $R^2$ is phenyl substituted with three of the same or different $R^8$.

32. The compound of claim 31 in which the substituents are positioned 3,4,5- of the $R^2$ phenyl.

33. The compound of claim 25 in which $R^2$ is of the formula

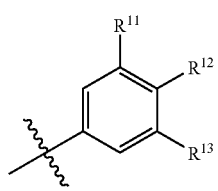

wherein one of $R^{11}$, $R^{12}$ or $R^{13}$ is a water-solubilizing group of the formula,

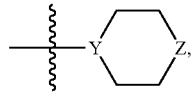

wherein Y is selected from the group consisting of CH and N, and Z is selected from the group consisting of $CH_2$, $CH(R^a)$, O, S, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2 R^a$, N—$(CH_2)_y$—$S(O)_2OR^a$ and N—$(CH_2)_y$—$C(O)NR^cR^c$, provided that Y and Z are not simultaneously CH and $CH_2$, respectively, or a water solubilizing group selected from the group consisting of morpholino, piperidinyl, ($C_1$-$C_6$) N-alkyl piperidinyl, N-methyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, ($C_1$-$C_6$) N-alkylpiperazinyl, N-methylpiperazinyl, N-ethyl piperidinyl, N-ethyl piperazinyl, N-cycloalkyl piperazinyl, N-cyclohexyl piperazinyl, pyrrolidinyl, N-alkyl pyrrolidinyl, N-methyl pyrrolidinyl, diazepinyl, N-ethyl pyrrolidinyl, N-alkyl azepinyl, N-methyl azepinyl, N-ethyl azepinyl, homopiperazinyl, N-methyl homopiperazinyl, N-ethyl homopiperazinyl, and imidazolyl and the other two of $R^{11}$, $R^{12}$ and $R^{13}$ are each, independently of one another, selected from the group consisting of hydrogen, $C_1$-$C_8$ alkyl, halo, hydroxy, ($C_1$-$C_3$) hydroxyalkyl, —$O(CH_2)_x$—$R^b$, —$NR^cR^c$, —$C(O)NR^cR^c$, and —$C(O)NHR^a$.

34. The compound of claim 32, wherein one of $R^{11}$, $R^{12}$, and $R^{13}$ is halogen, one is hydrogen, and the other is the water-solubilizing group.

35. The compound of claim 34, wherein one of $R^{11}$, $R^{12}$, and $R^{13}$ is fluoro, one is hydrogen, and the other is the water-solubilizing group.

36. The compound of claim 35, wherein one of $R^{12}$ is the water solubilizing group, $R^{11}$ is hydrogen; and $R^{13}$ is fluoro.

37. The compound of claim 32, wherein Y is N and Z is $CH(R^a)$ or N—$(CH_2)_y$—$R^a$.

38. The compound of claim 33, wherein Z is $CH(R^{a1})$, wherein $R^{a1}$ is —$NR^cR^c$.

39. The compound of claim 25 in which $R^2$ is a heteroaryl, optionally substituted with one or more $R^h$, wherein each $R^h$ is independently =O, —OH, —$C_1$-$C_6$ alkoxy, $C_1$-$C_3$alkyl, ($C_1$-$C_3$) haloalkyloxy, —$NR^cR^c$, halogen, —$C_1$-$C_3$haloalkyl, —CN, —$NO_2$, —$S(O)_2R^a$, —$S(O)_2OR^a$, —$S(O)_2NR^cR^c$, —$C(O)R^a$, —$C(O)OR^a$, —$C(O)NR^cR^c$, aryl, or ($C_7$-$C_{20}$) arylalkyl.

40. The compound of any one of claims 23-33 and 34-39 which is substantially pure in the corresponding diastereomer of structural formula (XIIa):

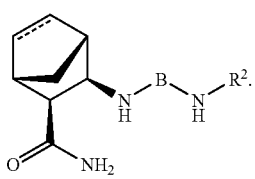

(XIIa)

41. The compound of claim 1 which is

Racemic-(2-exo,3-exo)-N6-(3-aminocarbonylbicyclo[2.2.1]hept-5-en-2-yl)-N2-(3,4,5-trimethoxy)phenyl-1H-purine-2,6-diamine;
Racemic-(2-exo,3-exo)-N6-(3-aminocarbonylbicyclo[2.2.1]hept-5-en-2-yl)-N2-[3-[2-(methylamino)-2-oxoethoxy]phenyl]]-1H-purine-2,6-diamine;
Racemic-(2-exo,3-exo)-N6-(3-aminocarbonylbicyclo[2.2.1]hept-5-en-2-yl)-N2-[3-(2-morpholin-4-yl-ethoxy)phenyl]-1H-purine-2,6-diamine;
Racemic-(2-exo,3-exo)-N6-(3-aminocarbonylbicyclo[2.2.1]hept-5-en-2-yl)-N2-(3-aminosulfonyl)phenyl-1H-purine-2,6-diamine;
Racemic-(2-exo,3-exo)-N6-(3-aminocarbonylbicyclo[2.2.1]hept-5-en-2-yl)-N2-(3,4-dihydro-3-oxo-2H-1,4-benzoxazin-7-yl)-1H-purine-2,6-diamine;
(1R,2R,3S,4S)-N6-(3-Aminocarbonylbicyclo[2.2.1]hept-5-en-2-yl)-N2-(3-aminosulfonyl)phenyl-1H-purine-2,6-diamine;
(1R,2R,3S,4S)-N6-(3-Aminocarbonylbicyclo[2.2.1]hept-5-en-2-yl)-N2-(3-fluoro)phenyl-1H-purine-2,6-diamine;
(1R,2R,3S,4S)-N6-(3-Aminocarbonylbicyclo[2.2.1]hept-5-en-2-yl)-N2-[3-[2-(methylamino)-2-oxoethoxy]phenyl]]-1H-purine-2,6-diamine;
(1S,2S,3R,4R)-N6-(3-Aminocarbonylbicyclo[2.2.1]hept-5-en-2-yl)-N2-[3-[2-(methylamino)-2-oxoethoxy]phenyl]]-1H-purine-2,6-diamine;
(1R,2R,3S,4S)-N6-(3-Aminocarbonylbicyclo[2.2.1]hept-5-en-2-yl)-N2-[3-(2-morpholin-4-yl-ethoxy)phenyl]-1H-purine-2,6-diamine;
(1S,2S,3R,4R)-N6-(3-Aminocarbonylbicyclo[2.2.1]hept-5-en-2-yl)-N2-[3-(2-morpholin-4-yl-ethoxy)phenyl]-1H-purine-2,6-diamine;
(1R,2R,3S,4S)-N6-(3-Aminocarbonylbicyclo[2.2.1]hept-5-en-2-yl)-N2-(3-aminosulfonyl-4-methyl)phenyl-1H-purine-2,6-diamine;
Racemic-(2-exo,3-exo)-N6-(3-aminocarbonylbicyclo[2.2.1]hept-5-en-2-yl)-N2-(3-methyl)phenyl-1H-purine-2,6-diamine;
Racemic-(2-exo,3-exo)-N6-(3-aminocarbonylbicyclo[2.2.1]hept-5-en-2-yl)-N2-(3-methoxy)phenyl-1H-purine-2,6-diamine;
Racemic-(2-exo,3-exo)-N6-(3-aminocarbonylbicyclo[2.2.1]hept-5-en-2-yl)-N2-(3-trifluoromethoxy)phenyl-1H-purine-2,6-diamine;
Racemic-(2-exo,3-exo)-N6-(3-aminocarbonylbicyclo[2.2.1]hept-5-en-2-yl)-N2-[3-methyl-4-(4-methylpiperazine-1-yl)phenyl]-1H-purine-2,6-diamine;
Racemic-(2-exo,3-exo)-N6-(3-aminocarbonylbicyclo[2.2.1]hept-5-en-2-yl)-N2-(4-cyanomethyl)phenyl-1H-purine-2,6-diamine;
Racemic-(2-exo,3-exo)-N6-(3-aminocarbonylbicyclo[2.2.1]hept-5-en-2-yl)-N2-(1H-indazol-6-yl)-1H-purine-2,6-diamine;
Racemic-(2-exo,3-exo)-N6-(3-aminocarbonylbicyclo[2.2.1]hept-5-en-2-yl)-N2-(3-aminocarbonyl)phenyl-1H-purine-2,6-diamine;
Racemic-(2-exo,3-exo)-N6-(3-aminocarbonylbicyclo[2.2.1]hept-5-en-2-yl)-N2-(1H-indol-5-yl)-1H-purine-2,6-diamine;
Racemic-(2-exo,3-exo)-N6-(3-aminocarbonylbicyclo[2.2.1]hept-5-en-2-yl)-N2-(3-hydroxy)phenyl-1H-purine-2,6-diamine;
Racemic-(2-exo,3-exo)-N6-(3-aminocarbonylbicyclo[2.2.1]hept-5-en-2-yl)-N2-(1,3-benzodioxol-5-yl)-1H-purine-2,6-diamine;
Racemic-(2-exo,3-exo)-N6-(3-aminocarbonylbicyclo[2.2.1]hept-5-en-2-yl)-N2-(4-piperidino)phenyl-1H-purine-2,6-diamine;
Racemic-(2-exo,3-exo)-N6-(3-aminocarbonylbicyclo[2.2.1]hept-5-en-2-yl)-N2-(3-fluoro)phenyl-1H-purine-2,6-diamine;
Racemic-(2-exo,3-exo)-N6-(3-aminocarbonylbicyclo[2.2.1]hept-5-en-2-yl)-N2-(3,4-difluoro)phenyl-1H-purine-2,6-diamine;
Racemic-(2-exo,3-exo-)-N6-(3-aminocarbonylbicyclo[2.2.1]hept-5-en-2-yl)-N2-(3-isopropoxy)phenyl-1H-purine-2,6-diamine;
Racemic-(2-exo,3-exo-)-N6-(3-aminocarbonylbicyclo[2.2.1]hept-5-en-2-yl)-N2-(3-methylthio)phenyl-1H-purine-2,6-diamine;
Racemic-(2-exo,3-exo-)-N6-(3-aminocarbonylbicyclo[2.2.1]hept-5-en-2-yl)-N2-(3-ethoxy)phenyl-1H-purine-2,6-diamine;
Racemic-(2-exo,3-exo-)-N6-(3-aminocarbonylbicyclo[2.2.1]hept-5-en-2-yl)-N2-[(4-fluoro-3-methyl)phenyl]-1H-purine-2,6-diamine;
Racemic-(2-exo,3-exo-)-N6-(3-aminocarbonylbicyclo[2.2.1]hept-5-en-2-yl)-N2-[4-(4-pyridinylmethyl)phenyl]-1H-purine-2,6-diamine;
Racemic-(2-exo,3-exo-)-N6-(3-aminocarbonylbicyclo[2.2.1]hept-5-en-2-yl)-N2-(3-fluoro-4-methy)phenyl-1H-purine-2,6-diamine;
Racemic-(2-exo,3-exo-)-N6-(3-aminocarbonylbicyclo[2.2.1]hept-5-en-2-yl)-N2-(1H-indol-4-yl)-1H-purine-2,6-diamine;
Racemic-(2-exo,3-exo-)-N6-(3-aminocarbonylbicyclo[2.2.1]hept-5-en-2-yl)-N2-(2-methoxy)phenyl-1H-purine-2,6-diamine;
Racemic-(2-exo,3-exo-)-N6-(3-aminocarbonylbicyclo[2.2.1]hept-5-en-2-yl)-N2-(3-methoxy)phenyl-1H-purine-2,6-diamine;
Racemic-(2-exo,3-exo-)-N6-(3-aminocarbonylbicyclo[2.2.1]hept-5-en-2-yl)-N2-(3,5-dimethoxy)phenyl-1H-purine-2,6-diamine;
Racemic-(2-exo,3-exo-)-N6-(3-aminocarbonylbicyclo[2.2.1]hept-5-en-2-yl)-N2-(3-aminosulfonyl-4-methoxy)phenyl-1H-purine-2,6-diamine;
Racemic-(2-exo,3-exo-)-N6-[3-(dimethylamino)carbonylbicyclo[2.2.1]hept-5-en-2-yl)]-N2-(3-isopropoxy)phenyl-1H-purine-2,6-diamine;
Racemic-(2-exo,3-exo-)-N6-[3-(dimethylamino)carbonylbicyclo[2.2.1]hept-5 en-2-yl)]-N2-(3-methyl)phenyl-1H-purine-2,6-diamine;
Racemic-(2-exo,3-exo-)-N6-[3-(dimethylamino)carbonylbicyclo[2.2.1]hept-5-en-2-yl)]-N2-(3-methoxy)phenyl-1H-purine-2,6-diamine;
Racemic-(2-exo,3-exo-)-N6-[3-(dimethylamino)carbonylbicyclo[2.2.1]hept-5-en-2-yl)]-N2-(3-methylthio)phenyl-1H-purine-2,6-diamine;
Racemic-(2-exo,3-exo-)-N6-[3-(dimethylamino)carbonylbicyclo[2.2.1]hept-5-en-2-yl)]-N2-(3-aminosulfonyl)phenyl-1H-purine-2,6-diamine;
Racemic-(2-exo,3-exo-)-N6-[3-(dimethylamino)carbonylbicyclo[2.2.1]hept-5-en-2-yl)]-N2-(4-piperidino)phenyl-1H-purine-2,6-diamine;
Racemic-(2-exo,3-exo-)-N6-[3-(dimethylamino)carbonylbicyclo[2.2.1]hept-5-en-2-yl)]-N2-[4-(4-pyridinylmethyl)phenyl]-1H-purine-2,6-diamine;
(1R,2R,3S,4S)-N6-(3-Aminocarbonylbicyclo[2.2.1]hept-5-en-2-yl)-N2-(1H-indol-5-yl)-1H-purine-2,6-diamine;
(1R,2R,3S,4S)-N6-(3-Aminocarbonylbicyclo[2.2.1]hept-5-en-2-yl)-N2-[4-(4-pyridinylmethyl)phenyl]-1H-purine-2,6-diamine;
Racemic-(2-exo,3-exo-)-N6-(3-aminocarbonylbicyclo[2.2.1]hept-5-en-2-yl)-N2-[4-(4-morpholinyl)phenyl]-1H-purine-2,6-diamine;
Racemic-(2-exo,3-exo-)-N6-(3-aminocarbonylbicyclo[2.2.1]hept-5-en-2-yl)-N2-(2-methyl-1H-indol-5-yl)-1H-purine-2,6-diamine;
Racemic-(2-exo,3-exo-)-N6-(3-aminocarbonylbicyclo[2.2.1]hept-5-en-2-yl)-N2-(3-aminocarbonyl-1H-indol-5-yl)-1H-purine-2,6-diamine;
(2S,3R)-3-(1-benzyl-6-(4-(2-(pyrrolidin-1-yl)ethoxy)phenylamino)-1H-pyrazolo[3,4-d]pyrimidin-4-ylamino)bicyclo[2.2.1]hept-5-ene-2-carboxamide;
Racemic-(2-exo,3-exo-)-N6-(3-aminocarbonylbicyclo[2.2.1]hept-5-en-2-yl)-N2-[3-(4-pyridinylmethoxy)]phenyl-1H-purine-2,6-diamine;
Racemic-(2-exo,3-exo-)-N6-(3-aminocarbonylbicyclo[2.2.1]hept-5-en-2-yl)-N2-[3-(3-pyridinylmethoxy)phenyl]-1H-purine-2,6-diamine;
Racemic-(2-exo,3-exo-)-N6-(3-aminocarbonylbicyclo[2.2.1]hept-5-en-2-yl)-N2-[4-(N-methoxy)-aminocarbonyl-methylphenyl]-1H-purine-2,6-diamine;
Racemic-(2-exo,3-exo-)-N6-(3-aminocarbonylbicyclo[2.2.1]hept-5-en-2-yl)-N2-[3-(N-methoxy)-aminocarbonyl-methylphenyl]-1H-purine-2,6-diamine;
Racemic-(2-exo,3-exo-)-N6-(3-aminocarbonylbicyclo[2.2.1]hept-5-en-2-yl)-N2-[4-[2-(1-pyrrolidinyl)ethoxy]phenyl]-1H-purine-2,6-diamine;
Racemic-(2-exo,3-exo-)-N6-(3-aminocarbonylbicyclo[2.2.1]hept-5-en-2-yl)-N2-[3-chloro-4-[2-(1-pyrrolidinyl)ethoxy]phenyl]-1H-purine-2,6-diamine;
Racemic-(2-exo,3-exo-)-N6-(3-aminocarbonylbicyclo[2.2.1]hept-5-en-2-yl)-N2-[3-fluoro-4-[2-(1-pyrrolidinyl)ethoxy]phenyl]-1H-purine-2,6-diamine.

42. A composition comprising a compound according to any one of claims 1-17, 19-23, 27-39 and 41 and a pharmaceutically acceptable carrier, excipient or diluent.

* * * * *